United States Patent
Nadler

(10) Patent No.: US 7,393,827 B2
(45) Date of Patent: Jul. 1, 2008

(54) PHARMACEUTICAL COMPOSITIONS AND METHODS FOR RESTORING β-CELL MASS AND FUNCTION

(75) Inventor: Jerry L. Nadler, Charlottesville, VA (US)

(73) Assignee: Diakine Therapeutics, Inc., Charlottesville, VA (US)

( * ) Notice: Subject to any disclaimer, the term of this patent is extended or adjusted under 35 U.S.C. 154(b) by 0 days.

(21) Appl. No.: 11/321,090

(22) Filed: Dec. 30, 2005

(65) Prior Publication Data

US 2006/0160736 A1 Jul. 20, 2006

Related U.S. Application Data

(60) Provisional application No. 60/640,523, filed on Dec. 30, 2004.

(51) Int. Cl.
A61K 38/26 (2006.01)
(52) U.S. Cl. ......................................................... 514/2
(58) Field of Classification Search ................... None
See application file for complete search history.

(56) References Cited

U.S. PATENT DOCUMENTS

| | | | |
|---|---|---|---|
| 5,288,721 A | 2/1994 | Klein et al. |
| 5,340,813 A | 8/1994 | Klein et al. |
| 5,424,286 A | 6/1995 | Eng |
| 5,473,070 A | 12/1995 | Underiner et al. |
| 5,567,704 A | 10/1996 | Bianco et al. |
| 5,580,873 A | 12/1996 | Bianco et al. |
| 5,580,874 A | 12/1996 | Bianco et al. |
| 5,585,380 A | 12/1996 | Bianco et al. |
| 5,612,349 A | 3/1997 | Bianco et al. |
| 5,620,984 A | 4/1997 | Bianco et al. |
| 5,621,102 A | 4/1997 | Bianco et al. |
| 5,629,315 A | 5/1997 | Bianco et al. |
| 5,629,423 A | 5/1997 | Klein et al. |
| 5,648,357 A | 7/1997 | Bianco et al. |
| 5,652,243 A | 7/1997 | Bianco et al. |
| 5,670,506 A | 9/1997 | Leigh et al. |
| 5,739,138 A | 4/1998 | Bianco et al. |
| 5,770,595 A | 6/1998 | Klein et al. |
| 5,780,476 A | 7/1998 | Underiner et al. |
| 5,792,772 A | 8/1998 | Bianco et al. |
| 5,795,897 A | 8/1998 | Underiner |
| 5,795,898 A | 8/1998 | Brown et al. |
| 5,801,182 A | 9/1998 | Klein et al. |
| 5,804,584 A | 9/1998 | Underiner et al. |
| 5,807,861 A | 9/1998 | Klein et al. |
| 5,807,862 A | 9/1998 | Klein et al. |
| 5,817,662 A | 10/1998 | Klein et al. |
| 5,859,018 A | 1/1999 | Brown et al. |
| 5,866,576 A | 2/1999 | Underiner et al. |
| 5,889,011 A | 3/1999 | Klein et al. |
| 5,929,081 A | 7/1999 | Brown et al. |
| 5,965,564 A | 10/1999 | Bianco et al. |
| 6,020,337 A | 2/2000 | Leigh et al. |
| 6,043,250 A | 3/2000 | Klein et al. |
| 6,057,328 A | 5/2000 | Singer et al. |
| 6,075,029 A | 6/2000 | Klein et al. |
| 6,100,271 A | 8/2000 | Klein et al. |
| 6,103,730 A | 8/2000 | Klein et al. |
| 6,121,270 A | 9/2000 | Underiner et al. |
| 6,133,274 A | 10/2000 | Underiner et al. |
| 6,469,017 B1 | 10/2002 | Klaus et al. |
| 6,586,429 B2 | 7/2003 | Gong et al. |
| 6,693,105 B1 | 2/2004 | Underiner et al. |
| 6,774,130 B2 | 8/2004 | Klein et al. |
| 6,780,865 B1 | 8/2004 | Porubek et al. |
| 6,858,576 B1 | 2/2005 | Young et al. |
| 6,872,700 B1 | 3/2005 | Young et al. |
| 6,878,715 B1 | 4/2005 | Klein et al. |
| 6,902,744 B1 | 6/2005 | Kolterman et al. |
| 6,956,026 B2 | 10/2005 | Beeley et al. |
| 2005/0233969 A1 | 10/2005 | Dong |

FOREIGN PATENT DOCUMENTS

| | | | |
|---|---|---|---|
| EP | 1 557 165 | | 7/2005 |
| WO | WO 00/66128 | * | 4/2000 |
| WO | WO 00/61583 | | 10/2000 |
| WO | WO 00/66128 | | 11/2000 |
| WO | WO 2004/028524 | | 4/2004 |

OTHER PUBLICATIONS

Yang et al. "The anti-inflammatory compound lisofylline prevents Type I diabetes in non-obese diabetic mice," Diabetologia, 2002, 45, 1307-14.*

Eckhoff et al. "Suppression of the c-Jun N-terminal kinase pathway by 17b-estradiol can preserve human islet functional mass from proinflammatory cytokine-induced destruction," Surgery, 2003, 134, 169-79.*

(Continued)

*Primary Examiner*—Cecilia Tsang
*Assistant Examiner*—Christina Marchetti Bradley
(74) *Attorney, Agent, or Firm*—Nixon & Venderhye P.C.

(57) ABSTRACT

Pharmaceutical compositions and methods for using are provided for restoring β-cell mass and function in a mammal in need thereof. The pharmaceutical compositions have a biological response modifier and a β-cell growth factor in admixture with a pharmaceutically acceptable carrier, adjuvant or vehicle.

1 Claim, 6 Drawing Sheets

OTHER PUBLICATIONS

Chen et al. "Lisofylline, a Novel Antiinflamatory Agent, Protects Pancreatic b-Cells from Proinflammatory Cytokine Damage by Promoting Mitochondrial Metabolism," Endocrinology, 2002, 143, 2341-2348.*

Xu et al. "Exendin-4 stimulates both β-cell replication and neogenesis, resulting in increased β-cell mass and improved glucose tolerance in diabetic rats," Diabetes, 1999, 48, 2270-6.*

Augustyns et al. "Dipeptidyl peptidase IV inhibitors as new therapeutic agents for the treatment of Type 2 diabetes," Exp. Opin. Ther. Patents, 2003, 13, 499-510.* von Herrath et al. "Progress in the Development of Immune-Based Therapies for Type 1 Diabetes Mellitus," Biodrugs, 2006, 20, 341-50.*

Abraham, E.J., et al., "Insulinotrophic Hormone Glucagon-Like Peptide-1 Differentiation of Human Pancreatic Islet-Derived Progenitor Cells into Insulin-Producing Cells," *Endocrinology*, 143(8):3152-3161 (2002).

Aliberti, J., et al., "Lipoxin-mediated inhibition of IL-12 production by DCs: a mechanism for regulation of microbial immunity," *Nature Immunology*, 3(1):76-82 (2002).

Aziz, A., et al., "Exendin-4, a GLP-1 Receptor Agonist, Modulates the Effect of Macronutrients on Food Intake by Rats," *Nutritional Neurosciences*, American Society for Nutritional Sciences, (Manuscript) pp. 990-995 (2002).

Bleich, D., et al., "Lisofylline, an inhibitor of unsaturated phosphatidic acid generation, ameliorates interleukin-1 beta-induced dysfunction in cultured rat islets," *Endocrinology*, 137:4871-4877 (1996).

Bright, J.J., et al., "Prevention of experimental allergic encephalomyelitis via inhibition of IL-12 signaling and IL-12-mediated Th1 differentiation: an effect of the novel anti-inflammatory drug lisofylline," *Journal of Immunology*, 161:7015-7022 (1998).

Bulotta, A., et al., "Cultured pancreatic ductal cells undergo cell cycle re-distribution and beta-cell-like differentiation in response to glucagon-like peptide-1," *Journal of Molecular Endocrinology*, 29:347-360 (2002).

Bursten, S.L., et al., "Lisofylline causes rapid and prolonged suppression of serum levels of free fatty acids" *Journal of Pharmacology & Experimental Therapeutics*, 284:337-345 (1998).

Buteau, J., et al., "Protein kinase Cζ activation mediates glucagon-like peptide-1-induced pancreatic beta-cell proliferation," *Diabetes*, 50:2237-2243 (2001).

Chakrabarti, S. K., et al., "Quantitative assessment of gene targeting in vitro and in vivo by the pancreatic transcription factor, Pdx1," *The Journal of Biological Chemistry*, 277(15):13286-13293 (2002).

Chakrabarti, S. K., et al., "Transcription factors direct the development and function of pancreatic beta cells," *Trends Endocrinol. Metab.*, 14:78-84 (2003).

Chen, M., et al., "Lisofylline, a Novel Antiinflammatory Agent, Protects Pancreatic β-Cells from Proinflammatory Cytokine Damage by Promoting Mitochondrial Metabolism," *Endocrinology*, 143(6):2341-2348 (2002).

Chen, Y.E., et al, "Tissue-specific expression of unique mRNAs that encode proglucagon-derived peptides or exendin 4 in the lizard," *The Journal of Biological Chemistry*, 272:4108-4115 (1997).

Coon, M. E., et al., "Selective pharmacologic inhibition of murine and human IL-12-dependent Th1 differentiation and IL-12 signaling," *Journal of Immunology*, 163:6567-6574 (1999).

Cottet, S., et al., "cFLIP protein prevents tumor necrosis factor-alpha-mediated induction of caspase-8-dependent apoptosis in insulin-secreting betaTc-Tet cells," *Diabetes*, 51:1805-1814 (2002).

Deleon, D. D., et al., "Role of Endogenous Glucagon-Like Peptide-1 in Islet Regeneration After Partial Pancreatectomy," *Diabetes*, 52:365-371 (2003).

Delaporte, Q., et al., "Comparison between the growth pattern of cell cultures from normal and Duchenne dystrophy muscle," *Journal of Neurological Sciences*, 64:149-160 (1984).

Drucker, D., "Minireview: The Glucagon-Like Peptides," *Endocrinology*, 142(2):521-527 (2001).

Egan, J. M., et al., "Effects of 1-mo bolus subcutaneous administration of exendin-4 in type 2 diabetes," *American Journal of Physiology Endocrinology & Metabolism*, 284(6):E1072-E1079 (2003).

Egan, J. M., et al., "GLP-1 receptor agonists are growth and differentiation factors for pancreatic islet beta cells," *Diabetes/Metabolism Research Reviews*, 19:115-123 (2003).

Eng, J., et al., "Isolation and characterization of exendin-4, an exendin-3 analogue, from Heloderma suspectum venom. Further evidence for an exendin receptor on dispersed acini from guinea pig pancreas," *The Journal of Biological Chemistry*, 267(11):7402-7405 (1992).

Farilla, L., et al., "Glucagon-like peptide-1 promotes islet cell growth and inhibits apoptosis in Zucker diabetic rats," *Endocrinology*, 143(11):4397-4408 (2002).

Fineman, M. S., et al., "Effect on glycemic control of exenatide (synthetic exendin-4) additive to existing metformin and/or sulfonylurea treatment in patients with type 2 diabetes," *Diabetes Care*, 26(8):2370-2377 (2003).

Flynn, M., et al., "Efficient Delivery of Small Interfering RNA for Inhibition of IL-12p40 Expression in vivo," *Journal of Inflammation*, 1(4):[12 pages] (2004).

Gasa, R., et al., "Proendocrine Genes Coordinate the Pancreatic Islet Differentiation Program in vitro," *Proceedings of the National Academy of Sciences of the United States of America*, 101(36):13245-13250 (2004).

Ge., J., et al., "Advanced Glycosylation End Products Might Promote Atherosclerosis Through Inducing the Immune Maturation of Dendritic Cells," *Arterioscler. Thromb. Vasc. Biol.*, 25:2157-2163 (2005).

Goke, R., et al., "Exendin-4 is a high potency agonist and truncated exendin-(9-39)-amide an antagonist at the glucagon-like peptide 1-(7-36)-amide receptor of insulin-secreting beta-cells," *The Journal of Biological Chemistry*, 268(26):19650-19655 (1993).

Greig, N. H., et al., "Once daily injection of exendin-4 to diabetic mice achieves long-term beneficial effects on blood glucose concentrations." *Diabetologia*, 42:45-50 (1999).

Guidot, D.M., et al., "Modulating phosphatidic acid metabolism decreases oxidative injury in rat lungs," *American Journal of Physiology*, 273:L957-L966 (1997).

Gutniak, M., et al., "Antidiabetogenic effect of glucagon-like peptide-1 (7-36)amide in normal subjects and patients with diabetes mellitus," *New England Journal of Medicine*, 326:1316-1322 (1992).

Hansotia, T., et al., "Double incretin receptor knockout (DIRKO) mice reveal an essential role for the enteroinsular axis in transducing the glucoregulatory actions of DPP-IV inhibitors," *Diabetes*, 53:1326-1335 (2004).

Hardikar, AA, et al., "Functional maturation of fetal porcine beta-cells by glucagon-like peptide 1 and cholecystokinin," *Endocrinology*, 143(9):3505-3514 (2002).

Hui, H.; et al., "Glucagon-like peptide 1 induces differentiation of islet duodenal homeobox-1 -positive pancreatic ductal cells into insulin-secreting cells," *Diabetes*, 50:785-796 (2001).

Hui, H, et al., "Glucagon-like peptide-1 inhibits apoptosis of insulin-secreting cells via a cyclic 5'-adenosine monophosphate-dependent protein kinase A- and a phosphatidylinositol 3-kinase-dependent pathway." *Endocrinology*, 144(4):1444-1455 (2003).

Idris, I., et al., "Exendin-4 increases insulin sensitivity via a PI-3-kinase-dependent mechanism: contrasting effects of GLP-1," *Biochemical Pharmacology*, 63:993-996 (2002).

Kirsch, B. M., et al., "The Active Metabolite of Leflunomide, A77 1726, Interferes with Dendritic Cell Function," *Arthritis Research & Therapy*, 7:R694-R703 (2005).

Komatsu, R., et al., "Glucagonostatic and insulinotropic action of glucagonlike peptide 1-(7-36)-amide," *Diabetes*, 38:902-905 (1989).

Kusaba, H., et al., "Interleukin-12-Induced Interferon-γ Production by Human Peripheral Blood T Cells Is Regulated by Mammalian Target of Rapamycin (mTOR)," *The Journal of Biological Chemistry*, 280(2):1037-1043 (2005).

Li, Y., et al., "Glucagon-Like Peptide-1 Receptor Signaling Modulates β Cell Apoptosis," *The Journal of Biological Chemistry*, 278(1):471-478 (2003).

Ogawa, N., et al., "Cure of Overt Diabetes in NOD Mice by Transient Treatment With Anti-Lymphocyte Serum and Exendin-4," *Diabetes*, 53:1700-1705 (2004).

Wheeler, et al., "Functional Expression of the Rat Pancreatic Islet Glucose-Dependent Insulinotropic Polypeptide Receptor: Ligand Binding and Interacellular Signaling Properties," *Endocrinology*, 136(10):4629-4639.

Mannon, P.J., et al., "Anti-Interleukin-12 Antibody for Active Crohn's Disease," *New England Journal Medicine*, 351:2069-2079 (2004).

Movassat, J., et al., "Exendin 4 up-regulates expression of PDX 1 and hastens differentiation and maturation of human fetal pancreatic cells." *Journal of Clinical Endocrinology and Metabolism* 87:4775-4781 (2002).

Nathan, D.M., et al., "Insulinotropic action of glucagonlike peptide-1-(7-37) in diabetic and nondiabetic subjects," *Diabetes Care*, 15(2):270-276 (1992).

Nauck, M.A., et al., "Additive insulinotropic effects of exogenous synthetic human gastric inhibitory polypeptide and glucagon-like peptide-1-(7-36) amide infused at near-physiological insulinotropic hormone and glucose concentrations," *Journal of Clinical Endocrinology and Metabolism*, 76:912-917 (1993).

Nauck, M. A., et al., "Normalization of fasting hyperglycaemia by exogenous glucagon-like peptide 1 (7-36 amide) in type 2 (non-insulin-dependent) diabetic patients," *Diabetologia*, 36:741-744 (1993).

Nauck, M.A., et al., "Preserved incretin activity of glucagon-like peptide 1 [7-36 amide] but not of synthetic human gastric inhibitory polypeptide in patients with type-2 diabetes mellitus," *J Clin Invest*, 91:301-307 (1993).

Oka, Y, et al., "Selective downregulation of neutrophils by a phosphatidic acid generation inhibitor in a porcine sepsis model," *Journal of Surgical Research*, 81:147-155 (1999).

Orskov, C., "Glucagon-like peptide-1, a new hormone of the entero-insular axis," *Diabetologia*, 35(8):701-711 (1992).

Parkes, D.G., et al., "Insulinotropic actions of exendin-4 and glucagon-like peptide-1 in vivo and in vitro." *Metabolism*, 50(5):583-589 (2001).

Raufman, J.P., et al., "Truncated glucagon-like peptide-1 interacts with exendin receptors on dispersed acini from guinea pig pancreas. Identification of a mammalian analogue of the reptilian peptide exendin-4," *The Journal of Biological Chemistry*, 267(30):21432-21437 (1992).

Rice, G.C., et al., "CT-1501R selectively inhibits induced inflammatory monokines in human whole blood ex vivo," *Shock*, 1(4):254-266 (1994).

Rice, G.C., et al., "Protection from endotoxic shock in mice by pharmacologic inhibition of phosphatidic acid," *Proceedings of the National Academy of Sciences of the United States of America*, 91:3857-3861 (1994).

Synta Pharmaceuticals Corp. Press Release, "Synta Pharmaceuticals Presents Phase 2a Data at DDWfor STA-5326 in Patients with Crohn's Disease," May 18, 2005, printed from www.syntapharma.com/documents/news051805.htm.

Tasaki, O., et al., "Effects of heparin and lisofylline on pulmonary function after smoke inhalation injury in an ovine model," *Critical Care Medicine*, 30(3):637-643 (2002).

Thorens, B., et al., "Cloning and functional expression of the human islet GLP-1 receptor. Demonstration that exendin-4 is an agonist and exendin-(9-39) an antagonist of the receptor," *Diabetes*, 42:1678-1682 (1993).

Todd, J.F., et al., "Glucagon-like peptide-1 (GLP-1): a trial of treatment in non-insulin-dependent diabetes mellitus," *European Journal of Clinical Investigation*, 27:533-536 (1997).

Touchette, N., "Protein Could Lead to Diabetes Treatments," downloaded from Genome News Network (http://www.genomenewsnetwork.org/) posted May 14, 2004 (2 pages).

Tourrel, C., et al., "Glucagon-Like Peptide-1 (GLP-1) or Exendin-4 Treatment Limited to the Pre-Diabetic period Limits the Progression to Overt NIDDM in the Adult OK Rat," *Diabetes*, 50:1562-1570 (2001).

Urusova, I. A., et al., "GLP-1 Inhibition of Pancreatic Islet Cell Apoptosis," *Trends in Endocrinology and Metabolism*, 15(1):27-33 (2004).

Vandenbroeck, K., et al., "Inhibiting Cytokines of the Interleukin-12 family: Recent Advances and Novel Challenges," *Journal of Pharmacy and Pharmacology*, 56:145-160 (2004).

Vella, A., et al., "Lack of effect of exendin-4 and glucagon-like peptide-1-(7-36)-amide on insulin action in non-diabetic humans," *Diabetologia*, 45:1410-1415 (2002).

Watford, W.T., "Signaling by IL-12 and IL-23 and the Immunoregulatory Roles of STAT4," *Immunological Reviews*, 202:139-156 (2004).

Wattanasirichaigoon, S., et al., "Lisofylline ameliorates intestinal and hepatic injury induced by hemorrhage and resuscitation in rats," *Critical Care Medicine*, 28(5):1540-1549 (2000).

Waxman, K, et al., "Lisofylline decreases white cell adhesiveness and improves survival after experimental hemorrhagic shock," *Critical Care Medicine*, 24(10):1724-1728 (1996).

Xu, G., et al., "Exendin-4 stimulates both beta-cell replication and neogenesis, resulting in increased beta-cell mass and improved glucose tolerance in diabetic rats," *Diabetes*, 48:2270-2276 (1999).

Yang, Z., et al., "Autoimmune diabetes is blocked in Stat4-deficient mice," *J Autoimmun*, 22:191-200 (2004).

Yang, Z., et al., "Cardiac allograft tolerance induced by infra-arterial infusion of recombinant adenoviral CTLA4Ig," *Transplantation*, 67(12):1517-1523 (1999).

Yang, Z., et al., "Inflammation blockade improves human pancreatic islet function and viability," *American Journal of Transplantion*, 5:475-483 (2005).

Yang, Z., et al., "Inflammation blockade improves pancreatic islet function," *Transplantation Proceedings*, 36(9):2864-2865(2004).

Yang, Z., et al., "Inhibition of STAT4 activation by lisofylline is associated with the protection of autoimmune diabetes," *Ann. NY. Acad. Sci.*, 1005:409-411 (2003).

Yang, Z., et al., "Lisofylline: A Potential Lead for the Treatment of Diabetes," *Biochemical Pharmacology*, 69:1-5 (2005).

Yang, Z., et al., "The Anti-Inflammatory Compound Lisofylline Prevents Type I Diabetes in Non-Obese Diabetic Mice," *Diabetologia*, 45:1307-1314 (2002).

Yang, Z, et al., "The novel anti-inflammatory agent lisofylline prevents autoimmune diabetic recurrence after islet transplantation," *Transplantation*, 77(1):55-60 (2004).

Yang, Z, et al., "The novel anti-inflammatory compound, lisofylline, prevents diabetes in multiple low-dose streptozotocin-treated mice," *Pancreas*, 26(4):e99-104 (2003).

Young, A.A., et al.; "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," *Diabetes*, 48:1026-1034 (1999).

Zhou, Z., et al., "Exendin-4 Differentiation of Human Pancreatic Duct Cell Line Into Endocrine Cells: Involvement of PDX-1 and HNF3β Transcription Factors," *Journal Of Cellular Physiology*, 192:304-314 (2002).

Zhou, J., et al., "Glucagon-like peptide 1 and exendin-4 convert pancreatic AR42J cells into glucagon- and insulin-producing cells," *Diabetes*, 48:2358-2366 (1999).

Carter, J.D., et al., "Reversal of Type-1 Diabetes in NOD Mice with Combination of Exendin-4 and Lisofylline,", *Diabetes*, 54(Suppl. 1):A67, Abstract 270-OR (2005).

Yang, Z., et al., "Combined Treatment with Lisofylline and Exendin-4 Reverses Autoimmune Diabetes", *Biochemical and Biophysical Research Communications*, 344(3):1017-1022 (2006).

* cited by examiner

Insulin Staining

Untreated

Ex-4+LSF

PHARMACEUTICAL COMPOSITIONS AND METHODS FOR RESTORING β-CELL MASS AND FUNCTION

CROSS REFERENCE TO RELATED PATENT APPLICATION

This patent application is related to, and claims the benefit of, U.S. Provisional Patent Application No. 60/640,523, filed Dec. 30, 2004, the entire disclosure of which is incorporated herein by reference.

FIELD OF THE INVENTION

The present invention relates to the use of pharmaceutical compositions and methods for using same for (1) restoring β-cell mass and function in an individual in need thereof; (2) preventing the development of, or reversing, Type 1 diabetes in an individual in need thereof; (3) for preventing the development of, or reversing, latent autoimmune diabetes of adults (LADA) in an individual in need thereof; and/or (4) for treating Type 2 diabetes by increasing the number of functional insulin-producing cells (e.g., β-cells) in an individual in need thereof.

BACKGROUND OF THE INVENTION

Insulin is a hormone produced in the pancreas by β-cells. The function of insulin is to regulate the amount of glucose (sugar) in the blood, which enters cells through receptors that accept insulin and allow glucose to enter. Once inside, glucose can be used as fuel. Excess glucose is stored in the liver and muscles in a form called glycogen. When blood glucose levels are low, the liver releases glycogen to form glucose. Without insulin, glucose has difficulty entering cells.

In persons with diabetes mellitus, one of the most common metabolic diseases affecting hundreds of millions of individuals worldwide, the pancreas produces no insulin, too little insulin to control blood sugar, or defective insulin. Without insulin, these symptoms progress to dehydration, resulting in low blood volume, increased pulse rate, and dry, flushed, skin. In addition, ketones accumulate in the blood faster than the body is able to eliminate them through the urine or exhaled breath. Respiration becomes rapid, and shallow and breath has a fruity odor. Other symptoms indicating a progression towards diabetic ketoacidotic coma (DKA) include vomiting, stomach pains, and a decreased level of consciousness. The disease leads to serious complications, including hyperglycemia, macroangiopathy, microangiopathy, neuropathy, nephropathy and retinopathy. As a result, diabetes adversely affects the quality of life.

There are two forms of diabetes mellitus: (1) insulin dependent or Type 1 diabetes (a.k.a., Juvenile Diabetes, Brittle Diabetes, Insulin Dependent Diabetes Mellitus (IDDM)) and (2) non-insulin-dependent or Type II diabetes (a.k.a., NIDDM). Type 1 diabetes develops most often in young people but can appear in adults. Type 2 diabetes develops most often in middle aged and older adults, but can appear in young people. Diabetes is a disease derived from multiple causative factors and characterized by elevated levels of plasma glucose (hyperglycemia) in the fasting state or after administration of glucose during an oral glucose tolerance test.

Type 1 diabetes is an autoimmune disease condition characterized by high blood glucose levels caused by a total lack of insulin, i.e., a complete loss of pancreatic β-cell function and mass. Type 1 diabetes occurs when a person's immune system attacks the insulin producing β-cells in the pancreas and destroys them. It is believed that the Interleukin 12 (IL-12) family of cytokines and downstream activation of Signal Transducers and Activators of Transcription (STAT) family members, e.g., STAT-4, which are believed to be regulators of T cell differentiation involved in immune responses, play a major role in the processes that lead to autoimmune β-cell destruction. The pancreas then produces little or no insulin. The most common Type 1 diabetes symptoms experienced include excessive thirst (polydipsia), frequent urination (polyuria), extreme hunger (polyphagia), extreme fatigue, and weight loss. These symptoms are caused by hyperglycemia and a breakdown of body fats. Persons diagnosed with Type 1 diabetes typically exhibit blood sugar levels over 300 mg and ketones present in their urine. Restoration of β-cell mass and insulin production can fully reverse the diabetic state. Evidence suggests that people with long standing Type 1 diabetes have β-cells that continue to form but are undesirably destroyed by continued autoimmune destruction. Therefore, pharmaceutical compositions and methods for arresting autoimmune β-cell damage would provide an effective way to restore normal β-cell mass levels and reverse or cure Type 1 diabetes.

LADA is a newly recognized subset of Type 1 diabetes and is thought to account for up to 10%-20% of all cases of diabetes. LADA is often present in people initially diagnosed with Type 2 diabetes. Although it has characteristics similar to adult onset type 1 diabetes, the beta-cell destruction is considered to be less aggressive in its progression.

Type 2 diabetes results from a combination of insulin resistance and impaired insulin secretion but ultimately many people with Type 2 diabetes show markedly reduced pancreatic β-cell mass and function which, in turn, causes Type 2 diabetic persons to have a "relative" deficiency of insulin because pancreatic β-cells are producing some insulin, but the insulin is either too little or isn't working properly to adequately allow glucose into cells to produce energy. Recent autopsy studies have shown clear evidence of ongoing β-cell death (apoptosis) in people with Type 2 diabetes. Therefore, therapeutic approaches to arrest β-cell death could provide a significant treatment for reversing or curing Type 2 diabetes.

Uncontrolled Type 2 diabetes leads to excess glucose in the blood, resulting in hyperglycemia, or high blood sugar. A person with Type 2 diabetes experiences fatigue, increased thirst, frequent urination, dry, itchy skin, blurred vision, slow healing cuts or sores, more infections than usual, numbness and tingling in feet. Without treatment, a person with Type 2 diabetes will become dehydrated and develop a dangerously low blood volume. If Type 2 diabetes remains uncontrolled for a long period of time, more serious symptoms may result, including severe hyperglycemia (blood sugar over 600 mg) lethargy, confusion, shock, and ultimately "hyperosmolar hyperglycemic non-ketotic coma." Persistent or uncontrolled hyperglycemia is associated with increased and premature morbidity and mortality. As such, therapeutic control of glucose homeostasis, lipid metabolism, obesity, and hypertension are critically important in the clinical management and treatment of diabetes mellitus.

The object of diabetes treatments is to prevent the occurrence of the above-mentioned chronic complications, slow disease progression by improving hyperglycemic status, or reversing/curing it. Conventional methods for treating diabetes have included administration of fluids and insulin in the case of Type I diabetes and administration of various hypoglycemic agents in the case of Type II diabetes. Hypoglycemic agents such as insulin preparations, insulin secretagogues, insulin sensitizers and α-glucosidase inhibitors have been widely applied as the method for the clinical treatment. Examples include acarbose (PrecoseJ), glimeprimide (AmarylJ), metformin (Glucophage7), nateglinide (Starlix7), pioglitazone (Actos7), repaglinide (PrandinJ), rosiglitazone (Avandia7), sulfonylureas, Orlistat (Xenical7), exenatide (Byetta), and the like. Many of the known hypoglycemic agents, however, exhibit undesirable side effects and are toxic in certain cases. For example, in the case of the diabetic patients with seriously lowered pancreatic insulin secretion, effectiveness of insulin secretagogues and insulin sensitizers is diminished. Similarly, in the case of the diabetic patients whose insulin resistance is significantly high, effectiveness of insulin preparations and insulin secretagogues is diminished.

In principle, diabetes mellitus could be "cured" by a successful transplant of the tissue containing cells that secrete or produce insulin, i.e., the islets of Langerhans. Transplantation of insulin producing cells (a.k.a., islets) has been tried as a method to reverse or cure Type 1 diabetes, but there are significant risks associated with the surgery and with the toxic immunosuppression type drugs that need to be taken to prevent or mitigate allograft rejection and autoimmune reoccurrence. Immunosuppression drugs act by reducing the activity of a recipient's immune system so that the transplanted insulin producing cells are not rejected. Such immunosuppression, however, entails substantial risks and there are considerable difficulties attendant in minimizing the antigenic differences (matching) between a donor and a recipient that increases the costs and reduces the availability of this mode of therapy. In addition, conventional immunosuppression is generally not successful in enabling islet transplantation. Moreover, there are over 1 million people with Type 1 diabetes in the United States today, but the supply of cadaveric pancreatic tissue for islets is limited. For instance, only 6,000 organs are available per year and 2 or 3 organs are needed to provide enough islets to reverse Type 1 diabetes in one person. Therefore, providing a new source of functioning (insulin producing) β-cells is urgently needed. In addition, if a diabetic patient's own cells (pancreatic or other cell types) could be genetically engineered or induced to grow and differentiate into functioning β-cells, then there would be little or no need to use toxic anti-rejection medications. As previously mentioned, there continues to be the capacity for new β-cell formation in people with Type 1 diabetes. However, continued autoimmunity leads to active destruction of any newly formed or transplanted β-cells. Development of new immunomodulating agents would provide a new way to fully reverse β-cell disfunction in Type 1 diabetes without the need for islet cell transplantation or toxic anti-rejection immunosuppressants. Further, the combination therapy approach provided by a preferred embodiment of present invention would be a major improvement in cellular replacement therapy by reducing the amount of transplanted cells needed to reverse or cure Type 1 diabetes, facilitating the increase viability and growth of insulin producing cells, thereby improving success rates.

Glucagon-Like Peptide (GLP-1) and Gastric Inhibitory Polypeptide (GIP)

Incretins are intestinal hormones released after meal ingestion that stimulate insulin secretion. GLP-1 is a 300-amino-acid (peptide) incretin synthesized in the small and large intestine by the L-type cells of the gastroenteropancreatic endocrine system and is released in response to food ingestion. GLP-1 enhances glucose-stimulated postprandial insulin secretion, stimulates insulin gene expression and proinsulin biosynthesis, inhibits pancreatic glucagons release, gastric emptying, and acid secretion. GIP is another insulin releasing hormone secreted from endocrine cells in the intestinal tract in response to food intake. Together with autonomic nerves, GLP-1 and GIP play a vital supporting role to the pancreatic islets in the control of blood glucose homeostasis and nutrient metabolism.

GLP-1 shows potent insulinotropic action in both diabetic and nondiabetics. GLP-1 causes expansion of beta-cell mass via proliferation of insulin-producing cells. GLP-1 shows an ability to stimulate β-cell neogenesis in streptozotocin (STZ)-treated newborn rats, resulting in persistent improvement of glucose homeostasis to adult age. GLP-1 induces differentiation of islet duodenal homeobox-1-positive pancreatic ductal cells into insulin-secreting cells by enhancing expression of transcription factors PDX-1 and HNF3. GLP-1 has been shown to promote functional maturation of fetal porcine β-cells and islet cell growth in a Type 2 diabetic rat model. Cloning and functional expression of GLP-1 receptors are completed in human islets. GLP-1 receptor signaling directly modifies the susceptibility of β-cells to apoptotic injury that may be the potential mechanism linking to preservation and enhancement of β-cell mass and function. GLP-1 receptor signaling, however, does not seem essential for glucose-stimulated insulin secretion, as shown in GPL-1 receptor knockout mice, which suggests that the functional signaling of GLP-1 in β-cells may be in addition to the one initiated by glucose.

GLP-1 has been studied as a potential drug for the management of diabetes for two reasons: (i) its effect on β-cell growth; and (ii) its insulin-stimulating effect with minimal risk of hypoglycemia and absence of effect on insulin action in non-diabetic humans. In limited clinical trails, GPL-1 is effective in treating Type 2 diabetic patients, showing a significant improvement in postprandial glycemic control and normalization of fasting hyperglycemia due to its ability of insulinotropic activity.

GIP is released from intestinal endocrine K-cells into the bloodstream following ingestion of carbohydrate, protein and particularly fat. GIP's major physiological role is generally believed to be that of an incretin hormone that targets pancreatic islets to enhance insulin secretion and help reduce postprandial hyperglycemia. GIP acts through binding to specific G-protein coupled GIP receptors located on pancreatic beta-cells (Wheeler, M. B. et al., 1995, Endocrinology 136:4629-4639). GIP has been shown to stimulate β-cell proliferation synergistically with glucose in the islet INS-1 cell line, in association with induction of MAPK and PI 3-kinase. Similarly, GIP exerts anti-apoptotic actions in studies using INS-1 β-cells. Like glucagon-like peptide-1 (GLP-1), the ability to stimulate insulin secretion plus other potentially beneficial actions on pancreatic beta-cell growth and differentiation have led to much interest in using GLP-1 or GIP and analogs thereof for the treatment of type 2 diabetes.

Neither, GLP-1 nor GIP, however, appear suitable for therapeutic use in chronic disorders, such as Type 2 diabetes because GLP-1 and GIP are rapidly cleared from blood circulation (half life of about 1.5 min.) by the ubiquitous enzyme dipeptidyl peptidase-IV (DPP-IV). Exogenously administered GLP-1 is also rapidly degraded. This metabolic instability limits the therapeutic potential of native GLP-1 and GIP.

Exendin-4 (Ex-4)

As an analog of GLP-1, Ex-4 was first isolated from the salivary secretions of a South American lizard known as the Gila monster (*Heloderma suspectum*). Ex-4 consists 39-amino acids with 53% structural homology to mammalian GLP-1. Ex-4 is capable of binding to both human and rat GLP-1 receptors and shows similar pharmacological and biological properties of GLP-1. As a more potent agent than GLP-1, Ex-4 is strongly capable of increasing β-cell mass by enhancing both cell replication and neogenesis, and by inhibiting the apoptosis of β-cells.

In spite of similarities, Ex-4 differs from GLP-1: (i) Ex-4 is resistant to DPP-IV cleavage, resulting in a long-lasting biological function that is potentially suitable for therapeutic use; (ii) Ex-4 has greater insulinotropic efficacy; and (iii) although both GLP-1 and Ex-4 have similar effects to augment insulin-stimulated glucose uptake and metabolism in skeletal muscle, Ex-4 also increases glucose uptake in adipocytes. Ex-4 may also use different signaling pathways, possibly through a receptor other than the GLP-1 receptor. This may render Ex-4 more effective in reducing blood glucose by simultaneously stimulating β-cell insulin secretion and increasing glucose utilization in both skeletal muscle and fat tissue. Ex-4 has also been studied for treatment of Type 2 diabetes, as an additive to existing treatments (such as meformin and/or sulfonylurea) to control hyperglycemia in Type 2 diabetic patients. An injectable synthetic form of Ex-4 (Byetta® (exenatide) sold by Amylin Pharmaceuticals, Inc.) has been recently approved for use in treating Type 2 diabetes as an adjunctive therapy to improve blood sugar control.

A study recently showed that Ex-4, along with anti-lymphocyte serum (ALS), reversed hyperglycemia in previously overt diabetic NOD (Non-Obese Diabetic) mice. In this study, GLP-1 alone showed no effect to hyperglycemia in NOD mice, indicating that controlling auto-activated lymphocytes by ALS was required to achieve remission of euglycemia. However, ALS is a potent immunosuppressant that causes general dysfunction in all types of lymphocytes. Long-term use of ALS has been known to lead to the risk of tumorigenesis and other severe infectious diseases due to general immune deficiency. Therefore, ALS and other immunosuppressant drugs have not been shown to be clinically useful in treating diabetes.

Accordingly, there remains a need for more effective pharmaceutical compositions and methods that utilize immunomodulating agents alone as monotherapy or in combination with a β-cell growth and/or differentiating factor to restore normal β-cell mass and/or function in subjects suffering from diabetes.

SUMMARY OF THE INVENTION

Now it has been surprisingly found that administration of (1) a biological/immune response modifier (immunomodulating) or anti-inflammatory agent (e.g., small molecule, antibody, peptide or gene therapy reagent) that effectively blocks autoimmune response or cytokine formation in a mammal (e.g., Lisofylline (LSF) and structurally related LSF analogs, as further described below), alone or in combination with (2) any compound or agent (e.g., small molecule or peptide) (e.g., Ex-4, Byetta®) that facilitates growth and/or differentiation of pancreatic β-cells or any insulin producing cell is useful for restoring normal β-cell mass and/or function; preventing the development of, or reversing, Type 1 diabetes, Latent Autoimmune Diabetes of Adults (LADA), and/or Type 2 diabetes; and increasing the number of functional insulin producing cells in an individual in need thereof as compared with previous pharmaceutical compositions and methods.

In one aspect, the present invention provides for the use of compounds or agents that can block cytokine signaling or formation and thereby prevent autoimmune damage to regenerated/emerging new insulin producing cells. Without using an agent to block the autoimmune process, β-cell differentiation and/or growth promoting agents will not be clinically effective because simultaneous regeneration of β-cells and prevention of autoimmune reactions would not be realized. This result is wholly unexpected.

In a preferred embodiment, the present invention provides a method for the prevention and treatment (including reversal and cure) of mammals (including humans and animals) suffering from diseases or conditions caused by, or associated with, diabetes mellitus (Type 1, LADA and Type 2), hyperglycemia, dyslipidemia, hyperlipidemia, hypercholesterolemia, hypertriglyceridemia, hyperinsulinemia, diabetic complications, glucose intolerance, obesity or the like. The method of the present invention comprises administering to a mammal, e.g., a human patient or animal, a preventative- or therapeutically-effective amount of a pharmaceutical composition comprising, in admixture with a pharmaceutically acceptable carrier, diluent, excipient, adjuvant or vehicle: (1) a biological/immune response modifier (immunomodulating) or anti-inflammatory agent (e.g., small molecule, antibody, peptide or gene therapy reagent) that effectively blocks autoimmune response in a mammal by inhibiting the activity or expression of inflammatory cytokines such as, for example, IL-12, IL-23 or IL-27, or STAT-4 and (2) any compound or agent (small molecule or peptide) that facilitates growth and/or differentiation of pancreatic β-cells or any insulin producing cell, either alone or in admixture with a diluent or in the form of a medicament.

In another preferred embodiment, there is also provided a pharmaceutical composition useful in the treatment of Type I diabetes, LADA, and Type 2 diabetes, which comprises (1) a therapeutically-effective amount of a biological/immune response modifier or anti-inflammatory agent and (2) a therapeutically-effective amount any compound or agent (small molecule or peptide) that facilitates growth and/or differentiation of pancreatic β-cells or any insulin producing cell, as described herein, in admixture with a pharmaceutically acceptable carrier, diluent, excipient, adjuvant or vehicle.

It is believed that inhibiting IL-12 overproduction, or inhibiting the production of cytokines such as IL-23 and IL-27 which promote STAT-4 activation and autoimmune disorders such as Type 1 diabetes and LADA development is believed to be a viable approach. For example, overproduction of inflammatory cytokines such as IL-6, IL-1, beta interferon gamma, TNF-α, etc. and the resultant excessive Th1 type responses can be suppressed by modulating IL-12, IL-23 and/or IL-27 production. Therefore, compounds (e.g., small molecule, antibody, peptide or gene therapy reagent) that down-regulate IL-12, IL-23 and/or IL-27 production can be used as biological response modifiers (immunomodulating agents) that block or inhibit inflammatory responses, inactivate STAT-4, reduce the gene expression of DPP-IV or otherwise increase the endogenous stability and levels of incretin hormones, such as GLP-1, without the deleterious side effects experienced with immunosuppressants.

Preferred biological/immune response modifying (immunomodulating) or anti-inflammatory compounds or agents include, without limitation, members of the group consisting of: Lisofylline (LSF) and the LSF analogs described in W0/00/61583 (corresponding to U.S. Pat. No. 6,774,130 (the entire disclosure of which is incorporated herein by reference) or any other small molecule or peptide or method capable of blocking interleukin 12, interleukin 23 or activation and/or expression of STAT-4, as further described below.

LSF (1-(5-R-hydroxyhexyl)-3,7-dimethylxanthine) is a synthetic, modified xanthine based compound have the following structural formula:

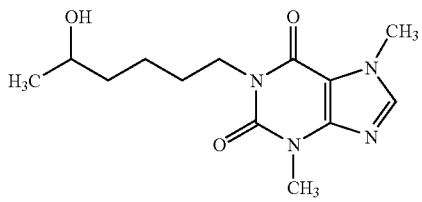

Without wishing to be bound by any theory of operation or mode of action, LSF and the LSF analogs described below exhibit anti-inflammatory function by reducing inflammatory cytokine production or downstream effects (including, without limitation, IL-12, IL-23, IL-27, TNF-α, IFN-γ, IL-6 and IL-1β), selectively suppressing neutrophil and leukocyte adhesion and phagocytic activity, and decreasing neutrophil migration and degranulation during sepsis. More significantly, LSF allows retention of beta-cell insulin secretory function after inflammatory cytokine insult and regulates immune cellular function to prevent autoimmunity. In addition, LSF also exhibits the ability to ameliorate hemorrhage-induced tissue injury and to preserve tissue function during decreased blood flow or in poorly ventilated conditions. LSF also inhibits phosphatidic acid formation to prevent oxidant-mediated capillary leak, thus reducing capillary barrier damage caused by oxidative stress. All of these characteristics render LSF and the LSF analogs described below capable of improving biological function and reducing autoimmune damage in β-cells. LSF is also useful as monotherapy for the treatment of Type 2 diabetes and its associated complications due to an ability to enhance the in vivo action of GLP-1. Moreover, LSF is useful in conjunction with any compound or agent (small molecule, peptide, etc.) that facilitates growth and/or differentiation of pancreatic β-cells or any insulin producing cell, in accordance with the features of the present invention. Because immunosuppressant therapy, including ALS, may not be suitable for a long-term use to treat Type 1 diabetes, LSF and its analogs represent a new class of immunomodulatory compounds that are capable of regulating cellular functions but retain host immune competence. Combining the effectiveness of β-cell regeneration by Ex-4 and autoimmune prevention by LSF may protect regenerated β-cells from autoimmune destruction while maintaining patient immunological competency.

The pharmaceutical compositions useful in the present invention may conveniently be provided, or is otherwise envisioned in the form of formulations suitable for parenteral (including intravenous, intramuscular and subcutaneous) nasal, oral administration or pulmonary via a inhalation device. In some cases, it will be convenient to provide a biological/immune response modifier or anti-inflammatory agent, as described herein, and any compound or agent (small molecule or peptide) that facilitates growth and/or differentiation of pancreatic β-cells or any insulin producing cell, each in a single composition or solution for administration together. A suitable administration format may best be determined by a medical practitioner for each patient individually. Suitable pharmaceutically acceptable carriers and their formulation are described in standard formulation treatises, e.g., Remington's Pharmaceutial Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1998).

Preferred compounds or agents that may be used in accordance with the principles of the present invention for inducing pancreatic β-cell or insulin producing cell growth and/or differentiation include, but are not limited to, members of the group consisting of: glucagon-like peptide-1 (GLP-1) and long-acting, DPP-IV-resistant GLP-1 analogs thereof, GLP-1 receptor agonists, gastric inhibitory polypeptide (GIP) and analogs thereof (e.g., which are disclosed in U.S. Patent Publication No. 20050233969), dipeptidyl peptidase IV (DPP-IV) inhibitors, insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, aldose reductase inhibitors, advanced glycation end products production inhibitors, glycogen synthase kinase-3 inhibitors, glycogen phosphorylase inhibitors, antilipemic agents, anorexic agents, lipase inhibitors, antihypertensive agents, peripheral circulation improving agents, antioxidants, diabetic neuropathy therapeutic agents, and the like.

Accordingly, the present invention provides use of the pharmaceutical compositions and agents described herein in conjunction with (1) methods for restoring β-cell mass and function in an individual in need thereof; (2) methods for preventing the development of, or reversing, Type 1 diabetes in an individual in need thereof; (3) methods for preventing the development of, or reversing, latent autoimmune diabetes of adults (LADA) in an individual in need thereof; and (4) methods for treating Type 2 diabetes by increasing the number of functional insulin producing cells (e.g., β-cells) in an individual in need thereof.

The above compounds and agents used in the pharmaceutical composition of the present invention may be purchased from conventional sources, may be readily isolated from and purified (isolated) from natural sources or may be synthesized using conventional techniques known to the skilled artisan using readily available starting materials.

Other technical features and advantages of the present invention will be set forth, in part, in the description that follows, or may be learned from practicing or using the present invention. The advantages of the present invention may be realized and attained by means of technical features described below and pointed out in the appended claims. It is to be understood that the foregoing general description and the following detailed description are merely exemplary and explanatory and should not to be viewed as being restrictive of the invention, as claimed.

BRIEF DESCRIPTION OF THE DRAWINGS

The accompanying drawings, which are incorporated in, and constitute a part of the specification, illustrate or exemplify embodiments of the present invention and, together with the description, serve to explain the principles and features of the present invention.

DESCRIPTION OF PREFERRED EMBODIMENTS

Figure 1:
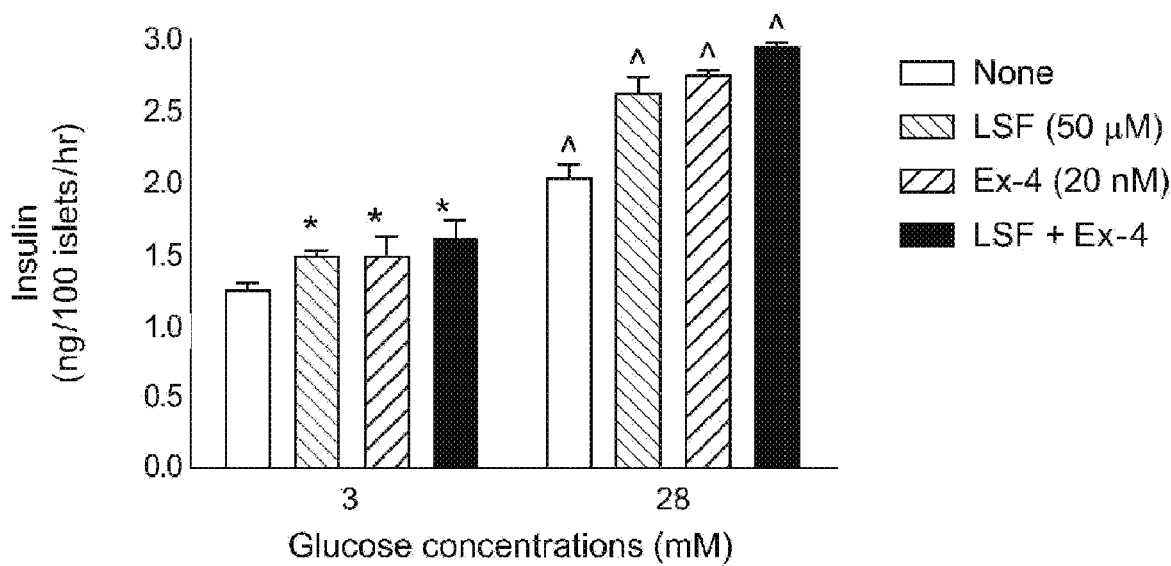
FIG. 1 depicts the amount of insulin in the supernate sample as determined by EIA after one-hour incubation with each of 3 mM and subsequent 28 mM glucose medium.

All patents, patent applications and literatures cited or referenced in this description are incorporated herein by reference in their entirety. In the case of inconsistencies, the present disclosure, including definitions, will control.

The pharmaceutical compositions and methods of the present invention comprise the combined use of: (1) a biological/immune response modifier or anti-inflammatory agent (e.g., small molecule, antibody, peptide or gene therapy reagent) that effectively blocks comprising a biological response modifier and a β-cell growth factor in admixture with a pharmaceutically acceptable carrier, adjuvant or vehicle, wherein the pharmaceutical composition blocks or prevents the autoimmune response in a mammal by inhibiting the activity or expression of cytokines such as interleukins 12, 23 or 27, or members of the family of Signal Transducers and Activators of Transcription (STAT), preferably STAT-4, which are believed to be regulators of T cell differentiation involved in immune responses, and (2) any compound or agent (small molecule or peptide) that induces growth and/or differentiation of pancreatic β-cells or any insulin producing cell.

Preferred agents that could be used to induce pancreatic β-cell or insulin producing cell growth and/or differentiation include, but are not limited to, members of the group consisting of:

glucagon-like peptide 1 (GLP-1);
long-acting, DPP-IV-resistant GLP-1 analogs thereof, including, without limitation, members of the group consisting of Exendin-4 (Ex-4), Exenatide (Byetta®, Amylin Pharmaceuticals), Exenatide LAR and related analogs disclosed in U.S. Pat. No. 5,424,286, U.S. Pat. No. 6,858,576, U.S. Pat. No. 6,872,700, U.S. Pat. No. 6,902,744, and U.S. Pat. No. 6,956,026 (the entire disclosures of which are incorporated herein by reference), Liraglutide (a.k.a., NN2211 or Arg(34)Lys(26)-(N-epsilon-(gamma-Glu(N-alpha-hexadecanoyl))-GLP-1 (7-37)) (Novo Nordisk), CJC-1131 (Conjuchem Inc.), Albugon (Human Genome Sciences), LY-548806 (Eli Lilly & Co), and the like;
inhibitors of GLP-1 degradation (a.k.a., DPP-IV inhibitors), which may be orally administered drugs that improve glycemic control by preventing DPP-IV degradation of GLP-1 and GIP and increasing incretin hormone levels to restore beta cell mass or function, including, without limitation, members of the group consisting of Sitagliptin (a.k.a. MK-0431, Merck), Vildagliptin (a.k.a. LAF-237) and NVP DPP728 (both of Novartis), Saxagliptin (Bristol Myers Squibb), P32/98 (Probiodrug) and FE 999011 (a.k.a. [(2S)-1-([2'S]-2'-amino-3', 3' dimethyl-butanoyl)-pyrrolidine-2-carbonitrile] developed by Ferring Research Institute), PHX1149 (Phenomix), and the like;
gastric inhibitory polypeptide (GIP) and analogs thereof (e.g., which are disclosed in U.S. Patent Publication No. 20050233969),
peptides such as gastrin and/or epidermal growth factor 1, including islet neogenesis therapy (Transition Therapeutics),
insulin like growth factor 1 or 2;
Parathyroid hormone related peptide (PTHrP) and
Hepatocyte growth factor or islet neogenesis associated protein (INGAP).

Other preferred methods of inducing β-cell differentiation or growth include, without limitation, providing one or any combination of transcription factors shown to be important for insulin gene transcription or β-cell growth or development, including, without limitation, members of the group consisting of Neurogen 3, PDX-1, NKX6.1 and the like.

Other preferred agents that induce pancreatic β-cell or insulin producing cell growth and/or differentiation include, but are not limited to, members of the group consisting of: histone deacetylose inhibitors (HDAC) such as NVP-LAQ824, TrichostatinA-0, hydroxamate, suberanihohydroxamic hydroxamic acid or cyclic tetrapeptides, apicidin and trapoxin as well as synthetic inhibitors, including CG1521 and others, scriptide and analogs. Other HDAC inhibitors include: oxamflatin, pyroxamide, propenamides, chlamydocin, diheteropeptin, WF-3136, Cyl-1 and Cyl-2, FR 901228, cyclic-hydroxamic-acid-containing peptides, MS-275, CI-994 and depudecin.

In another preferred embodiment, the present invention involves the use of inventive pharmaceutical composition comprising an autoimmune blocker and a β-cell growth or differentiating agent to create or grow insulin producing cells in a test tube to be transplanted in patients by any acceptable procedure to prevent, treat or reverse Type 1 diabetes or Type 2 diabetes. In addition, this combined therapeutic approach can be given to a human to restore beta (insulin producing) cells in the body to prevent, treat or reverse Type 1 diabetes, LADA or Type 2 diabetes. Accordingly, in another preferred embodiment, the present invention provides a method for improving the outcome or success of cellular (islet cell, isolated β-cells, genetically engineered or induced (e.g., via transcription factors) β-cells) transplantation in a mammal to reverse Type 1 diabetes, LADA and Type 2 diabetes, comprising administering to the mammal (or cells to be transplanted) an effective amount of a pharmaceutical composition of the present invention.

Preferred LSF analogs include, without limitation, compounds, pharmaceutically acceptable derivatives (e.g., racemic mixtures, resolved enantiomers, diastereomers, tautomers, salts and solvates thereof) or prodrugs thereof, having the following Formula I:

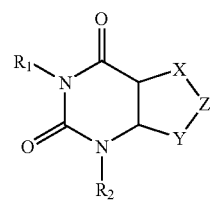

wherein:
the dashed lines, i.e., "————", in Formula I represent a single or double bond;
X, Y and Z are independently selected from a member of the group consisting of C(R3), N, N(R3) and S;
R1 is selected from a member of the group consisting of hydrogen, methyl, a substituted alkyl (as defined herein, which includes without limitation substituted C(5-9)alkyl), C(5-9)alkenyl, C(5-9)alkynyl, C(5-9)hydroxyalkyl, C(3-8) alkoxyl, C(5-9)alkoxyalkyl; and R2 and R3 are independently selected from a member of the group consisting of hydrogen, halo, oxo, C(1-20)alkyl, C(1-20)hydroxyalkyl, C(1-20)thioalkyl, C(1-20)alkylamino, C(1-20)alkylaminoalkyl, C(1-20)aminoalkyl, C(1-20)aminoalkoxyalkenyl, C(1-20)aminoalkoxyalkynyl, C(1-20)diaminoalkyl, C(1-20)triaminoalkyl, C(1-20)tetraminoalkyl, C(5-15)aminotrialkoxyamino, C(1-20)alkylamido, C(1-20)alkylamidoalkyl, C(1-20)amidoalkyl, C(1-20)acetamidoalkyl, C(1-20)alkenyl, C(1-20)alkynyl, C(3-8)alkoxyl, C(1-11)alkoxyalkyl, and C(1-20)dialkoxyalkyl.

R1 is optionally substituted with a member selected from the group consisting of N—OH, acylamino, cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, and phosphino, phosphinyl, phospho, phosphono and —NRaRb, wherein each of Ra and Rb may be the same or different and each is independently selected from the group consisting of hydrogen, optionally substituted alkyl, cycloalkyl, alkenyl, cycloalkenyl, alkynyl, aryl, heteroaryl and heterocyclic group.

Each R2 and R3 is optionally substituted with one or more members of the group consisting of hydroxyl, methyl, carboxyl, furyl, furfuryl, biotinyl, phenyl, naphthyl, amino group, amido group, carbamoyl group, cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, phosphino, phosphinyl, phospho, phosphono, N—OH, —Si(CH3)3 (a.k.a. SiMe3), C(1-3)alkyl, C(1-3)hydroxyalkyl, C(1-3)thioalkyl, C(1-3)alkylamino, benzyldihydrocinnamoyl group, benzoyldihydrocinnamido group, heterocyclic group and carbocyclic group.

The heterocyclic group or carbocyclic group is optionally substituted with one or more members of the group consisting of halo, hydroxyl, nitro (e.g., —NO2), SO2NH2, C(1-6)alkyl, C(1-6)haloalkyl, C(1-8)alkoxyl, C(1-11)alkoxyalkyl, C(1-6)alkylamino, and C(1-6)aminoalkyl.

Preferably, both X and Y are not N(R3) when Z is C(R3) and R3 is H or C(1-3)alkyl.

More preferably, R1 is not an ω-1 secondary alcohol substituted C(5-8)alkyl when both X and Y are N(R3), Z is C(R3) and R3 is H or C(1-3)alkyl.

In another preferred aspect of the present invention, R1 is an ω-1 secondary alcohol substituted C(5-8)alkyl when both X and Y are N(R3), Z is C(R3) and R3 is H or C(1-3)alkyl.

In a another aspect, more preferred LSF analog compounds include the following compounds, pharmaceutically acceptable derivatives (e.g., racemic mixtures, resolved enantiomers, diastereomers, tautomers, salts and solvates thereof) or prodrugs thereof, having the following Formula II:

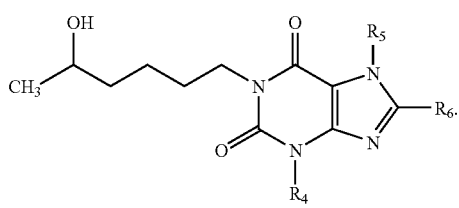

II wherein $R_4$, $R_5$ and $R_6$ are independently selected from a member of the group consisting of hydrogen, halo, oxo, $C_{(1-20)}$alkyl, $C_{(1-20)}$hydroxyalkyl, $C_{(1-20)}$thioalkyl, $C_{(1-20)}$alkylamino, $C_{(1-20)}$alkylaminoalkyl, $C_{(1-20)}$aminoalkyl, $C_{(1-20)}$aminoalkoxyalkenyl, $C_{(1-20)}$aminoalkoxyalkynyl, $C_{(1-20)}$diaminoalkyl, $C_{(1-20)}$triaminoalkyl, $C_{(1-20)}$tetraminoalkyl, $C_{(3-15)}$aminodialkoxyamino, $C_{(5-15)}$aminotrialkoxyamino, $C_{(1-20)}$alkylamido, $C_{(1-20)}$alkylamidoalkyl, $C_{(1-20)}$amidoalkyl, $C_{(1-20)}$acetamidoalkyl, $C_{(1-20)}$alkenyl, $C_{(1-20)}$alkynyl, $C_{(3-8)}$alkoxyl, $C_{(1-11)}$alkoxyalkyl, and $C_{(1-20)}$dialkoxyalkyl.

Each R4, R5 and R6 is optionally substituted with one or more members of the group consisting of hydroxyl, methyl, carboxyl, furyl, furfuryl, biotinyl, phenyl, naphthyl, amino group, amido group, carbamoyl group, cyano (e.g., NC—), cyanamido (e.g., NCNH—), cyanato (e.g., NCO—), sulfo, sulfonyl, sulfinyl, sulfhydryl (mercapto), sulfeno, sulfanilyl, sulfamyl, sulfamino, phosphino, phosphinyl, phospho, phosphono, N—OH, —Si(CH3)3, C(1-3)alkyl, C(1-3)hydroxyalkyl, C(1-3)thioalkyl, C(1-3)alkylamino, benzyldihydrocinnamoyl group, benzoyldihydrocinnamido group, heterocyclic group and carbocyclic group.

The heterocyclic group or carbocyclic group is optionally substituted with one or more members of the group consisting of halo, hydroxyl, nitro (e.g., —NO2), SO2NH2, C(1-6)alkyl, C(1-6)haloalkyl, C(1-8)alkoxyl, C(1-11)alkoxyalkyl, C(1-6)alkylamino, and C(1-6)aminoalkyl. In a preferred embodiment, each R4, R5 and R6 are not simultaneously methyl.

In a preferred embodiment, both R4 and R5 are not methyl when R6 is H.

In another preferred embodiment, R6 is not methyl when R4 is methylfuryl and R5 is H.

In a further preferred embodiment, R6 is not propyl or isopropyl when R4 is methyl and R5 is H.

In a still further preferred embodiment, R4 is not acetamidohexyl when R5 is methyl and R6 is H.

Preferred examples of R2, and R3 groups of Formula I and R4, R5 and R6 groups of Formula II include, without limitation, members selected from the group consisting of 1-adamantanemethyl, 1-phenylcyclopropyl, 1-phenylproply, 1-propenyl, 2-bromopropyl, 2-buten-2-yl, 2-butyl, 2-cyclohexylethyl, 2-cyclopentylethyl, 2-furyl, 2-hydroxyethyl, 2-hydroxystyryl, 2-methoxyethyl, 2-methoxystyryl, 2-methylbutyl, 2-methylcyclopropyl, 2-norboranemethyl, 2-phenylpropyl, 2-propenyl, 2-propyl, 2-thienyl, 2-trifluoromethylstyryl, 3,4,5-triethoxyphenyl, 3,4,5-trimethoxyphenyl, 3,4-dichlorobenzyl, 3,4-dichlorophenyl, 3,4-difluorophenyl, 3,4-difluorobenzyl, 3,4-dihydroxybenzyl, 3,4-dihydroxystyryl, 3,4-dimethoxybenzyl, 3,4-dimethoxyphenethyl, 3,4-dimethoxyphenyl, 3,4-dimethoxystyryl, 3,4-dimethylphenyl, 3,5-bis(trifluoromethyl)-benzyl, 3,5-dimethylphenyl, 3-bromo-4-methylphenyl, 3-bromobenzyl, 3-cyclohexylpropyl, 3-dimethylaminobutyl, 3-fluoro-4-methylphenyl, 3-fluorobenzyl, 3-hepten-3-yl, 3-hydroxy-n-butyl, 3-hydroxypropyl, 3-iodo-4-methylphenyl, 3-methoxy-4-methylphenyl, 3-methoxybenzyl, 3-methylbenzyl, 3-phenylpropyl, 3-trifluoromethylbenzyl, 4'-ethyl-4-biphenyl, 4-biphenyl, 4-bromobenzyl, 4-bromophenyl, 4-butylphenyl, 4-chloropentyl, 4-chlorostyryl, 4-ethoxybenzyl, 4-fluorobenzyl, 4-fluorophenyl, 4-hydroxyphenyl, 4-isobutylphenethyl, 4-isopropylphenyl, 4-methoxybenzyl, 4-methoxy-n-butyl, 4-methylbenzyl, 4-methylcyclohexanemethyl, 4-methylcyclohexyl, 4-phenylbenzyl, 4-t-butylcyclohexyl, 4-vinylphenyl, 5-hydroxyhexyl, alpha-methylstyryl, benzyl, cyclobutyl, cycloheptyl, cyclohexyl, cyclohexylmethyl, cyclopentyl, ethyl, hexyl, isobutyl, isopropyl, isovaleryl, m-anisyl, methyl, m-tolyl, n-butyl, n-propyl, p-anisyl, phenethyl, phenyl, propyl, p-tolyl, styryl, t-butyl, and the like.

Preferred R2, R3, R4, R5 and R6 groups include, without limitation, members selected from the group consisting of methyl, ethyl, oxo, isopropyl, n-propyl, isobutyl, n-butyl, t-butyl, 2-hydroxyethyl, 3-hydroxypropyl, 3-hydroxy-n-butyl, 2methoxyethyl, 4-methoxy-n-butyl, 5-hydroxyhexyl, 2-bromopropyl, 3-dimethylaminobutyl, 4-chloropentyl, methylamino, aminomethyl, methylphenyl, and the like.

In accordance with the present invention, the LSF compounds, LSF analogs, salts, solvates and prodrugs thereof, may exist in their tautomeric form (for example, as an amide or imino ether). All such tautomeric forms are contemplated herein as part of the present invention. Further, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds described herein as suitable for use in the present invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of compounds disclosed herein.

In accordance with the principles of the present invention, the LSF analogs described herein may contain one or more asymmetrically substituted carbon atoms and, thus, may occur as racemates and racemic mixtures, single enantiomers, diastereomeric mixtures and individual diastereomers. Each stereogenic carbon may be of the R or S configuration. Many geometric isomers of olefins, C—N double bonds, and the like can also be present in the compounds described herein, and all such stable isomers are contemplated in the present invention. It is well known in the art how to prepare optically active forms, such as by resolution of racemic forms or by synthesis from optically active starting materials. All chiral, diastereomeric, racemic forms and all geometric forms of a structure are intended to be encompassed within the present invention unless a specific stereochemistry or isomer form is specifically indicated.

The compounds of the present invention may be modified by appending appropriate functionalites to enhance selective biological properties. Such modifications are known in the art and include, without limitation, those which increase penetration into a given biological compartment (e.g., blood, lymphatic system, central nervous system), increase oral or intravenous bioavailability, increase solubility to allow administration by injection, alter metabolism, alter rate of excretion, etc.

Definitions

"Stereoisomer" or "Optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds described herein as suitable for use in the present invention which may give rise to stereoisomerism, the invention contemplates stereoisomers and mixtures thereof. The compounds described herein and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

"Enantiomers" means a pair of stereoisomers that are non-superimposable mirror images of each other.

"Diastereoisomers" or "Diastereomers" mean optical isomers which are not mirror images of each other.

"Racemic mixture" or "Racemate" mean a mixture containing equal parts of individual enantiomers.

"Non-Racemic Mixture" means a mixture containing unequal parts of individual enantiomers.

"Stable compound", as used herein, is a compound that is sufficiently robust to survive isolation to a useful degree of purity from a reaction mixture, and formulation into an efficacious therapeutic agent, i.e., possesses stability that is sufficient to allow manufacture and that maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week. "Metabolically stable compound" denotes a compound that remains bioavailable when orally ingested by a mammal.

"Substituted", as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a CH2 is substituted by a keto substituent (=O), then 2 hydrogens on the atom are replaced. It should be noted that when a substituent is listed without indicating the atom via which such substituent is bonded, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I or II, as well as the R2, R3, R4, R5 and R6 groups substituted thereon, via any atom in such piperazinyl, piperidinyl, tetrazolyl group. Combinations of substituents and/or variables are permissible only if such combinations result in stable compounds. Further, when more than one position in a given structure may be substituted with a substituent selected from a specified group, the substituents may be either the same or different at every position. Typically, when a structure may be optionally substituted, 0-15 substitutions are preferred, 0-5 substitutions are more preferred, and 0-1 substitution is most preferred.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Acyl" denotes a radical provided by the residue after removal of hydroxyl from an organic acid. Examples of such acyl radicals include, without limitation, alkanoyl and aroyl radicals. Examples of such lower alkanoyl radicals include, without limitation, formyl, acetyl, propionyl, butyryl, isobutyryl, valeryl, isovaleryl, pivaloyl, hexanoyl, trifluoroacetyl.

"Acylamino" denotes an N-substituted amide, i.e., RC(O)—NH and RC(O)—NR'—. A non-limiting example is acetamido.

"Acyloxy" means 1 to about 4 carbon atoms. Preferred examples include, without limitation, alkanoyloxy, benzoyloxy and the like.

"Alkyl" or "lower alkyl" is intended to include both branched and straight-chain saturated aliphatic hydrocarbon radicals/groups having the specified number of carbon atoms. In particular, "alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

"Substituted alkyl" refers to an alkyl group as defined above having from 1 to 5 substituents selected, without limitation, from the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxy, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-aryl, —SO-heteroaryl, —SO2-alkyl, —SO2-aryl, —SO2-heteroaryl, and —NRaRb, wherein Ra and Rb may be the same or different and are chosen from hydrogen, optionally substituted alkyl, cycloalkyl, alkenyl, cycloalkenyl, alkynyl, aryl, heteroaryl and heterocyclic group.

"Alkylamino" denotes amino groups which have been substituted with one or two alkyl radicals. Preferred are "lower N-alkylamino" radicals having alkyl portions having 1 to 6 carbon atoms. Preferred lower alkylamino may be mono or dialkylamino such as N-methylamino, N-ethylamino, N,N-dimethylamino, N,N-diethylamino or the like.

"Alkylaminoalkyl" embraces radicals having one or more alkyl radicals attached to an aminoalkyl radical.

"Alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above.

"Alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include, without limitation, substituted or unsubstituted methylcarbonyl, ethylcarbonyl, phenylcarbonyl and benzylcarbonyl.

"Alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include, without limitation, methylsulfinyl, ethylsulfinyl, butylsulfinyl and hexylsulfinyl.

"Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include, without limitation, methylsulfonyl, ethylsulonyl and propylsulfonyl. The "alkylsulfonyl" radicals may be further substituted with one or more halo atoms, such as fluoro, chloro or bromo, to provide haloalkylsulfonyl radicals.

"Alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

"Alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include, without limitation, methylthiomethyl.

"Alkylene" refers to a diradical of a branched or unbranched saturated hydrocarbon chain, preferably having from 1 to 40 carbon atoms, more preferably 1 to 10 carbon atoms, even more preferably 1 to 6 carbon atoms. This term is exemplified by groups such as methylene (—CH2-), ethylene (—CH2CH2-), the propylene isomers (e.g. —CH2CH2CH2- and —CH(CH3)CH2-), and the like.

"Substituted alkylene" refers to: (1) an alkylene group as defined above having from 1 to 5 substituents selected from a member of the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxy, oxyacylamino, azido, cyano, halogen, hydroxyl, keto, thioketo, carboxyl, carboxylalkyl, thiol, thioalkoxyl, substituted thioalkoxyl, aryl, aryloxyl, thioaryloxyl, heteroaryl, heteroaryloxyl, thioheteroaryloxyl, heterocyclic, heterocyclooxyl, thioheterocyclooxyl, nitro, and —NRaRb, wherein Ra and Rb may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include, without limitation, those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group; (2) an alkylene group as defined above that is interrupted by 1-20 atoms independently chosen from oxygen, sulfur and NRa, where Ra is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or (3) an alkylene group as defined above that has both from 1 to 5 substituents as defined above and is also interrupted by 1 to 20 atoms as defined above. Examples of substituted alkylenes are chloromethylene (—CH(C1)-, aminoethylene (—CH(NH2)CH2-), 2-carboxypropylene isomers (—CH2CH(CO2H)CH2-), ethoxyethyl (—CH2CH$_2$O—CH2CH2-), ethylmethylaminoethyl (—CH2CH2N(CH3)CH2CH2-), 1-ethoxy-2-(2-ethoxyethoxy)ethane (—CH2CH$_2$O—CH2CH2-OCH2CH2-OCH2CH2-), and the like.

"Alkynyl" is intended to include hydrocarbon chains of either a straight or branched configuration and one or more triple carbon-carbon bonds which may occur in any stable point along the chain, such as ethynyl, propynyl and the like. For example, alkynyl refers to an unsaturated acyclic hydrocarbon radical in so much as it contains one or more triple bonds, such radicals containing about 2 to about 40 carbon atoms, preferably having from about 2 to about 10 carbon atoms and more preferably having 2 to about 6 carbon atoms. Non-limiting examples of preferred alkynyl radicals include, ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

"Alicyclic hydrocarbon" means a aliphatic radical in a ring with 3 to about 10 carbon atoms, and preferably from 3 to about 6 carbon atoms. Examples of preferred alicyclic radicals include, without limitation, cyclopropyl, cyclopropylenyl, cyclobutyl, cyclopentyl, cyclohexyl, 2-cyclohexen-1-ylenyl, cyclohexenyl and the like.

"Alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include, without limitation, fluoromethoxy, chloromethoxy, trifluoromethoxy, trifluoromethoxy, fluoroethoxy and fluoropropoxy. Further, "alkoxycarbonyl" means a radical containing an alkoxy radical, as defined above, attached via an oxygen atom to a carbonyl radical. More preferred are "lower alkoxycarbonyl" radicals with alkyl portions having 1 to 6 carbons. Examples of such lower alkoxycarbonyl (ester) radicals include, without limitation, substituted or unsubstituted methoxycarbonyl, ethoxycarbonyl, propoxycarbonyl, butoxycarbonyl and hexyloxycarbonyl.

"Aminoalkyl" embraces alkyl radicals substituted with amino radicals. More preferred are "lower aminoalkyl" radicals. Examples of such radicals include, without limitation, aminomethyl, aminoethyl, and the like.

"Aminocarbonyl" denotes an amide group of the formula —C(=O)NH2.

"Aralkoxy" embraces aralkyl radicals attached through an oxygen atom to other radicals.

"Aralkoxyalkyl" embraces aralkoxy radicals attached through an oxygen atom to an alkyl radical.

"Aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy.

"Aralkylamino" embraces aralkyl radicals attached through an nitrogen atom to other radicals.

"Aralkylthio" embraces aralkyl radicals attached to a sulfur atom.

"Aralkylthioalkyl" embraces aralkylthio radicals attached through a sulfur atom to an alkyl radical.

"Aromatic hydrocarbon radical" means 4 to about 16 carbon atoms, preferably 6 to about 12 carbon atoms, more preferably 6 to about 10 carbon atoms. Examples of preferred aromatic hydrocarbon radicals include, without limitation, phenyl, naphthyl, and the like.

"Aroyl" embraces aryl radicals with a carbonyl radical as defined above. Examples of aroyl include, without limitation, benzoyl, naphthoyl, and the like and the aryl in said aroyl may be additionally substituted.

"Arylamino" denotes amino groups which have been substituted with one or two aryl radicals, such as N-phenylamino. Arylamino radicals may be further substituted on the aryl ring portion of the radical.

"Aryloxyalkyl" embraces radicals having an aryl radical attached to an alkyl radical through a divalent oxygen atom.

"Arylthioalkyl" embraces radicals having an aryl radical attached to an alkyl radical through a divalent sulfur atom.

"Carbonyl", whether used alone or with other terms, such as "alkoxycarbonyl", denotes —(C=O)—.

"Carboxy" or "carboxyl", whether used alone or with other terms, such as "carboxyalkyl", denotes —CO2H.

"Carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include, without limitation, carboxymethyl, carboxyethyl and carboxypropyl.

"Cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include, without limitation, cyclobutenyl, cyclopentenyl and cyclohexenyl.

"Cycloalkyl" embraces saturated carbocyclic radicals having three to twelve carbon atoms. More preferred cycloalkyl radicals are "lower cycloalkyl" radicals having three to about eight carbon atoms. Examples of such radicals include, without limitation, cyclopropyl, cyclobutyl, cyclopentyl and cyclohexyl.

"Hydroxyalkyl" embraces linear or branched alkyl radicals having one to about twenty carbon atoms any one of which may be substituted with one or more hydroxyl radicals. Preferred hydroxyalkyl radicals are "lower hydroxyalkyl" radicals having one to six carbon atoms and one or more hydroxyl radicals. Non-limiting examples of such radicals include hydroxymethyl, hydroxyethyl, hydroxypropyl, hydroxybutyl and hydroxyhexyl.

"Sulfamyl", "aminosulfonyl" and "sulfonamidyl" denote NH2O2S—.

"Sulfonyl", whether used alone or linked to other terms such as alkylsulfonyl, denotes respectively divalent radicals —SO2—.

"Alkenyl" is intended to include hydrocarbon chains of either a straight or branched configuration and one or more unsaturated carbon-carbon bonds which may occur in any stable point along the chain. For example, alkenyl refers to an unsaturated acyclic hydrocarbon radical in so much as it contains at least one double bond. Such radicals containing from about 2 to about 40 carbon atoms, preferably from about 2 to about 10 carbon atoms and more preferably about 2 to about 6 carbon atoms. Non-limiting examples of preferred alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like "Alkoxyl" represents an alkyl group of indicated number of carbon atoms attached through an oxygen bridge. "Alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include, without limitation, methoxy, ethoxy, propoxy, butoxy and tert-butoxy.

"Aryl" refers to an unsaturated aromatic carbocyclic group of from 6 to 20 carbon atoms having a single ring (e.g., phenyl) or multiple condensed (fused) rings (e.g., naphthyl or anthryl). "aryl" embraces aromatic radicals such as phenyl, naphthyl, tetrahydronaphthyl, indane and biphenyl. Unless otherwise constrained by the definition for the aryl substituent, such aryl groups can optionally be substituted with from 1 to 5 substituents selected from a member of the group consisting of acyloxyl, hydroxyl, thiol, acyl, alkyl, alkoxyl, alkenyl, alkynyl, cycloalkyl, cycloalkenyl, substituted alkyl, substituted alkoxyl, substituted alkenyl, substituted alkynyl, substituted cycloalkyl, substituted cycloalkenyl, aminoacyl, acylamino, alkaryl, aryl, aryloxyl, azido, carboxyl, carboxylalkyl, cyano, halo, nitro, heteroaryl, heteroaryloxyl, heterocyclic, heterocyclooxyl, aminoacyloxyl, oxyacylamino, thioalkoxyl, substituted thioalkoxyl, thioaryloxyl, thioheteroaryloxyl, —SO-alkyl, —SO-substituted alkyl, —SO-aryl, —SO-heteroaryl, —SO2-alkyl, —SO2-substituted alkyl, —SO2-aryl, —SO2-heteroaryl, trihalomethyl, NRaRb, wherein Ra and Rb may be the same or different and are chosen from hydrogen, optionally substituted alkyl, cycloalkyl, alkenyl, cycloalkenyl, alkynyl, aryl, heteroaryl and heterocyclic. Preferred aryl substituents include, without limitation, without limitation, alkyl, alkoxyl, halo, cyano, nitro, trihalomethyl, and thioalkoxy (i.e., —S-alkyl).

"N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include, without limitation, N-phenylaminomethyl and N-phenyl-N-methylaminomethyl.

"Carbocycle" or "carbocyclic group" is intended to mean any stable 3 to 7 membered monocyclic or bicyclic or 7 to 14 membered bicyclic or tricyclic or an up to 26 membered polycyclic carbon ring, any of which may be saturated, partially unsaturated, or aromatic.

"Substituted carbocycle" or "substituted carbocyclic group" refers to carbocyclic groups having from 1 to 5 substituents selected from a member of the group consisting of alkoxyl, substituted alkoxyl, cycloalkyl, cycloalkenyl, substituted cycloalkenyl, acyl, acylamino, acyloxyl, amino, aminoacyl, aminoacyloxyl, oxyaminoacyl, azido, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-substituted alkyl, —SO-aryl, —SO-heteroaryl, —SO2-alkyl, —SO2-substituted alkyl, —SO$_2$-aryl, —SO2-heteroaryl, and NRaRb, wherein Ra and Rb may be the same or different and are chosen from hydrogen, optionally substituted alkyl, cycloalkyl, alkenyl, cycloalkenyl, alkynyl, aryl, heteroaryl and heterocyclic. Preferred examples of carbocyclic groups include, without limitation, members selected from the group consisting of adamantyl, anthracenyl, benzamidyl, benzyl, bicyclo[2.2.1]heptanyl, bicyclo[2.2.1]hexanyl, bicyclo[2.2.2]octanyl, bicyclo[3.2.0]heptanyl, bicyclo[4.3.0]nonanyl, bicyclo[4.4.0]decanyl, biphenyl, biscyclooctyl, cyclobutanyl (cyclobutyl), cyclobutenyl, cycloheptanyl (cycloheptyl), cycloheptenyl, cyclohexanedionyl, cyclohexenyl, cyclohexyl, cyclooctanyl, cyclopentadienyl, cyclopentanedionyl, cyclopentenyl, cyclopentyl, cyclopropyl, decalinyl, 1,2-diphenylethanyl, indanyl, 1-indanonyl, indenyl, naphthyl, napthlalenyl, phenyl, resorcinolyl, stilbenyl, tetrahydronaphthyl (tetralin), tetralinyl, tetralonyl, tricyclododecanyl, and the like.

"Cycloalkyl" is intended to include saturated ring groups, including mono-, bi- or poly-cyclic ring systems, such as, without limitation, cyclopropyl, cyclobutyl, cyclopentyl, cyclohexyl, cycloheptyl, cyclooctyl, and adamantyl. "Bicycloalkyl" is intended to include saturated bicyclic ring groups such as, without limitation, [3.3.0]bicyclooctane, [4.3.0]bicyclononane, [4.4.0]bicyclodecane (decalin), [2.2.2]bicyclooctane, and so forth.

"Halo" or "halogen" as used herein refers to fluoro, chloro, bromo and iodo; and "counterion" is used to represent a small, negatively charged species such as chloride, bromide, hydroxide, acetate, sulfate and the like.

"Haloalkyl" is intended to include both branched and straight-chain saturated aliphatic hydrocarbon groups having the specified number of carbon atoms, substituted with 1 or more halogen. Haloalkyl embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Non-limiting examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

"Heterocycle" or "heterocyclic group" refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "heterocycle" or "heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom so long as the resulting compound is stable. Unless otherwise constrained by the definition for the heterocyclic substituent, such heterocyclic groups can be optionally substituted with 1 to 5, and preferably 1 to 3 substituents. Suitable, but non-limiting, examples of such substituents include members selected from the group consisting of alkoxyl, substituted alkoxyl, cycloalkyl, substituted cycloalkyl, cycloalkenyl, substituted cycloalkenyl, acyl, acylamino, acyloxyl, aminoacyl, aminoacyloxyl, oxyaminoacyl, cyano, halogen, hydroxyl, keto, thioketo, carboxyl, carboxylalkyl, thioaryloxyl, thioheteroaryloxyl, thioheterocyclooxyl, thiol, thioalkoxyl, substituted thioalkoxyl, aryl, aryloxyl, heteroaryl, heteroaryloxyl, heterocyclic, heterocyclooxyl, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, —SO, -heteroaryl, and NRaRb, wherein Ra and Rb may be the same or different and are chosen from hydrogen, optionally substituted alkyl, cycloalkyl, alkenyl, cycloalkenyl, alkynyl, aryl, heteroaryl and heterocyclic.

Preferred examples of such heterocyclic groups include, without limitation, acridinyl, acridonyl, adeninyl, alkylpyridinyl, alloxanyl, alloxazinyl, anthracenyl, anthranilyl, anthraquinonyl, anthrenyl, ascorbyl, azaazulenyl, azabenzanthracenyl, azabenzanthrenyl, azabenzonaphthenyl, azabenzophenanthrenyl, azachrysenyl, azacyclazinyl, azaindolyl, azanaphthacenyl, azanaphthalenyl, azaphenoxazinyl, azapinyl, azapurinyl, azapyrenyl, azatriphenylenyl, azepinyl, azetidinedionyl, azetidinonyl, azetidinyl, azinoindolyl, azinopyrrolyl, azinyl, aziridinonyl, aziridinyl, azirinyl, azocinyl, azoloazinyl, azolyl, barbituric acid, benzacridinyl, benzazapinyl, benzazinyl, benzimidazolethionyl, benzimidazolonyl, benzimidazolyl, benzisothiazolyi, benzisoxazolyl, benzocinnolinyl, benzodiazocinyl, benzodioxanyl, benzodioxanyl, benzodioxolyl, benzofuranyl (benzofuryl), benzofuroxanyl, benzonaphthyridinyl, benzopyranonyl (benzopyranyl), benzopyridazinyl, benzopyronyl, benzoquinolinyl, benzoquinolizinyl, benzothiadiazinyl, benzothiazepinyl, benzothiazinyl, benzothiazolyl, benzothiepinyl, benzothiophenyl, benzotriazepinonyl, benzotriazolyl, benzoxadizinyl, benzoxazinyl, benzoxazolinonyl, benzoxazolyl, benzylisoquinolinyl, beta-carbolinyl, biotinyl, bipyridinyl, butenolidyl, butyrolactonyl, caprolactamyl, carbazolyl, 4a H-carbazolyl, carbolinyl, catechinyl, chromanyl, chromenopyronyl, chromonopyranyl, chromylenyl, cinnolinyl, coumarinyl, coumaronyl, decahydroquinolinyl, decahydroquinolonyl, depsidinyl, diazaanthracenyl, diazaphenanthrenyl, diazepinyl, diazinyl, diaziridinonyl, diaziridinyl, diazirinyl, diazocinyl, dibenzazepinyl, dibenzofuranyl, dibenzothiophenyl, dibenzoxazepinyl, dichromylenyl, dihydrobenzimidazolyl, dihydrobenzothiazinyl, dihydrofuranyl, dihydroisocoumarinyl, dihydroisoquinolinyl, dihydrooxazolyl, dihydropyranyl, dihydropyridazinyl, dihydropyridinyl, dihydropyridonyl, dihydropyrimidinyl, dihydropyronyl, dihydrothiazinyl, dihydrothiopyranyl, dihydroxybenzenyl, dimethoxybenzenyl, dimethylxanthinyl, dioxadiazinyl, dioxanthylenyl, dioxanyl, dioxenyl, dioxepinyl, dioxetanyl, dioxinonyl, dioxinonyl, dioxiranyl, dioxolanyl, dioxolonyl, dioxolyl, dioxopiperazinyl, diprylenyl, dipyrimidopyrazinyl, dithiadazolyl, dithiazolyl, 2H,6H-1,5,2-dithiazinyl, dithietanyl, dithiolanyl, dithiolenyl, dithiolyl, enantholactamyl, episulfonyl, flavanyl, flavanyl, flavinyl, flavonyl, fluoranyl, fluorescienyl, furandionyl, furanochromanyl, furanonyl, furanoquinolinyl, furanyl (furyl), furazanyl, furfuryl, furopyranyl, furopyrimidinyl, furopyronyl, furoxanyl, glutarimidyl, glycocyamidinyl, guaninyl, heteroazulenyl, hexahydropyrazinoisoquinolinyl, hexahydropyridazinyl, homophthalimidyl, hydantoinyl, hydrofuranyl, hydrofuranonyl, hydroimidazolyl, hydroindolyl, hydropyranyl, hydropyrazinyl, hydropyrazolyl, hydropyridazinyl, hydropyridinyl, hydropyrimidinyl, hydropyrrolyl, hydroquinolinyl, hydrothiochromenyl, hydrothiophenyl, hydrotriazolyl, hydroxytrizinyl, imidazolethionyl, imidazolidinyl, imidazolinyl, imidazolonyl, imidazolyl, imidazoquinazolinyl, imidazothiazolyl, indazolebenzopyrazolyl, indazolyl, 1H-indazolyl, indolenyl, indolinyl, indolizidinyl, indolizinyl, indolonyl, indolyl, 3H-indolyl, indoxazenyl, inosinyl, isatinyl, isatogenyl, isoalloxazinyl, isobenzofurandionyl, isobenzofuranyl, isochromanyi, isoflavonyl, isoindolinyl (isoindolyl), isoindolobenzazepinyl, isoquinolinyl, isoquinuclidinyl, isothiazolyl, isoxazolidinyl, isoxazolinonyl, isoxazolinyl, isoxazolonyl, isoxazolyl, lactamyl, lactonyl, lumazinyl, maleimidyl, methylbenzamidyl, methylbenzoyleneureayl, methyldihydrouracilyl, methyldioxotetrahydropteridinyl, methylpurinyl, methylthyminyl, methylthyminyl, methyluracilyl, methylxanthinyl, monoazabenzonaphthenyl, morpholinyl (morpholino), naphthacenyl, naphthalenyl, naphthimidazolyl, naphthimidazopyridinedionyl, naphthindolizinedionyl, naphthodihydropyranyl, naphthofuranyl, naphthothiophenyl, naphthylpyridinyl, naphthyridinyl, octahydroisoquinolinyl, octylcarboxamidobenzenyl, oroticyl, oxadiazinyl, oxadiazolyl, oxathianyl, oxathiazinonyl, oxathietanyl, oxathiiranyl, oxathiolanyl, oxatriazolyl, oxazinonyl, oxaziranyl, oxaziridinyl, oxazolidinonyl, oxazolidinyl, oxazolidonyl, oxazolinonyl, oxazolinyl, oxazolonyl, oxazolopyrimidinyl, oxazolyl, oxepinyl, oxetananonyl, oxetanonyl, oxetanyl, oxindolyl, oxiranyl, oxolenyl, pentazinyl, pentazolyl, perhydroazolopyridinyl, perhydrocinnolinyl, perhydroindolyl, perhydropyrroloazinyl, perhydropyrrolooxazinyl, perhydropyrrolothiazinyl, perhydrothiazinonyl, perimidinyl, petrazinyl, phenanthraquinonyl, phenanthridinyl, phenanthrolinyl, phenarsazinyl, phenazinyl, phenothiazinyl, phenoxanthinyl, phenoxazinyl, phenoxazonyl, phthalazinyl, phthalideisoquinolinyl, phthalimidyl, phthalonyl, piperazindionyl, piperazinodionyl, piperazinyl, piperidinyl, piperidonyl, 4-piperidonyl, polyoxadiazolyl, polyquinoxalinyl, prolinyl, prylenyl, pteridinyl, pterinyl, purinyl, pyradinyl, pyranoazinyl, pyranoazolyl, pyranonyl, pyranopyradinyl, pyranopyrandionyl, pyranopyridinyl, pyranoquinolinyl, pyranyl, pyrazinyl, pyrazolidinyl, pyrazolidonyl, pyrazolinonyl, pyrazolinyl, pyrazolobenzodiazepinyl, pyrazolonyl, pyrazolopyridinyl, pyrazolopyrimidinyl, pyrazolotriazinyl, pyrazolyl, pyrenyl, pyridazinyl, pyridazonyl, pyridinethionyl, pyridinonaphthalenyl, pyridinopyridinyl, pyridocolinyl, pyridoindolyl, pyridopyrazinyl, pyridopyridinyl, pyridopyrimidinyl, pyridopyrrolyl, pyridoquinolinyl, pyridyl (pyridinyl), pyrimidinethionyl, pyrimidinyl, pyrimidionyl, pyrimidoazepinyl, pyrimidopteridinyl, pyronyl, pyrrocolinyl, pyrrolidinyl, 2-pyrrolidinyl, pyrrolinyl, pyrrolizidinyl, pyrrolizinyl, pyrrolobenzodiazepinyl, pyrrolodiazinyl, pyrrolonyl, pyrrolopyrimidinyl, pyrroloquinolonyl, pyrrolyl, 2H-pyrrolyl, quinacridonyl, quinazolidinyl, quinazolinonyl, quinazolinyl, quinolinyl, quinolizidinyl, quinolizinyl, 4H-quinolizinyl, quinolonyl, quinonyl, quinoxalinyl, quinuclidinyl, quinuclidinyl, rhodaminyl, spirocoumaranyl, succinimidyl, sulfolanyl, sulfolenyl, sultamyl, sultinyl, sultonyl, sydononyl, tetrahydrofuranyl, tetrahydroisoquinolinyl, tetrahydrooxazolyl, tetrahydropyranyl, tetrahydropyrazinyl, tetrahydropyridazinyl, tetrahydropyridinyl, tetrahydroquinolinyl, tetrahydroquinoxalinyl, tetrahydrothiapyranyl, tetrahydrothiazolyl, tetrahydrothiophenyl, tetrahydrothiopyranonyl, tetrahydrothiopyranyl, tetraoxanyl, tetrazepinyl, tetrazinyl, tetrazolyl, tetronyl, thiabenzenyl, thiachromanyl, thiadecalinyl, thiadiazinyl, 6H-1,2,5-thiadiazinyl, thiadiazolinyl, thiadiazolyl, thiadioxazinyl, thianaphthenyl, thianthrenyl, thiapyranyl, thiapyronyl, thiatriazinyl, thiatriazolyl, thiazepinyl, thiazetidinyl, thiazinyl, thiazindinyl, thiazolidinonyl, thiazolidinyl, thiazolinonyl, thiazolinyl, thiazolobenzimidazolyl, thiazolopyridinyl, thiazolyl, thienopryidinyl, thienopyrimidinyl, thienopyrrolyl, thienothiophenyl, thienyl, thiepinyl, thietanyl, thiiranyl, thiochromenyl, thiocoumarinyl, thiolanyl, thiolenyl, thiolyl, thiophenyl, thiopyranyl, thyminyl, triazaanthracenyl, triazepinonyl, triazepinyl, triazinoindolyl, triazinyl, triazolinedionyl, triazolinyl, triazolopyridinyl, triazolopyrimidinyl, triazolyl, trioxanyl, triphenodioxazinyl, triphenodithiazinyl, trithiadiazepinyl, trithianyl, trixolanyl, trizinyl, tropanyl, uracilyl, xanthenyl, xanthinyl, xanthonyl, xanthydrolyl, xylitolyl, and the like as well as N-alkoxy-nitrogen containing heterocycles. Preferred heterocyclic groups include, without limitation, members of the group consisting of acridinyl, aziridinyl, azocinyl, azepinyl, benzimidazolyl, benzodioxolanyl, benzofuranyl, benzothiophenyl, carbazole, 4a H-carbazole, chromanyl, chromenyl, cinnolinyl, decahydroquinolinyl, dioxoindolyl, furazanyl, furyl, furfuryl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthalenyl, naphthyridinyl, norbornanyl, norpinanyl, octahydroisoquinolinyl, oxazolidinyl, oxazolyl, oxiranyl, perimidinyl, phenanthridinyl, phenanthrolinyl, phenarsazinyl, phenazinyl, phenothiazinyl, phenoxathiinyl, phenoxazinyl, phenyl, phthalazinyl, piperazinyl, piperidinyl, 4-piperidonyl, piperidyl, pteridinyl, purinyl, pyranyl, pyrazinyl, pyrazolidinyl, pyrazolinyl, pyrazolyl, pyrenyl, pyridazinyl, pyridinyl, pyridyl, pyridyl, pyrimidinyl, pyrrolidinyl, 2-pyrrolidonyl, pyrrolonyl, pyrrolyl, 2H-pyrrolyl, quinazolinyl, 4H-quinolizinyl, quinolinyl, quinoxalinyl, quinuclidinyl, β-carbolinyl, tetrahydrofuranyl, tetrahydroisoquinolinyl, tetrahydroquinolinyl, tetrazolyl, 6H-1,2,5-thiadiazinyl, 2H-, 6H-1,5,2-dithiazinyl, thianthrenyl, thiazolyl, thienyl, thiophenyl, triazinyl, xanthenyl, xanthinyl, and the like.

"Pharmaceutically acceptable derivative" or "prodrug" means any pharmaceutically acceptable salt, ester, salt of an ester, or other derivative of a compound of the present invention which, upon administration to a recipient, is capable of providing (directly or indirectly) a compound of this invention. The term "prodrug", as employed herein, denotes a compound that is a drug precursor which, upon administration to a subject, undergoes chemical conversion by metabolic or chemical processes to yield a pharmaceutically active compound. Particularly favored derivatives and prodrugs are those that increase the bioavailability of the compounds of this invention when such compounds are administered to a mammal (e.g., by allowing an orally administered compound to be more readily absorbed into the blood) or that enhance delivery of the parent compound to a biological compartment (e.g., the brain or lymphatic system) relative to the parent species. Prodrugs are considered to be any covalently bonded carriers which release the active parent drug according to Formula I or II in vivo when such prodrug is administered to a mammalian subject. Preferred prodrugs include, without limitation, derivatives where a group that enhances aqueous solubility or active transport through the gut membrane is appended to the structure of Formula I or II. Prodrugs of the compounds of Formula I or II are prepared by modifying functional groups present in the compounds in such a way that the modifications are cleaved, either in routine manipulation or in vivo, to the parent compounds. Prodrugs include compounds of Formula I or II wherein hydroxyl, amino, sulfhydryl, or carboxyl groups are bonded to any group that, when administered to a mammalian subject, cleaves to form a free hydroxyl, amino, sulfhydryl, or carboxyl group, respectively. Examples of prodrugs include, but are not limited to, acetate, formate and benzoate derivatives of alcohol and amine functional groups in the compounds of Formula I or II, and the like. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference.

"Solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of preferred solvates include ethanolates, methanolates, and the like. "Hydrate" is a solvate wherein the solvent molecule is $H_2O$.

"Pharmaceutically acceptable salts" refer to derivatives of the disclosed compounds wherein the parent compound of Formula I or II is modified by making acid or base salts of the compound of Formula I or II. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds of Formula I or II include the conventional nontoxic salts or the quaternary ammonium salts of the compounds of Formula I or II formed, for example, from nontoxic inorganic or organic acids. For example, such conventional non-toxic salts include, without limitation, those derived from inorganic acids such as acetic, 2-acetoxybenzoic, adipic, alginic, ascorbic, aspartic, benzoic, benzenesulfonic, bisulfic, butyric, citric, camphoric, camphorsulfonic, cyclopentanepropionic, digluconic, dodecylsulfanilic, ethane disulfonic, ethanesulfonilic, fumaric, glucoheptanoic, glutamic, glycerophosphic, glycolic, hemisulfanoic, heptanoic, hexanoic, hydrochloric, hydrobromic, hydroiodic, 2-hydroxyethanesulfonoic, hydroxymaleic, isethionic, lactic, malic, maleic, methanesulfonic, 2-naphthalenesulfonilic, nicotinic, nitric, oxalic, palmic, pamoic, pectinic, persulfanilic, phenylacetic, phosphoric, propionic, pivalic, propionate, salicylic, succinic, stearic, sulfuric, sulfamic, sulfanilic, tartaric, thiocyanic, toluenesulfonic, tosylic, undecanoatehydrochloric, and the like. The pharmaceutically acceptable salts of the present invention can be synthesized from the compounds of Formula I or II which contain a basic or acidic moiety by conventional chemical methods, for example, by reacting the free base or acid with stoichiometric amounts of the appropriate base or acid, respectively, in water or in an organic solvent, or in a mixture of the two (nonaqueous media like ether, ethyl acetate, ethanol, isopropanol, or acetonitrile are preferred) or by reacting the free base or acid with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, et al., the entire disclosure of which is incorporated herein by reference.

Further, exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

"Pharmaceutically effective" or "therapeutically effective" amount of a compound of the present invention is an amount that is sufficient to effect the desired therapeutic, ameliorative, inhibitory or preventative effect, as defined herein, when administered to a mammal in need of such treatment. The amount will vary depending upon the subject and disease condition being treated, the weight and age of the subject, the severity of the disease condition, the manner of administration and the like, which can be readily determined by one of skill in the art.

"Mammal" means humans and other mammalian animals.

"Treatment" refers to any treatment of a disease (e.g., diabetes mellitus) or condition in a mammal, particularly a human, and includes, without limitation: (i) preventing the disease or condition from occurring in a subject which may be predisposed to the condition but has not yet been diagnosed with the condition and, accordingly, the treatment constitutes prophylactic treatment for the pathologic condition; (ii) inhibiting the disease or condition, i.e., arresting its development; (iii) relieving the disease or condition, i.e., causing regression of the disease or condition; or (iv) relieving the symptoms resulting from the disease or condition, e.g., relieving an inflammatory response without addressing the underlining disease or condition.

The present invention also envisions the quaternization of any basic nitrogen-containing groups of the compounds disclosed herein. The basic nitrogen can be quaternized with any agents known to those of ordinary skill in the art including, without limitation, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

Without being bound by the above general structural descriptions/definitions, preferred compounds suitable as biological/immune response modifiers or anti-inflammatory agents that effectively block autoimmune response or cytokine formation in a mammal, include, but are not limited to the following compounds. It will be appreciated, as noted above, that where an R or S enantiomer is exemplified for each particular compound, the corresponding S or R enantiomer, respectively, is also intended even though it may not be specifically shown below.

More preferred compounds of the present invention having utility for inhibiting IL-12 signaling include without limitation, the following:

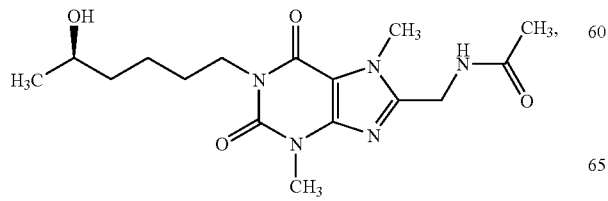

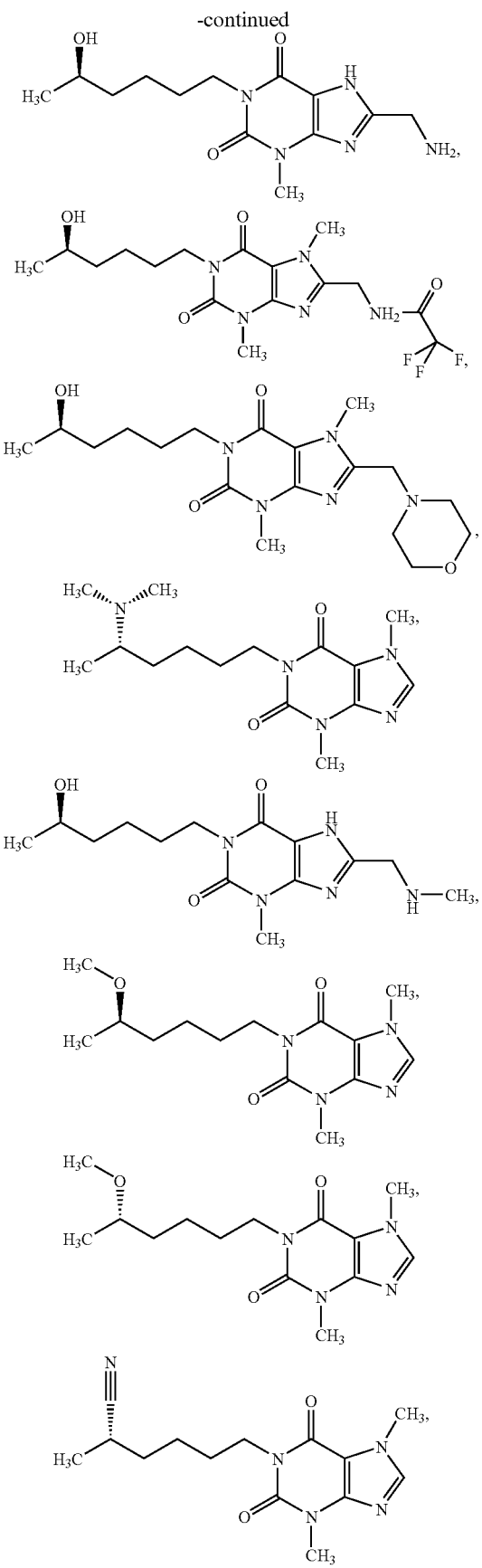

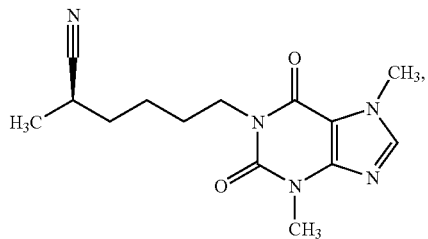
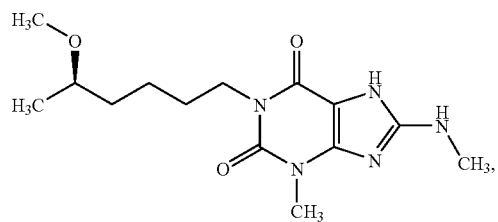
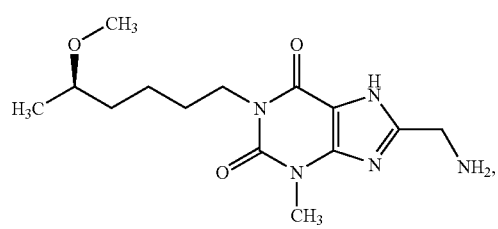
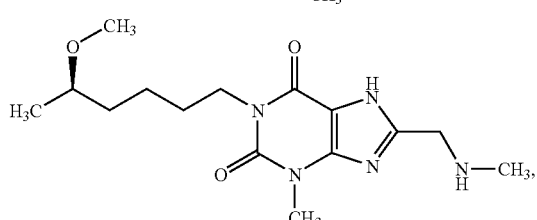
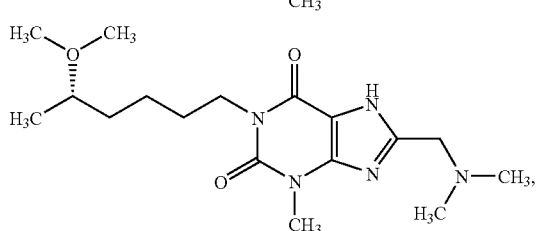
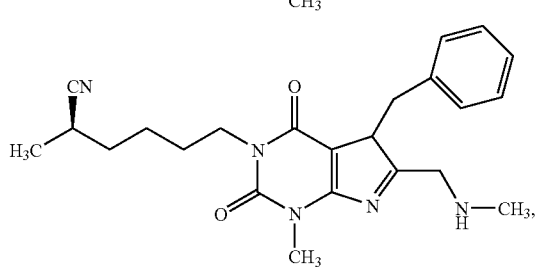
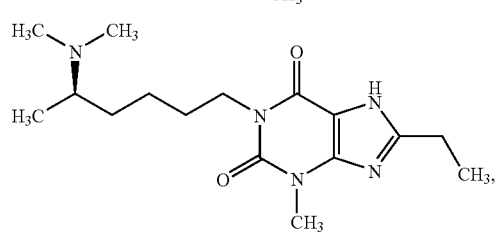
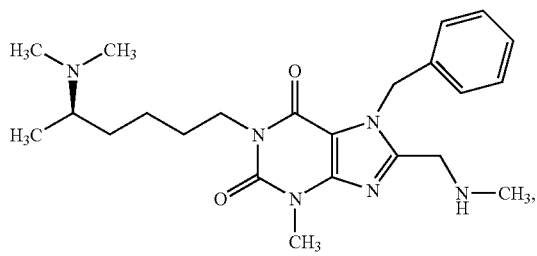
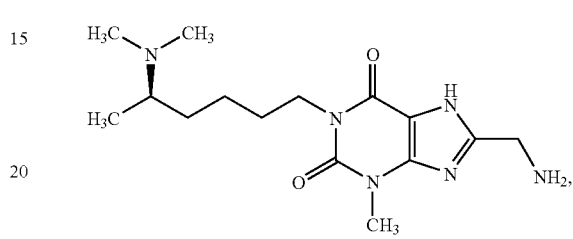
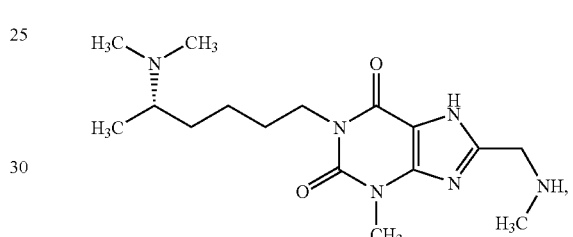
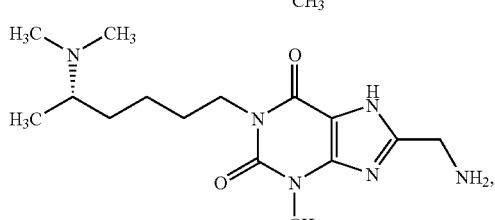
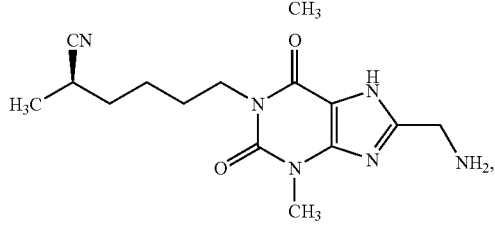
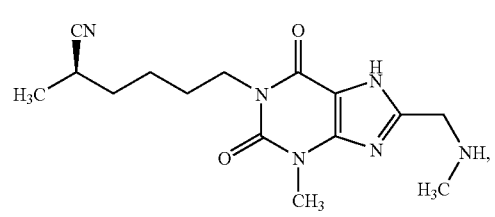
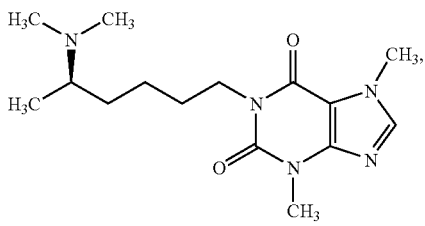

-continued

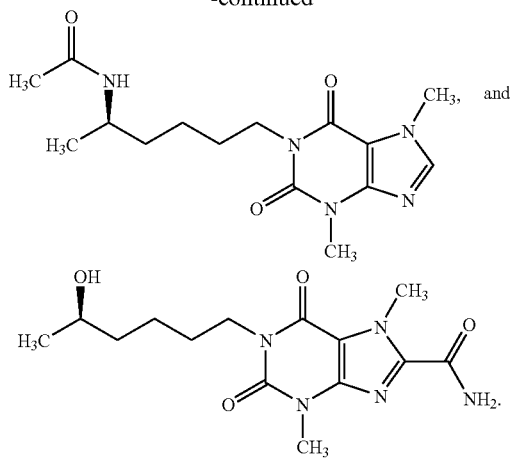

Further representative compounds of the present invention having utility as a biological/immune response modifier (immunomodulating) or anti-inflammatory agent in accordance with the present invention are set forth below in Table 1. The compounds in Table 1 have the following general structure of Formula II:

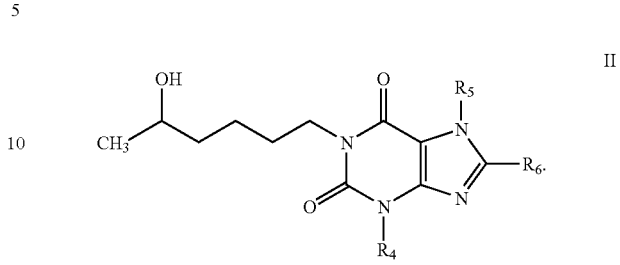

It is noted that in Table 1, "Me" represents "—CH3," and "Et" represents "—CH2CH3." In addition, although the below-exemplified moieties in Table 1 are representative of $R_4$, $R_5$ and $R_6$ in Formula II, it will be understood that the exemplified moieties, without being limited by the above description/definitions, are also representative of $R_2$ and $R_3$ in Formula I.

TABLE 1

| $R_4$ | $R_5$ | $R_6$ |
|---|---|---|
| Me | H | ![structure] —NH-CH2-(3-pyridyl) |
| Me | H | ![structure] —NH-CH2-(2-pyridyl) |
| Me | H | ![structure] —NH-CH2-CH(OH)-CH3 (R) |
| Me | H | ![structure] —NH-CH2-CH(OH)-CH3 (S) |
| Me | H | ![structure] —NH-CH2-(2-pyrrolidinyl) |
| Me | H | ![structure] —NH-CH2CH2CH2-(2-methylpiperidinyl) |
| Me | H | ![structure] —NH-CH2CH2-NH-(5-nitro-2-pyridyl) |

TABLE 1-continued
| R₄ | R₅ | R₆ |
|----|----|----|
| Me | H | 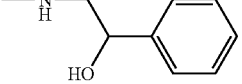 |
| Me | H | 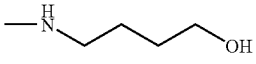 |
| Me | H | 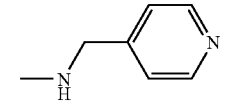 |
| Me | H | 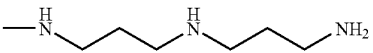 |
| Me | H | 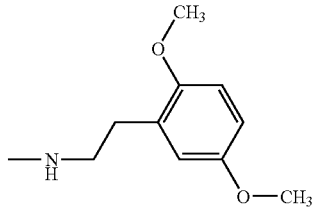 |
| Me | H | 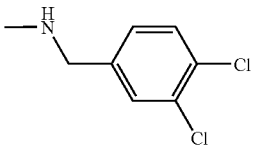 |
| Me | H | 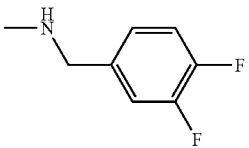 |
| Me | H | 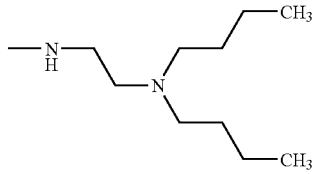 |
| Me | H | 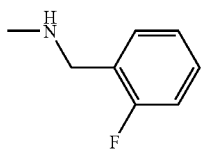 |
| Me | H | 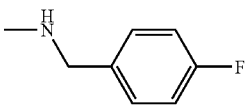 |
| Me | H | 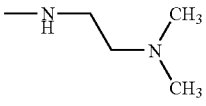 |
| Me | H | 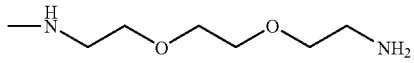 |

TABLE 1-continued
| R4 | R5 | R6 |
|----|----|----|
| Me | H | 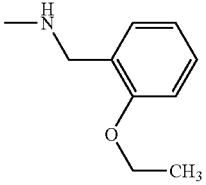 |
| Me | H | 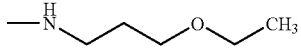 |
| Me | H | 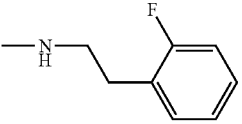 |
| Me | H | 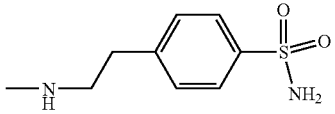 |
| Me | H | 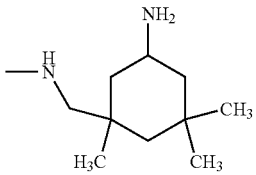 |
| Me | H | 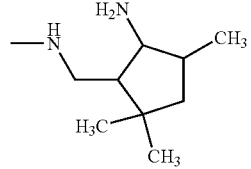 |
| Me | H | 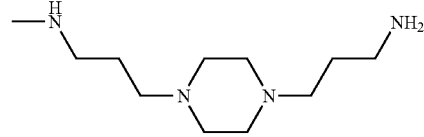 |
| Me | H | 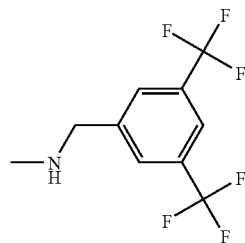 |
| Me | H | 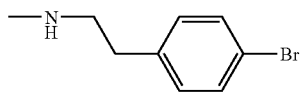 |
| Me | H | 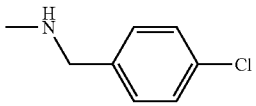 |

TABLE 1-continued
| R4 | R5 | R6 |
|---|---|---|
| Me | H | 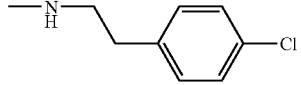 |
| Me | H | 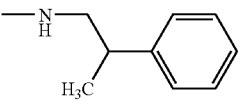 |
| Me | H | 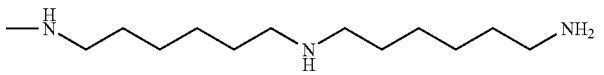 |
| Me | H | 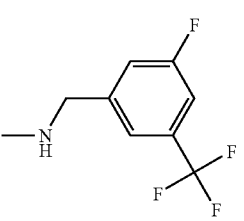 |
| Me | H | 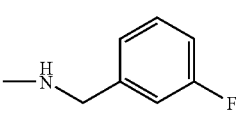 |
| Me | H | 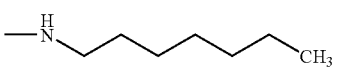 |
| Me | H | 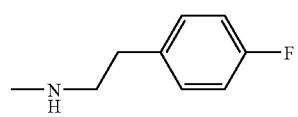 |
| Me | H | 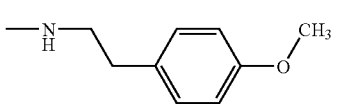 |
| Me | H | 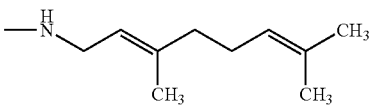 |
| Me | H | 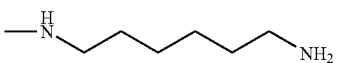 |
| Me | H | 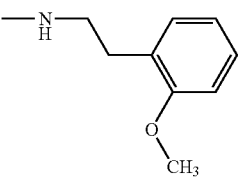 |
| Me | H | 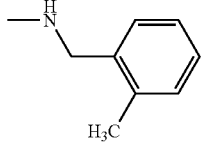 |

TABLE 1-continued
| R₄ | R₅ | R₆ |
|----|----|----|
| Me | H | 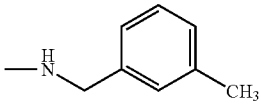 |
| Me | H | 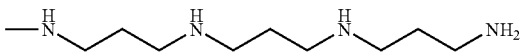 |
| Me | H | 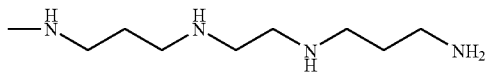 |
| Me | H | 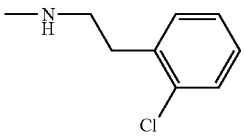 |
| Me | H | 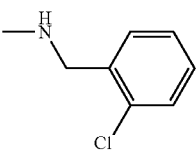 |
| Me | H | 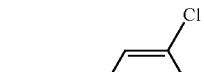 |
| Me | H | 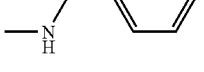 |
| Me | H | 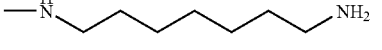 |
| Me | H | 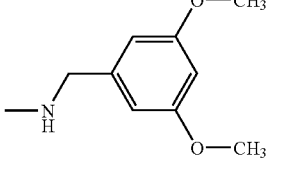 |
| Me | H | 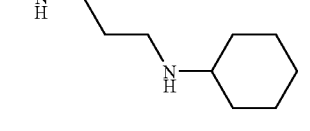 |
| Me | H | 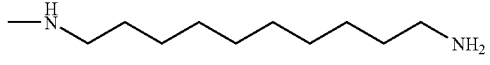 |
| Me | H | 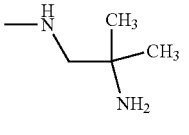 |
| Me | H | 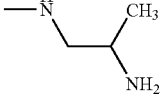 |

TABLE 1-continued
| R4 | R5 | R6 |
|---|---|---|
| Me | H | 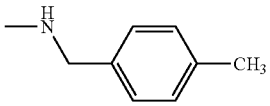 |
| Me | H | 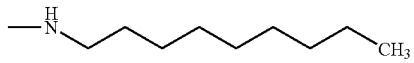 |
| Me | H | 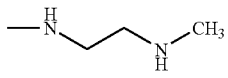 |
| Me | H | 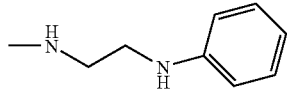 |
| Me | H | 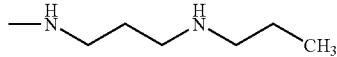 |
| Me | H | 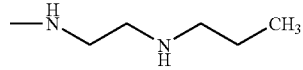 |
| Me | H | 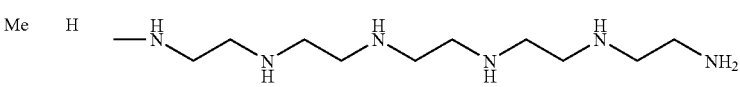 |
| Me | H | 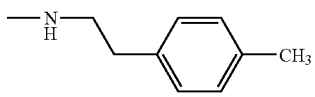 |
| Me | H | 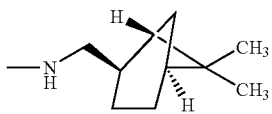 |
| Me | H | 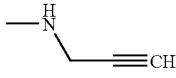 |
| Me | H | 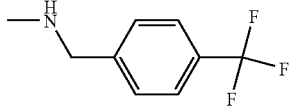 |
| Me | H | 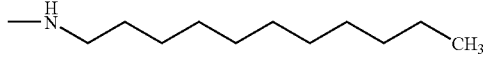 |
| Me | H | 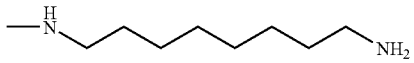 |
| Me | H | 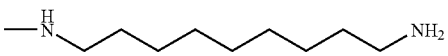 |
| Me | H | 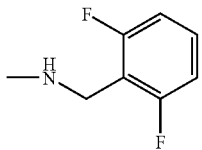 |

TABLE 1-continued
| R₄ | R₅ | R₆ |
|---|---|---|
| Me | H | 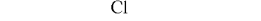 |
| Me | H | 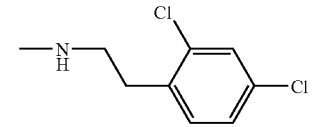 |
| Me | H | 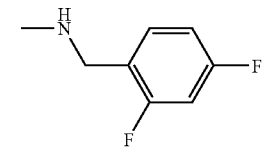 |
| Me | H | 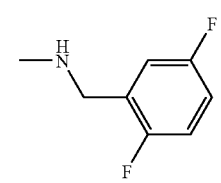 |
| Me | H | 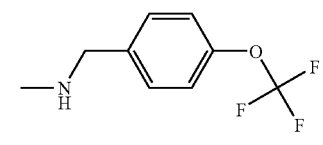 |
| Me | H | 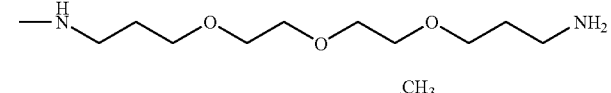 |
| Me | H | 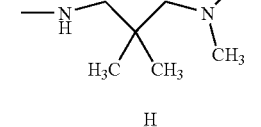 |
| Me | H | 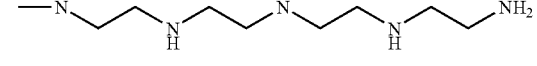 |
| Me | H | 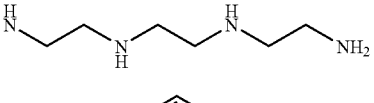 |
| Me | H | 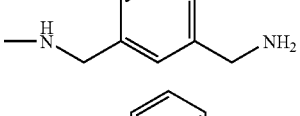 |
| Me | H | 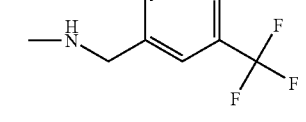 |
| Me | H | 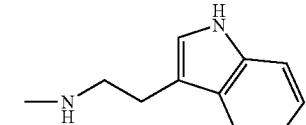 |

TABLE 1-continued
| R4 | R5 | R6 |
|----|----|-----|
| Me | H | 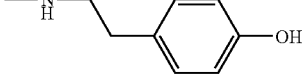 |
| Me | H | 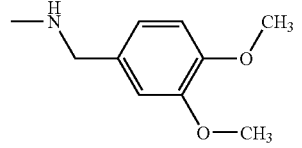 |
| Me | H | 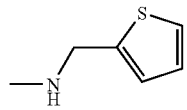 |
| Me | H | 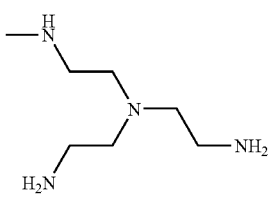 |
| Me | H | 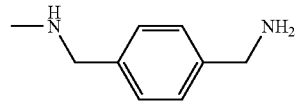 |
| Me | H | 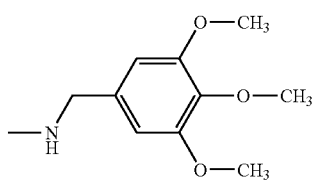 |
| Me | H | 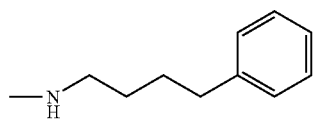 |
| Me | H | 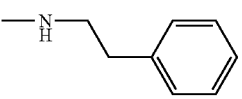 |
| Me | H | 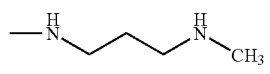 |
| Me | H | 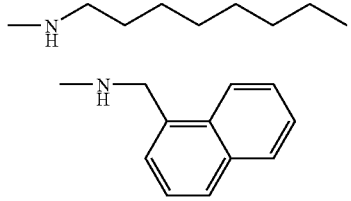 |
| Me | H | 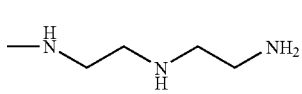 |
| Me | H |  |

TABLE 1-continued
| R₄ | R₅ | R₆ |
|---|---|---|
| Me | H | 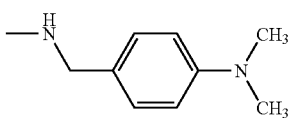 |
| Me | H | 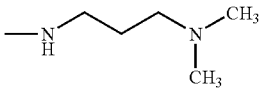 |
| Me | H | 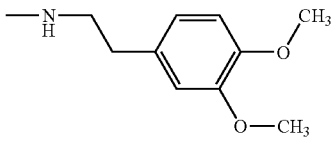 |
| Me | H | 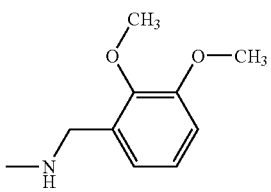 |
| Me | H | 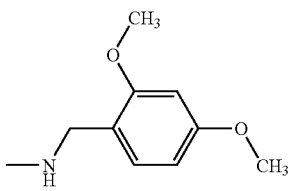 |
| Me | H | 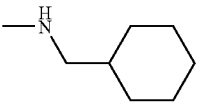 |
| Me | H | 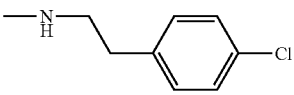 |
| Me | H | 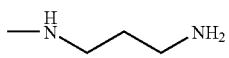 |
| Me | H | 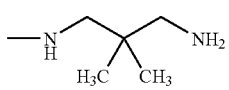 |
| Me | H | 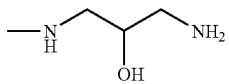 |
| Me | H | 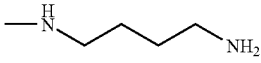 |
| Me | H | 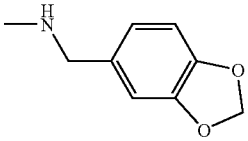 |

TABLE 1-continued
| R4 | R5 | R6 |
|---|---|---|
| Me | H | 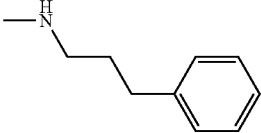 |
| Me | H | 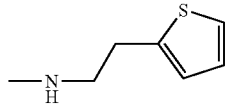 |
| Me | H | 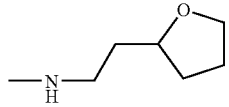 |
| Me | H | 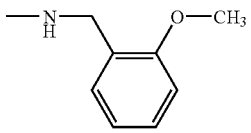 |
| Me | H | 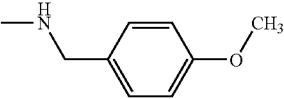 |
| Me | H | 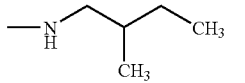 |
| Me | H | 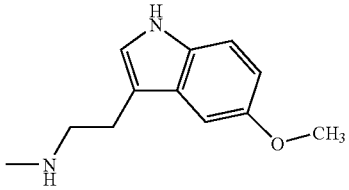 |
| Me | H | 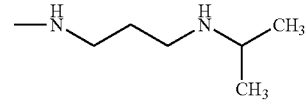 |
| Me | H | 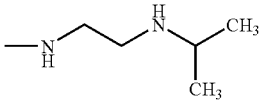 |
| Me | H | 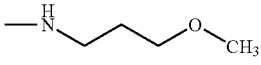 |
| Me | H | 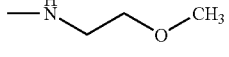 |
| Me | H | 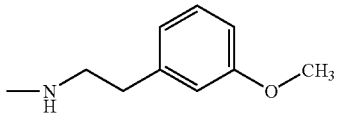 |

TABLE 1-continued
| R₄ | R₅ | R₆ |
|---|---|---|
| Me | H | 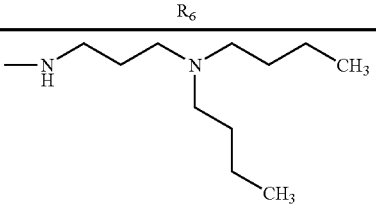 |
| Me | H | 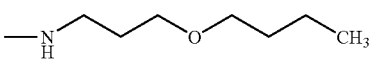 |
| Me | H | 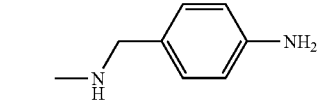 |
| Me | H | 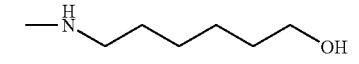 |
| Me | H | 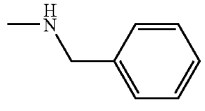 |
| Me | H | 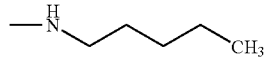 |
| Me | H | 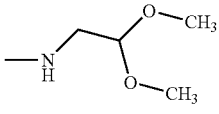 |
| Me | H | 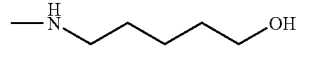 |
| Me | H | 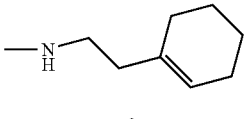 |
| Me | H | 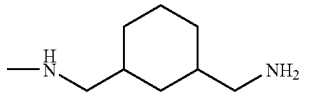 |
| Me | H | 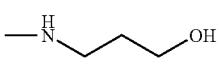 |
| Me | H | 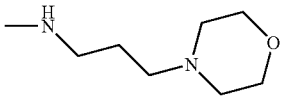 |
| Me | H | 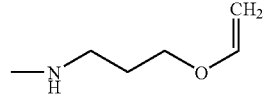 |
| Me | H | 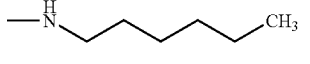 |
| Me | H | 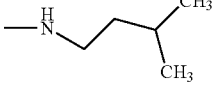 |

TABLE 1-continued
| R4 | R5 | R6 |
|---|---|---|
| Me | H | 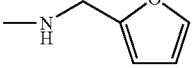 —NH-CH2-(2-furyl) |
| Me | H | 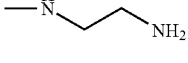 —NH-CH2CH2-NH2 |
| Me | H | 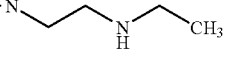 —NH-CH2CH2-NH-CH2CH3 |
| Me | H | 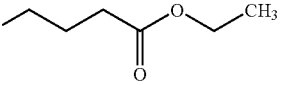 —NH-CH2CH2CH2-C(=O)-O-CH2CH3 |
| Me | H | 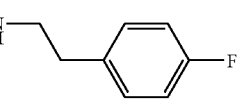 —NH-CH2CH2-(4-fluorophenyl) |
| Me | H | 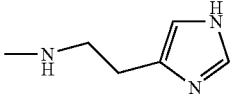 —NH-CH2CH2-(1H-imidazol-4-yl) |
| Me | H | 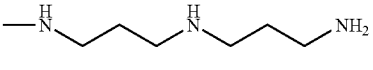 —NH-(CH2)3-NH-(CH2)3-NH2 |
| Me | H | 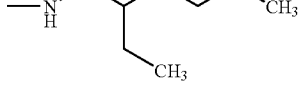 —NH-CH2-CH(CH2CH3)-CH2CH2CH2CH3 |
| Me | H | 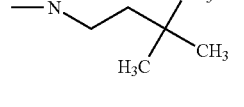 —NH-CH2CH2-C(CH3)3 |
| Me | H | 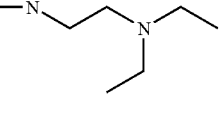 —NH-CH2CH2-N(CH2CH3)2 |
| Me | H | 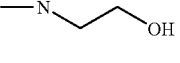 —NH-CH2CH2-OH |
| Me | H | 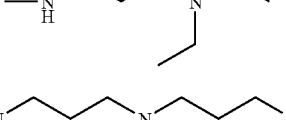 —NH-(CH2)3-N(CH2CH3)2 |
| Me | H | 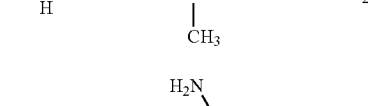 —NH-(CH2)3-N(CH3)-(CH2)3-NH2 |
| Me | H | 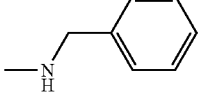 —NH-CH2-(2-aminophenyl) |
| Me | H | 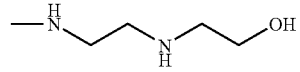 —NH-CH2CH2-NH-CH2CH2-OH |

TABLE 1-continued
| R₄ | R₅ | R₆ |
|---|---|---|
| Me | H | 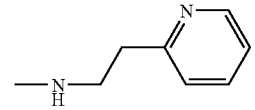 |
| Me | H | 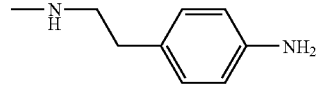 |
| Me | H | 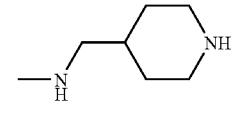 |
| Me | H | 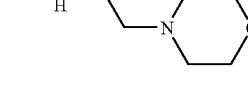 |
| Me | H | 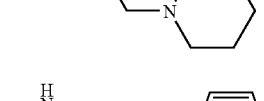 |
| Me | H | 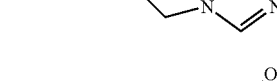 |
| Me | H | 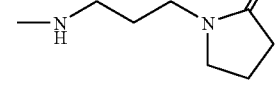 |
| Me | H | 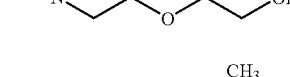 |
| Me | H | 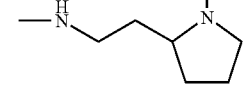 |
| Me | H | 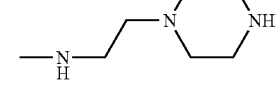 |
| Me | H | 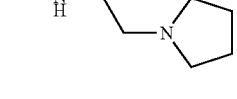 |
| Me | Me | 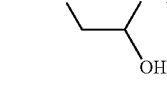 |
| Me | Me | 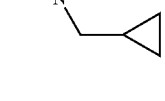 |

TABLE 1-continued

| R$_4$ | R$_5$ | R$_6$ |
|---|---|---|
| Me | Me | —NH—CH$_2$-(pyridin-3-yl) |
| Me | Me | —NH—CH$_2$-(pyridin-2-yl) |
| Me | Me | —NH—CH$_2$—CH(OH)—CH$_3$ (R) |
| Me | Me | —NH—CH$_2$—CH(OH)—CH$_3$ (S) |
| Me | Me | —NH—CH$_2$-(pyrrolidin-2-yl) |
| Me | Me | —NH—(CH$_2$)$_3$-(2-methylpiperidin-1-yl) |
| Me | Me | —NH—CH$_2$CH$_2$—NH-(5-nitropyridin-2-yl) |
| Me | Me | —NH—CH$_2$—CH(OH)—Ph |
| Me | Me | —NH—(CH$_2$)$_4$—OH |
| Me | Me | —NH—CH$_2$-(pyridin-4-yl) |
| Me | Me | —NH—(CH$_2$)$_3$—NH—(CH$_2$)$_3$—NH$_2$ |
| Me | Me | —NH—CH$_2$CH$_2$-(2,5-dimethoxyphenyl) |

TABLE 1-continued

| $R_4$ | $R_5$ | $R_6$ |
|---|---|---|
| Me | Me | —NH—CH2—(3,4-dichlorophenyl) |
| Me | Me | —NH—CH2—(3,4-difluorophenyl) |
| Me | Me | —NH—CH2CH2—N(CH2CH2CH2CH3)2 |
| Me | Me | —NH—CH2—(2-fluorophenyl) |
| Me | Me | —NH—CH2—(4-fluorophenyl) |
| Me | Me | —NH—CH2CH2—N(CH3)2 |
| Me | Me | —NH—CH2CH2—O—CH2CH2—O—CH2CH2—NH2 |
| Me | Me | —NH—CH2—(2-ethoxyphenyl) |
| Me | Me | —NH—CH2CH2CH2—O—CH2CH3 |
| Me | Me | —NH—CH2CH2—(2-fluorophenyl) |
| Me | Me | —NH—CH2CH2—(4-sulfamoylphenyl) |

TABLE 1-continued

| R₄ | R₅ | R₆ |
|---|---|---|
| Me | Me | 5-amino-1,3,3-trimethylcyclohexylmethyl-NH- (3-methylamino group on trimethylcyclohexane with NH₂) |
| Me | Me | 2-amino-3,3,5-trimethylcyclopentylmethyl-NH- |
| Me | Me | -NH-CH₂CH₂CH₂-N(piperazine)N-CH₂CH₂CH₂-NH₂ |
| Me | Me | 3,5-bis(trifluoromethyl)benzyl-NH- |
| Me | Me | 4-bromophenethyl-NH- |
| Me | Me | 4-chlorobenzyl-NH- |
| Me | Me | 4-chlorophenethyl-NH- |
| Me | Me | 2-phenylpropyl-NH- |
| Me | Me | -NH-(CH₂)₆-NH-(CH₂)₆-NH₂ |
| Me | Me | 3-fluoro-5-(trifluoromethyl)benzyl-NH- |

TABLE 1-continued
| R4 | R5 | R6 |
|---|---|---|
| Me | Me | 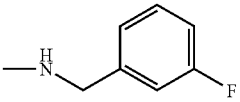 |
| Me | Me | 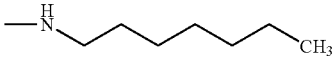 |
| Me | Me | 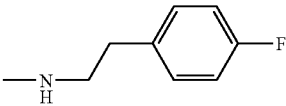 |
| Me | Me | 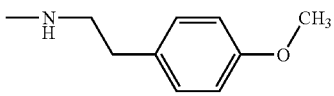 |
| Me | Me | 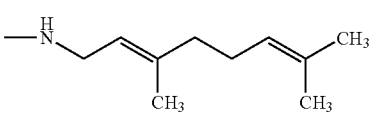 |
| Me | Me | 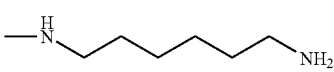 |
| Me | Me | 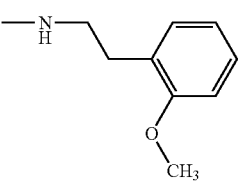 |
| Me | Me | 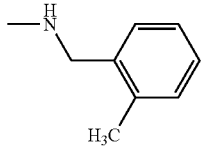 |
| Me | Me | 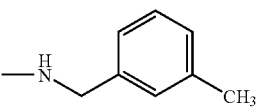 |
| Me | Me | 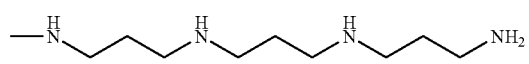 |
| Me | Me | 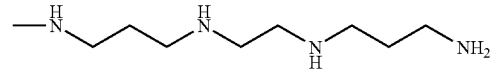 |
| Me | Me | 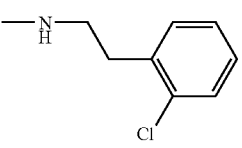 |
| Me | Me | 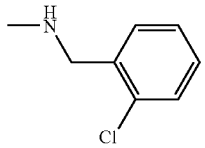 |

TABLE 1-continued

| R₄ | R₅ | R₆ |
|---|---|---|
| Me | Me | 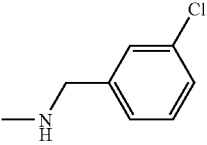 3-chlorobenzyl methylamine |
| Me | Me | 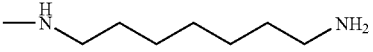 —NH(CH₂)₆NH₂ |
| Me | Me | 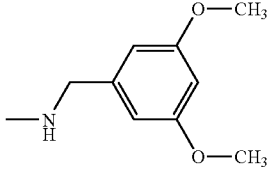 3,5-dimethoxybenzyl methylamine |
| Me | Me | 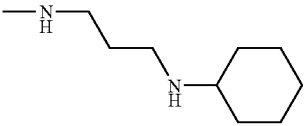 N-cyclohexyl propane-1,3-diamine methyl |
| Me | Me | 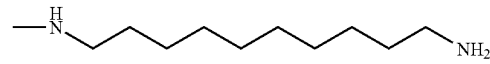 —NH(CH₂)₉NH₂ |
| Me | Me | 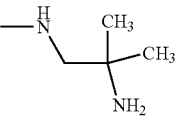 2-methyl-2-amino propyl methylamine |
| Me | Me | 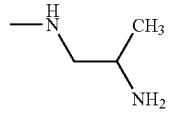 2-amino propyl methylamine |
| Me | Me | 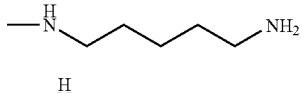 —NH(CH₂)₅NH₂ |
| Me | Me | 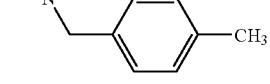 4-methylbenzyl methylamine |
| Me | Me | 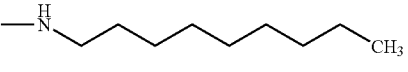 —NH(CH₂)₈CH₃ |
| Me | Me | 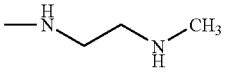 N,N'-dimethyl ethylenediamine |
| Me | Me | 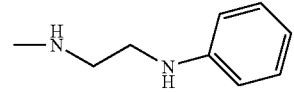 N-phenyl ethylenediamine methyl |
| Me | Me | 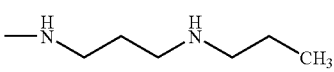 N-propyl propane-1,3-diamine methyl |
| Me | Me | 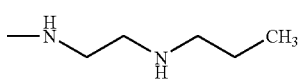 N-propyl ethylenediamine methyl |

TABLE 1-continued
| R4 | R5 | R6 |
|---|---|---|
| Me | Me | 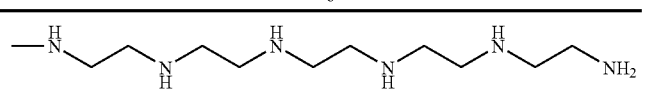 |
| Me | Me | 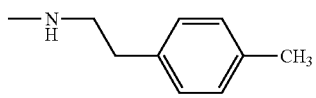 |
| Me | Me | 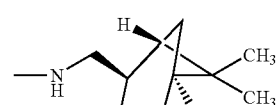 |
| Me | Me | 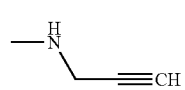 |
| Me | Me | 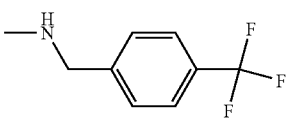 |
| Me | Me | 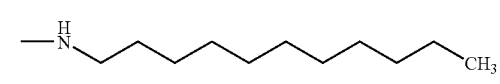 |
| Me | Me | 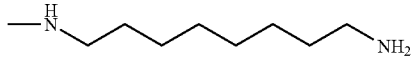 |
| Me | Me | 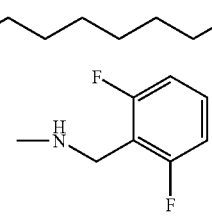 |
| Me | Me | 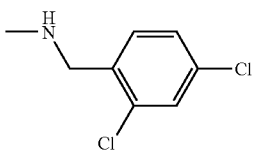 |
| Me | Me | 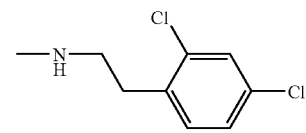 |
| Me | Me | 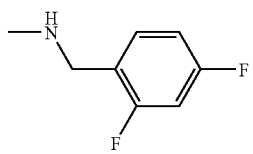 |
| Me | Me | 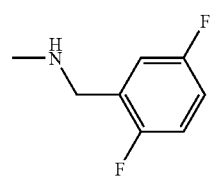 |

TABLE 1-continued

| R₄ | R₅ | R₆ |
|---|---|---|
| Me | Me | —NH—CH₂—C₆H₄—O—CF₃ (4-trifluoromethoxybenzyl) |
| Me | Me | —NH—(CH₂)₃—O—CH₂CH₂—O—CH₂CH₂—O—(CH₂)₃—NH₂ |
| Me | Me | —NH—CH₂—C(CH₃)₂—CH₂—N(CH₃)₂ |
| Me | Me | —NH—CH₂CH₂—NH—CH₂CH₂—NH—CH₂CH₂—NH—CH₂CH₂—NH₂ |
| Me | Me | —NH—CH₂CH₂—NH—CH₂CH₂—NH—CH₂CH₂—NH₂ |
| Me | Me | —NH—CH₂—C₆H₄(m)—CH₂—NH₂ |
| Me | Me | —NH—CH₂—C₆H₄(m)—CF₃ |
| Me | Me | —NH—CH₂CH₂—(1H-indol-3-yl) |
| Me | Me | —NH—CH₂CH₂—C₆H₄(p)—OH |
| Me | Me | —NH—CH₂—C₆H₃(3,4-di-OMe) |
| Me | Me | —NH—CH₂—(thiophen-2-yl) |
| Me | Me | —NH—CH₂CH₂—N(CH₂CH₂NH₂)(CH₂CH₂NH₂) |

TABLE 1-continued

| R₄ | R₅ | R₆ |
|---|---|---|
| Me | Me | —NH—CH₂—C₆H₄—CH₂NH₂ (para) |
| Me | Me | —NH—CH₂—(3,4,5-trimethoxyphenyl) |
| Me | Me | —NH—(CH₂)₃—C₆H₅ |
| Me | Me | —NH—CH₂CH₂—C₆H₅ |
| Me | Me | —NH—(CH₂)₃—NH—CH₃ |
| Me | Me | —NH—(CH₂)₇—CH₃ |
| Me | Me | —NH—CH₂—(1-naphthyl) |
| Me | Me | —NH—CH₂CH₂—NH—CH₂CH₂—NH₂ |
| Me | Me | —NH—CH₂—C₆H₄—N(CH₃)₂ (para) |
| Me | Me | —NH—(CH₂)₃—N(CH₃)₂ |
| Me | Me | —NH—CH₂CH₂—(3,4-dimethoxyphenyl) |
| Me | Me | —NH—CH₂—(2,3-dimethoxyphenyl) |

TABLE 1-continued

| $R_4$ | $R_5$ | $R_6$ |
|---|---|---|
| Me | Me | —NH—CH₂-(2,4-dimethoxyphenyl) |
| Me | Me | —NH—CH₂-cyclohexyl |
| Me | Me | —NH—CH₂CH₂-(4-chlorophenyl) |
| Me | Me | —NH—CH₂CH₂CH₂—NH₂ |
| Me | Me | —NH—CH₂—C(CH₃)₂—CH₂—NH₂ |
| Me | Me | —NH—CH₂—CH(OH)—CH₂—NH₂ |
| Me | Me | —NH—CH₂CH₂CH₂CH₂—NH₂ |
| Me | Me | —NH—CH₂-(3,4-methylenedioxyphenyl) |
| Me | Me | —NH—CH₂CH₂CH₂-phenyl |
| Me | Me | —NH—CH₂CH₂-(2-thienyl) |
| Me | Me | —NH—CH₂CH₂-(tetrahydrofuran-2-yl) |
| Me | Me | —NH—CH₂-(2-methoxyphenyl) |

TABLE 1-continued

| R₄ | R₅ | R₆ |
|---|---|---|
| Me | Me | —NH—CH₂—C₆H₄—OCH₃ (4-methoxybenzyl) |
| Me | Me | —NH—CH₂—CH(CH₃)—CH₂—CH₃ (2-methylbutyl) |
| Me | Me | —NH—CH₂CH₂—(5-methoxy-1H-indol-3-yl) |
| Me | Me | —NH—(CH₂)₃—NH—CH(CH₃)₂ |
| Me | Me | —NH—(CH₂)₂—NH—CH(CH₃)₂ |
| Me | Me | —NH—(CH₂)₃—O—CH₃ |
| Me | Me | —NH—(CH₂)₂—O—CH₃ |
| Me | Me | —NH—CH₂CH₂—C₆H₄—OCH₃ (3-methoxyphenethyl) |
| Me | Me | —NH—(CH₂)₃—N(C₄H₉)(C₅H₁₁) |
| Me | Me | —NH—(CH₂)₃—O—C₄H₉ |
| Me | Me | —NH—CH₂—C₆H₄—NH₂ (4-aminobenzyl) |
| Me | Me | —NH—(CH₂)₅—OH |
| Me | Me | —NH—CH₂—C₆H₅ (benzyl) |

TABLE 1-continued
| R4 | R5 | R6 |
|---|---|---|
| Me | Me | 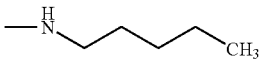 |
| Me | Me | 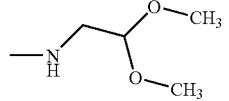 |
| Me | Me | 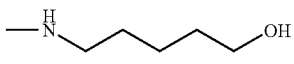 |
| Me | Me | 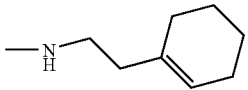 |
| Me | Me | 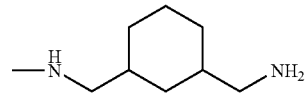 |
| Me | Me | 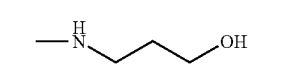 |
| Me | Me |  |
| Me | Me | 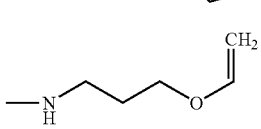 |
| Me | Me | 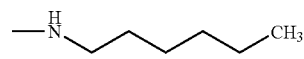 |
| Me | Me | 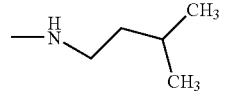 |
| Me | Me | 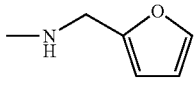 |
| Me | Me | 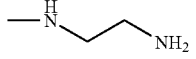 |
| Me | Me | 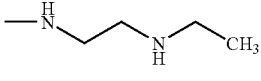 |
| Me | Me | 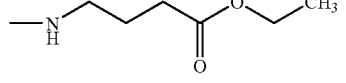 |
| Me | Me | 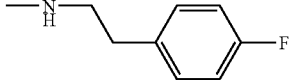 |
| Me | Me | 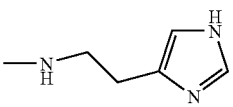 |

TABLE 1-continued

| R₄ | R₅ | R₆ |
|----|----|----|
| Me | Me | —NH-CH₂CH₂CH₂-NH-CH₂CH₂CH₂-NH₂ |
| Me | Me | —NH-CH₂-CH(CH₂CH₃)-CH₂CH₂CH₂-CH₃ |
| Me | Me | —NH-CH₂CH₂-C(CH₃)₃ |
| Me | Me | —NH-CH₂CH₂-N(CH₂CH₃)₂ |
| Me | Me | —NH-CH₂CH₂-OH |
| Me | Me | —NH-CH₂CH₂CH₂-N(CH₂CH₃)₂ |
| Me | Me | —NH-CH₂CH₂CH₂-N(CH₃)-CH₂CH₂CH₂-NH₂ |
| Me | Me | —NH-CH₂-(2-aminophenyl) |
| Me | Me | —NH-CH₂CH₂-NH-CH₂CH₂-OH |
| Me | Me | —NH-CH₂CH₂-(pyridin-2-yl) |
| Me | Me | —NH-CH₂CH₂-(4-aminophenyl) |
| Me | Me | —NH-CH₂-(piperidin-4-yl) |
| Me | Me | —NH-CH₂CH₂-(morpholin-4-yl) |
| Me | Me | —NH-CH₂CH₂-(piperidin-1-yl) |

TABLE 1-continued
| R4 | R5 | R6 |
|---|---|---|
| Me | Me | 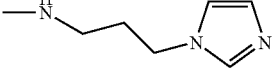 |
| Me | Me | 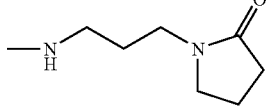 |
| Me | Me | 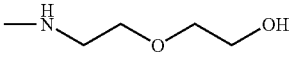 |
| Me | Me | 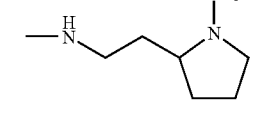 |
| Me | Me | 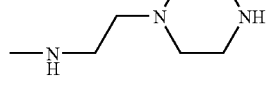 |
| Me | Me | 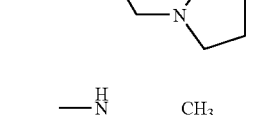 |
| Me | Me | 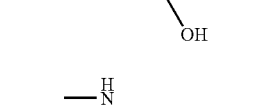 |
| Me | Me | 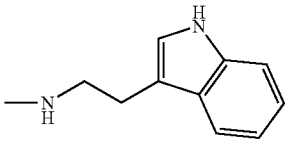 |
| Me | CH$_2$OEt | 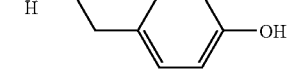 |
| Me | CH$_2$OEt | 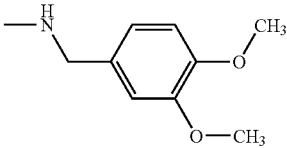 |
| Me | CH$_2$OEt | 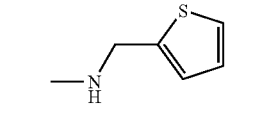 |
| Me | CH$_2$OEt | |

TABLE 1-continued
| R$_4$ | R$_5$ | R$_6$ |
|---|---|---|
| Me | CH$_2$OEt | 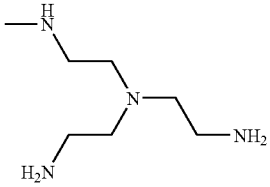 |
| Me | CH$_2$OEt | 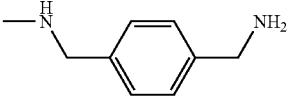 |
| Me | CH$_2$OEt | 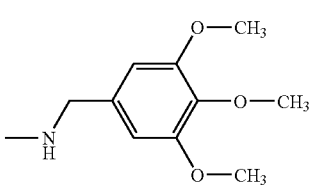 |
| Me | CH$_2$OEt | 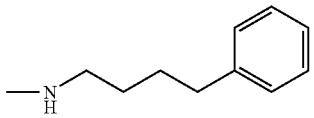 |
| Me | CH$_2$OEt | 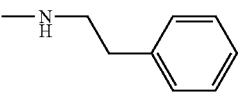 |
| Me | CH$_2$OEt | 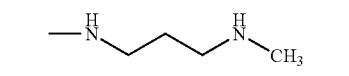 |
| Me | CH$_2$OEt | 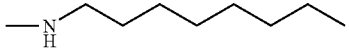 |
| Me | CH$_2$OEt | 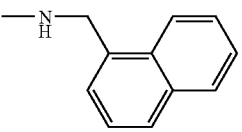 |
| Me | CH$_2$OEt | 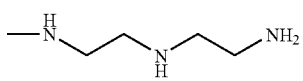 |
| Me | CH$_2$OEt | 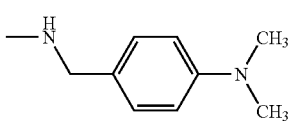 |
| Me | CH$_2$OEt | 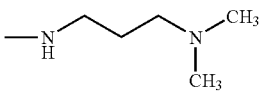 |
| Me | CH$_2$OEt | 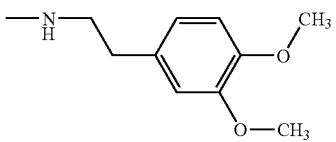 |

TABLE 1-continued

| R$_4$ | R$_5$ | R$_6$ |
|---|---|---|
| Me | CH$_2$OEt | -NH-CH$_2$-(2,3-dimethoxyphenyl) |
| Me | CH$_2$OEt | -NH-CH$_2$-(2,4-dimethoxyphenyl) |
| Me | CH$_2$OEt | -NH-CH$_2$-cyclohexyl |
| Me | CH$_2$OEt | -NH-CH$_2$CH$_2$-(4-chlorophenyl) |
| Me | CH$_2$OEt | -NH-CH$_2$CH$_2$CH$_2$-NH$_2$ |
| Me | CH$_2$OEt | -NH-CH$_2$-C(CH$_3$)$_2$-CH$_2$-NH$_2$ |
| Me | CH$_2$OEt | -NH-CH$_2$-CH(OH)-CH$_2$-NH$_2$ |
| Me | CH$_2$OEt | -NH-CH$_2$CH$_2$CH$_2$CH$_2$-NH$_2$ |
| Me | CH$_2$OEt | -NH-CH$_2$-(benzo[1,3]dioxol-5-yl) |
| Me | CH$_2$OEt | -NH-CH$_2$CH$_2$CH$_2$-phenyl |
| Me | CH$_2$OEt | -NH-CH$_2$CH$_2$-(thiophen-2-yl) |
| Me | CH$_2$OEt | -NH-CH$_2$CH$_2$-(tetrahydrofuran-2-yl) |

TABLE 1-continued

| $R_4$ | $R_5$ | $R_6$ |
|---|---|---|
| Me | CH$_2$OEt | —NH—CH$_2$—(2-methoxyphenyl) |
| Me | CH$_2$OEt | —NH—CH$_2$—(4-methoxyphenyl) |
| Me | CH$_2$OEt | —NH—CH$_2$—CH(CH$_3$)—CH$_2$CH$_3$ |
| Me | CH$_2$OEt | —NH—CH$_2$CH$_2$—(5-methoxy-1H-indol-3-yl) |
| Me | CH$_2$OEt | —NH—CH$_2$CH$_2$CH$_2$—NH—CH(CH$_3$)$_2$ |
| Me | CH$_2$OEt | —NH—CH$_2$CH$_2$—NH—CH(CH$_3$)$_2$ |
| Me | CH$_2$OEt | —NH—CH$_2$CH$_2$CH$_2$—O—CH$_3$ |
| Me | CH$_2$OEt | —NH—CH$_2$CH$_2$—O—CH$_3$ |
| Me | CH$_2$OEt | —NH—CH$_2$CH$_2$—(3-methoxyphenyl) |
| Me | CH$_2$OEt | —NH—CH$_2$CH$_2$CH$_2$—N(C$_4$H$_9$)$_2$ |
| Me | CH$_2$OEt | —NH—CH$_2$CH$_2$CH$_2$—O—C$_4$H$_9$ |
| Me | CH$_2$OEt | —NH—CH$_2$—(4-aminophenyl) |
| Me | CH$_2$OEt | —NH—(CH$_2$)$_6$—OH |

TABLE 1-continued

| R$_4$ | R$_5$ | R$_6$ |
|---|---|---|
| Me | CH$_2$OEt | 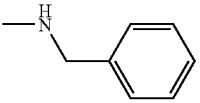 —NH—CH$_2$—C$_6$H$_5$ |
| Me | CH$_2$OEt | 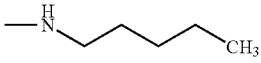 —NH—(CH$_2$)$_3$—CH$_3$ |
| Me | CH$_2$OEt | 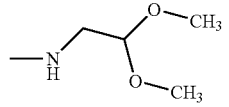 —NH—CH$_2$—CH(OCH$_3$)$_2$ |
| Me | CH$_2$OEt | 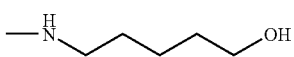 —NH—(CH$_2$)$_4$—OH |
| Me | CH$_2$OEt | 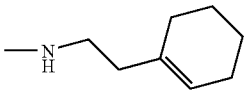 —NH—CH$_2$CH$_2$-cyclohexenyl |
| Me | CH$_2$OEt | 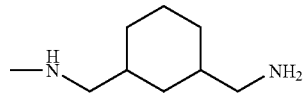 —NH—CH$_2$-cyclohexyl-CH$_2$NH$_2$ |
| Me | CH$_2$OEt | 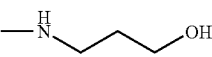 —NH—(CH$_2$)$_3$—OH |
| Me | CH$_2$OEt | 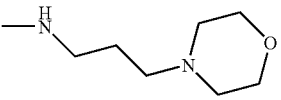 —NH—(CH$_2$)$_3$-morpholinyl |
| Me | CH$_2$OEt | 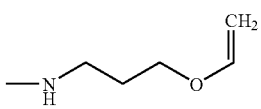 —NH—(CH$_2$)$_3$—O—CH=CH$_2$ |
| Me | CH$_2$OEt | 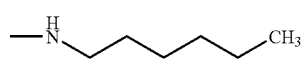 —NH—(CH$_2$)$_5$—CH$_3$ |
| Me | CH$_2$OEt | 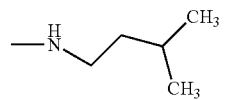 —NH—CH$_2$CH$_2$—CH(CH$_3$)$_2$ |
| Me | CH$_2$OEt | 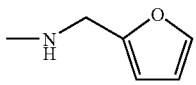 —NH—CH$_2$-furyl |
| Me | CH$_2$OEt | 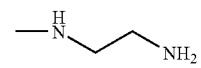 —NH—CH$_2$CH$_2$—NH$_2$ |
| Me | CH$_2$OEt | 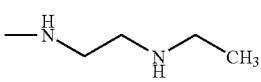 —NH—CH$_2$CH$_2$—NH—CH$_2$CH$_3$ |
| Me | CH$_2$OEt | 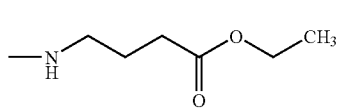 —NH—(CH$_2$)$_3$—C(O)—O—CH$_2$CH$_3$ |
| Me | CH$_2$OEt | 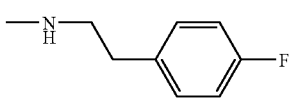 —NH—CH$_2$CH$_2$—(4-F-C$_6$H$_4$) |

TABLE 1-continued

| R₄ | R₅ | R₆ |
|---|---|---|
| Me | CH₂OEt | —NH-CH₂CH₂-(1H-imidazol-4-yl) |
| Me | CH₂OEt | —NH-(CH₂)₃-NH-(CH₂)₃-NH₂ |
| Me | CH₂OEt | —NH-CH₂-CH(CH₂CH₃)-(CH₂)₃-CH₃ |
| Me | CH₂OEt | —NH-CH₂CH₂-C(CH₃)₃ |
| Me | CH₂OEt | —NH-CH₂CH₂-N(CH₂CH₃)₂ |
| Me | CH₂OEt | —NH-CH₂CH₂-OH |
| Me | CH₂OEt | —NH-(CH₂)₃-N(CH₂CH₃)₂ |
| Me | CH₂OEt | —NH-(CH₂)₃-N(CH₃)-(CH₂)₃-NH₂ |
| Me | CH₂OEt | —NH-CH₂-(2-aminophenyl) |
| Me | CH₂OEt | —NH-CH₂CH₂-NH-CH₂CH₂-OH |
| Me | CH₂OEt | —NH-CH₂CH₂-(pyrimidin-2-yl) |
| Me | CH₂OEt | —NH-CH₂CH₂-(4-aminophenyl) |
| Me | CH₂OEt | —NH-CH₂-(piperidin-4-yl) |
| Me | CH₂OEt | —NH-CH₂CH₂-(morpholin-4-yl) |

TABLE 1-continued
| R4 | R5 | R6 |
|---|---|---|
| Me | CH2OEt | 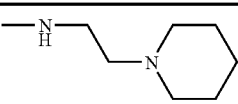 |
| Me | CH2OEt | 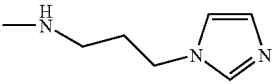 |
| Me | CH2OEt | 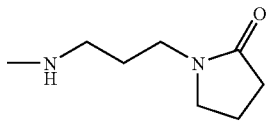 |
| Me | CH2OEt | 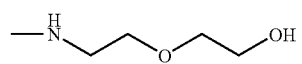 |
| Me | CH2OEt | 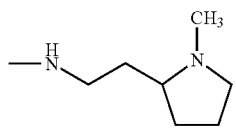 |
| Me | CH2OEt | 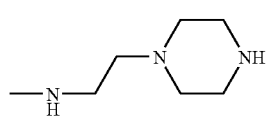 |
| Me | CH2OEt | 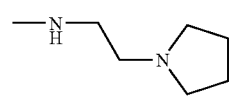 |
| Me | CH2OEt | 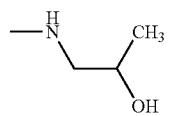 |
| Me | CH2OEt | 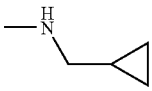 |
| Me | CH2OEt | 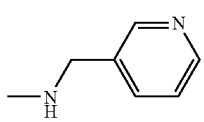 |
| Me | CH2OEt | 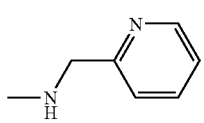 |
| Me | CH2OEt | 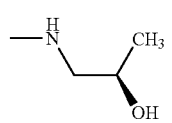 |
| Me | CH2OEt | 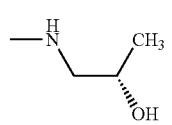 |

TABLE 1-continued
| R4 | R5 | R6 |
|---|---|---|
| Me | CH2OEt | 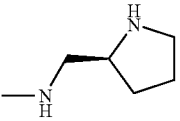 |
| Me | CH2OEt | 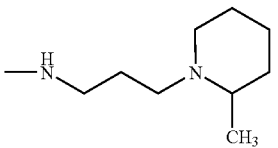 |
| Me | CH2OEt | 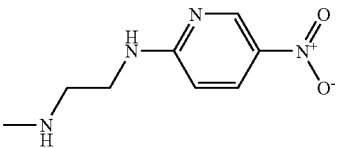 |
| Me | CH2OEt | 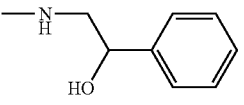 |
| Me | CH2OEt | 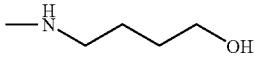 |
| Me | CH2OEt | 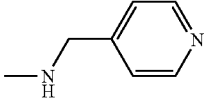 |
| Me | CH2OEt | 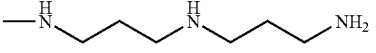 |
| Me | CH2OEt | 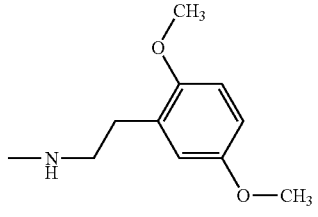 |
| Me | CH2OEt | 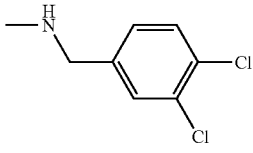 |
| Me | CH2OEt | 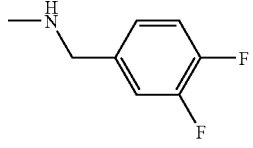 |
| Me | CH2OEt | 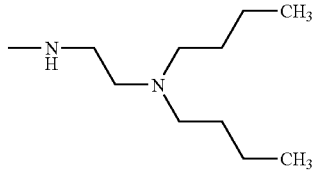 |

TABLE 1-continued
| R4 | R5 | R6 |
|---|---|---|
| Me | CH2OEt | 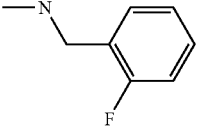 |
| Me | CH2OEt | 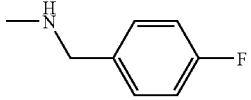 |
| Me | CH2OEt | 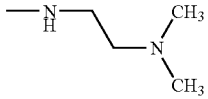 |
| Me | CH2OEt | 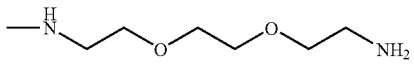 |
| Me | CH2OEt | 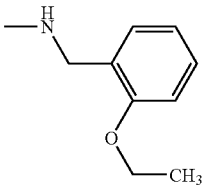 |
| Me | CH2OEt | 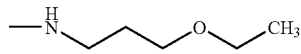 |
| Me | CH2OEt | 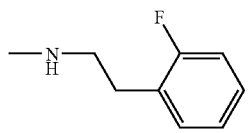 |
| Me | CH2OEt | 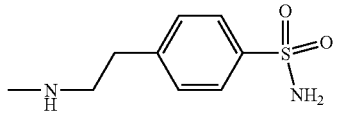 |
| Me | CH2OEt | 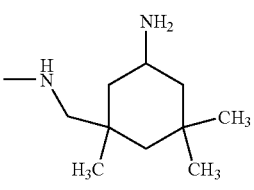 |
| Me | CH2OEt | 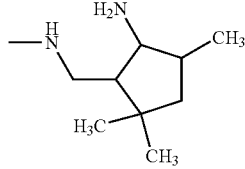 |
| Me | CH2OEt | 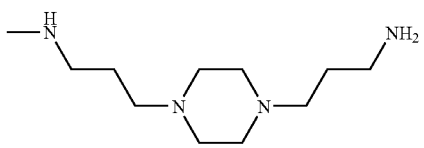 |

TABLE 1-continued
| R$_4$ | R$_5$ | R$_6$ |
|---|---|---|
| Me | CH$_2$OEt | 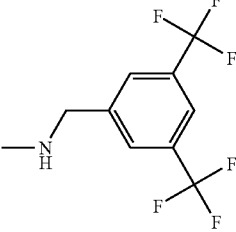 |
| Me | CH$_2$OEt | 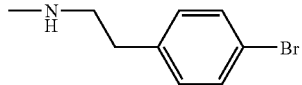 |
| Me | CH$_2$OEt | 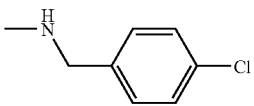 |
| Me | CH$_2$OEt | 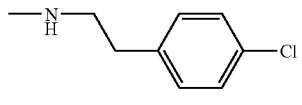 |
| Me | CH$_2$OEt | 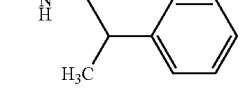 |
| Me | CH$_2$OEt | 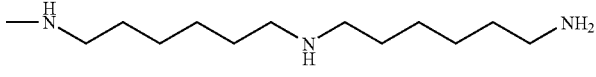 |
| Me | CH$_2$OEt | 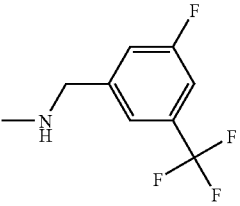 |
| Me | CH$_2$OEt | 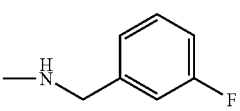 |
| Me | CH$_2$OEt | 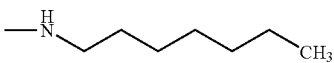 |
| Me | CH$_2$OEt | 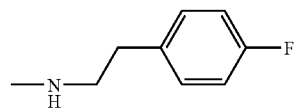 |
| Me | CH$_2$OEt | 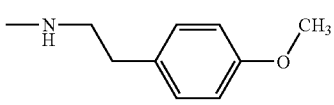 |
| Me | CH$_2$OEt | 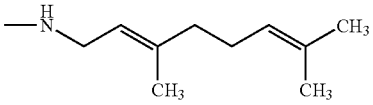 |

TABLE 1-continued

| R₄ | R₅ | R₆ |
|---|---|---|
| Me | CH₂OEt | —NH—(CH₂)₆—NH₂ |
| Me | CH₂OEt | —NH—CH₂CH₂—(2-methoxyphenyl) |
| Me | CH₂OEt | —NH—CH₂—(2-methylphenyl) |
| Me | CH₂OEt | —NH—CH₂—(3-methylphenyl) |
| Me | CH₂OEt | —NH—(CH₂)₃—NH—(CH₂)₃—NH—(CH₂)₃—NH₂ |
| Me | CH₂OEt | —NH—(CH₂)₃—NH—(CH₂)₂—NH—(CH₂)₃—NH₂ |
| Me | CH₂OEt | —NH—CH₂CH₂—(2-chlorophenyl) |
| Me | CH₂OEt | —NH—CH₂—(2-chlorophenyl) |
| Me | CH₂OEt | —NH—CH₂—(3-chlorophenyl) |
| Me | CH₂OEt | —NH—(CH₂)₇—NH₂ |
| Me | CH₂OEt | —NH—CH₂—(3,5-dimethoxyphenyl) |
| Me | CH₂OEt | —NH—(CH₂)₃—NH—cyclohexyl |

TABLE 1-continued
| R4 | R5 | R6 |
|---|---|---|
| Me | CH2OEt | 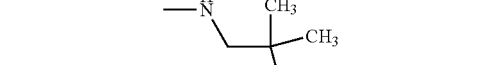 —NH—(CH2)9—NH2 |
| Me | CH2OEt | 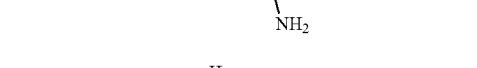 —NH—CH2—C(CH3)2—NH2 |
| Me | CH2OEt | 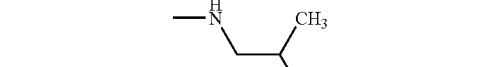 —NH—CH2—CH(CH3)—NH2 |
| Me | CH2OEt |  —NH—(CH2)5—NH2 |
| Me | CH2OEt | 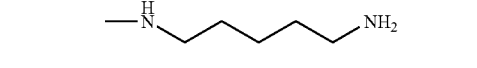 —NH—CH2—C6H4—CH3 |
| Me | CH2OEt | 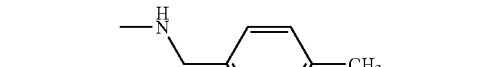 —NH—(CH2)8—CH3 |
| Me | CH2OEt | 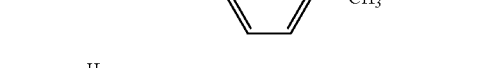 —NH—CH2CH2—NH—CH3 |
| Me | CH2OEt | 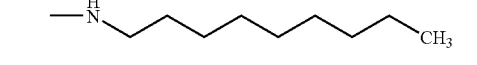 —NH—CH2CH2—NH—C6H5 |
| Me | CH2OEt | 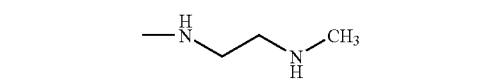 —NH—(CH2)3—NH—(CH2)2CH3 |
| Me | CH2OEt |  —NH—CH2CH2—NH—(CH2)2CH3 |
| Me | CH2OEt | 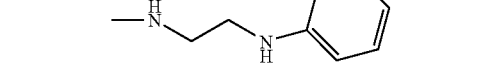 —NH—(CH2CH2NH)5—H with terminal NH2 |
| Me | CH2OEt | 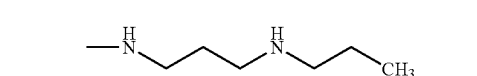 —NH—CH2CH2—C6H4—CH3 |
| Me | CH2OEt |  norbornyl methylamine derivative |
| Me | CH2OEt | 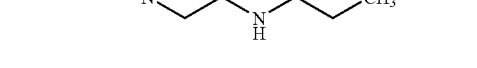 —NH—CH2—C≡CH |
| Me | CH2OEt | 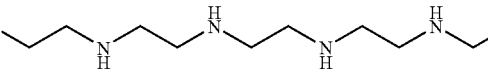 —NH—CH2—C6H4—CF3 |

TABLE 1-continued
| R4 | R5 | R6 |
|---|---|---|
| Me | CH2OEt | 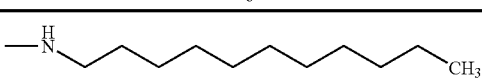 |
| Me | CH2OEt | 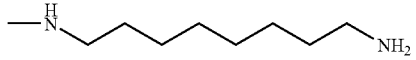 |
| Me | CH2OEt | 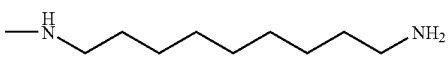 |
| Me | CH2OEt | 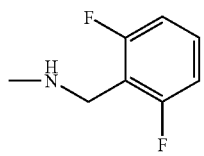 |
| Me | CH2OEt | 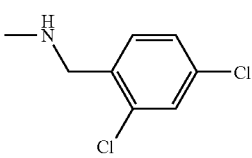 |
| Me | CH2OEt | 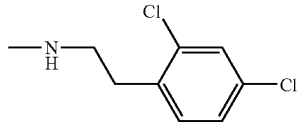 |
| Me | CH2OEt | 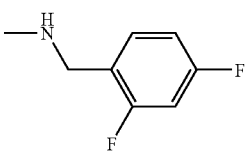 |
| Me | CH2OEt | 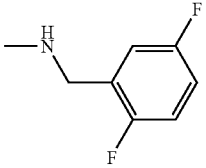 |
| Me | CH2OEt | 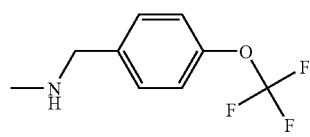 |
| Me | CH2OEt | 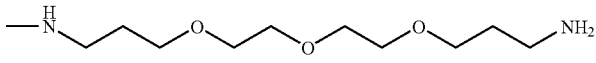 |
| Me | CH2OEt | 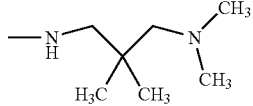 |
| Me | CH2OEt | 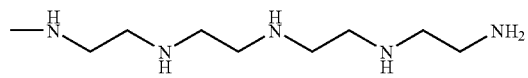 |
| Me | CH2OEt | 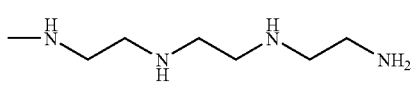 |

TABLE 1-continued

| R₄ | R₅ | R₆ |
|---|---|---|
| Me | CH₂OEt | 3-(aminomethyl)-N-methylbenzylamine |
| Me | CH₂OEt | N-methyl-[3-(trifluoromethyl)benzyl]amine |

| R₄ | R₅ | R₆ |
|---|---|---|
| (S)-1-bromo-2-methylbutane | Me | H |
| 1-propylaziridine | Me | H |
| tridecane | Me | H |
| 1-bromotetradecane | Me | H |
| (pentafluorophenyl)ethyl | Me | H |
| 2-propylthiophene | Me | H |
| 3-propylthiophene | Me | H |
| 1-fluoro-2-propylbenzene | Me | H |
| 2-butylpyridine | Me | H |
| 2-ethylthiophene | Me | H |
| 4-propyl-1,2-dimethoxybenzene | Me | H |

-continued

| R₄ | R₅ | R₆ |
|---|---|---|
| 3-(trifluoromethyl)phenylpropyl | Me | H |
| 4-bromobutyl | Me | H |
| 3-furylethyl | Me | H |
| 4-(trimethylsilyl)butyl | Me | H |
| pent-4-enyl | Me | H |
| 3-chloro-2,2-dimethylbutyl | Me | H |
| 3-(3-chlorophenyl)propyl | Me | H |
| 4-(diethylamino)butyl | Me | H |
| 4-(dimethylamino)butyl | Me | H |
| 3-(3-fluorophenyl)propyl | Me | H |
| hept-3-yn-1-yl | Me | H |
| 3-cyanopropyl | Me | H |
| 3-(3-methoxyphenyl)propyl | Me | H |
| 3-methylhexan-3-yl substituent | Me | H |
| 4-(trimethylsilyl)but-3-yn-1-yl | Me | H |

-continued
| R₄ | R₅ | R₆ |
|---|---|---|
| 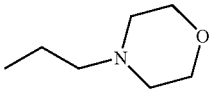 | Me | H |
| 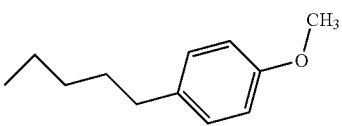 | Me | H |
| 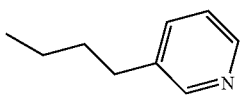 | Me | H |
| 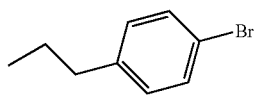 | Me | H |
| 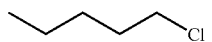 | Me | H |
| 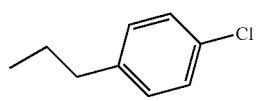 | Me | H |
| 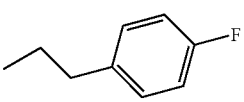 | Me | H |
| 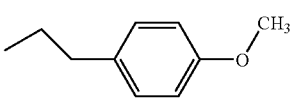 | Me | H |
| 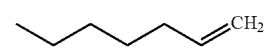 | Me | H |
| 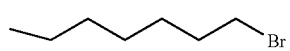 | Me | H |
| 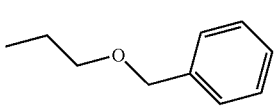 | Me | H |
| 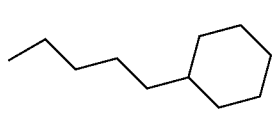 | Me | H |
| 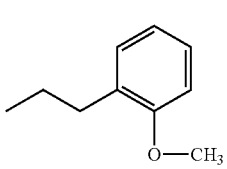 | Me | H |
| 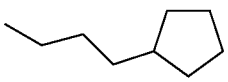 | Me | H |
| 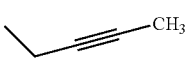 | Me | H |

-continued

| R₄ | R₅ | R₆ |
|---|---|---|
| 2-propylnaphthalene | Me | H |
| dec-5-yne | Me | H |
| 1-pentyl-4-nitrobenzene | Me | H |
| 5-propyl-4-methylthiazole | Me | H |
| 1-propyl-4-methylbenzene | Me | H |
| 1-propyl-4-nitrobenzene | Me | H |
| hept-1-ene | Me | H |
| pentylbenzene | Me | H |
| 4-butylpyridine | Me | H |
| hexylbenzene | Me | H |
| 2-butyl-6-methylpyridine | Me | H |
| butan-2-one | Me | H |
| (E)-but-1-enylbenzene | Me | H |
| (Z)-hept-3-ene | Me | H |

-continued

| R₄ | R₅ | R₆ |
|---|---|---|
| ethyl heptanoate structure | Me | H |
| diene with methyl groups structure | Me | H |
| 1-propyl-2-methyl-5-nitroimidazole structure | Me | H |
| propyl (3-nitrophenyl) sulfone structure | Me | H |
| bromoalkyl chain structure | Me | H |
| 1-bromo-2,2-dimethylbutyl structure | Me | H |
| sec-butyl methylcyclohexene structure | Me | H |
| 1-propyl-2-pyrrolidinone structure | Me | H |
| 1-propylpyrrolidine structure | Me | H |
| propyl adamantane structure | Me | H |
| long alkyl chain (CH₃) | Me | H |
| 1-propylnaphthalene structure | Me | H |

| R₄ | R₅ | R₆ |
|---|---|---|
| propyl-piperidine | Me | H |
| butyl (CH₃) | Me | H |
| pentyl-pyrene | Me | H |
| propyl-O-ethyl-O-ethyl-Cl | Me | H |
| butyl-phthalimide | Me | H |
| propyl-N(CH₂CH₃)₂ | Me | H |
| propyl-N(CH₃)(CH₂Ph) | Me | H |
| CH₃-CH=CH-CH=CH-propyl | Me | H |
| PhCH=C(CH₃)CH₂CH₃ | Me | H |
| CH₃CH₂-CH=CH-propyl | Me | H |
| oleyl chain | Me | H |
| CH₃CH₂-C(F₂)-CF₃ | Me | H |
| geranyl-type chain | Me | H |

-continued

| R₄ | R₅ | R₆ |
|---|---|---|
| 2,2-dimethylbutanal group | Me | H |
| pentyl acrylate group | Me | H |
| 3-ethylhexyl (2-ethylhexyl) group | Me | H |
| 2-methylpentyl group | Me | H |
| propoxy-2,3,6-trifluorophenyl group | Me | H |
| 2-(2-chloroethoxy)propyl group | Me | H |
| 2-propylpyridine group | Me | H |
| 3-propoxypropyl-6-methylpyridin-2-yl group | Me | H |
| 4-bromophenoxypropyl group | Me | H |
| N-butyl-N-propylpentylamine group | Me | H |
| propylsulfonylmethane group | Me | H |
| propyl methyl sulfide group | Me | H |
| N-ethyl-N-propyl-3-methylaniline group | Me | H |

-continued

| R₄ | R₅ | R₆ |
|---|---|---|
| propylsulfonyl-phenyl | Me | H |
| propylthio-phenyl | Me | H |
| propyl-trimethylsilyl | Me | H |
| 1,1,1-trifluoropropyl (CF₃CH₂CH₂-) | Me | H |
| 3-methyl-2-pentanone group | Me | H |
| 3-nitrophenyl-propyl | Me | H |
| butoxy-propoxy-methyl ether chain | Me | H |
| cis-decenyl | Me | H |
| 3,5,5-trimethyl-octyl branched | Me | H |
| butyl-phenyl | Me | H |
| phytyl-like polyisoprenoid chain | Me | H |
| 3,7-dimethyl-oct-6-enyl | Me | H |
| methyl 2,2-dimethylbutanoate | Me | H |

-continued

| R₄ | R₅ | R₆ |
|---|---|---|
| CH₃CH=C(CH₃)CH₂CH₂– (2-methyl-2-pentenyl) | Me | H |
| CH₂=C(CH₃)CH₂CH₂CH₂– | Me | H |
| 3-methylphenylpropyl | Me | H |
| CH₃C≡C-CH₂CH₂CH₂– | Me | H |
| CH₃CH₂-CF₂-CF₂-CF₃ (perfluoro chain with ethyl) | Me | H |
| CH₃CH₂-CF₂-CF₂-CHF₂ | Me | H |
| CH₃CH₂-CF₂-CHF₂ | Me | H |
| 1,1-diphenylpropyl (Ph₂CH-CH₂CH₃) | Me | H |
| CH₃CH₂CH(CH₃)CH₂C(CH₃)₂CH₃ (branched alkyl) | Me | H |
| CH₂=CH-CH₂-CH(CH₃)-CH=C(CH₃)-CH₂CH₃ | Me | H |
| Cl-CH₂CH₂CH₂– | Me | H |
| 2-chlorophenylpropyl | Me | H |

-continued
| R$_4$ | R$_5$ | R$_6$ |
|---|---|---|
| 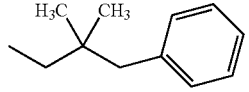 | Me | H |
|  | Me | H |
| 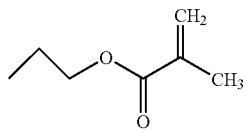 | Me | H |
| 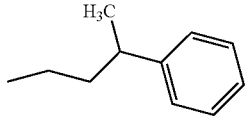 | Me | H |
| 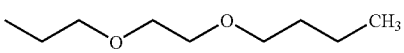 | Me | H |
| 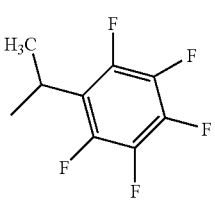 | Me | H |
| 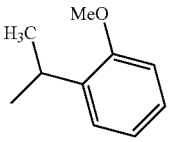 | Me | H |
| 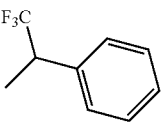 | Me | H |
| 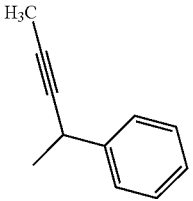 | Me | H |
| 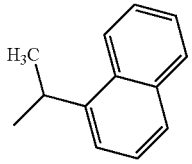 | Me | H |
| 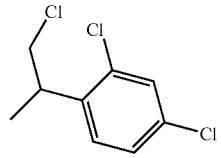 | Me | H |

-continued
| R₄ | R₅ | R₆ |
|---|---|---|
| 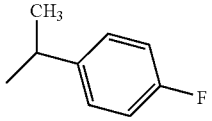 | Me | H |
| 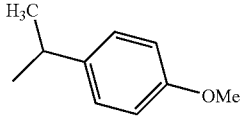 | Me | H |
| 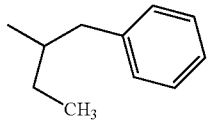 | Me | H |
| 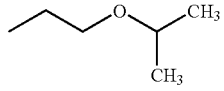 | Me | H |
| 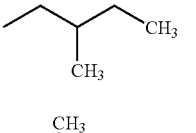 | Me | H |
| 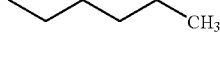 | Me | H |
| 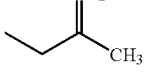 | Me | H |
| 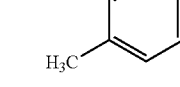 | Me | H |
| 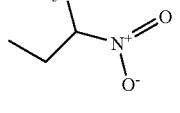 | Me | H |
| 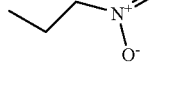 | Me | H |
| 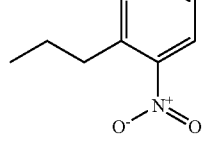 | Me | H |
| 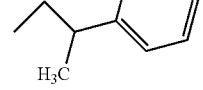 | Me | H |

-continued

| R₄ | R₅ | R₆ |
|---|---|---|
| (1-propyl-1-(methylthio)butyl group: CH(CH₂CH₂CH₃)(CH₂CH₂CH₃) with SCH₃) | Me | H |
| butyl-S-CH₃ | Me | H |
| 4-propyl-2-methoxy-1-ethoxybenzene | Me | H |
| 2,3-dimethylpentyl | Me | H |
| 2-nitrobutyl (CH(CH₃)CH₂ with NO₂) | Me | H |
| 1-ethylpropyl phenyl (3-phenylpentan-3-yl) | Me | H |
| 1-methoxy-1,2-diphenylpropyl | Me | H |
| 2-isopropyl-1-(trifluoromethyl)phenyl | Me | H |
| 2-ethylpyrrolidine | Me | H |
| butyl methacrylate | Me | H |
| methyl 2-methylbutanoate | Me | H |

-continued

| R₄ | | R₅ | R₆ |
|---|---|---|---|
| farnesyl-type chain (CH₃CH₂–C(CH₃)=CH–CH₂–CH₂–C(CH₃)=CH–CH₂–CH₂–C(CH₃)=CH–CH₃) | | Me | H |
| CH₃CH₂CH₂–N(CH(CH₃)₂)₂ (N,N-diisopropylpropylamine) | | Me | H |
| CH₃CH₂–CH=CH–CH₂–CH₂–CH₃ | | Me | H |

| R₄ | R₅ | R₆ |
|---|---|---|
| Me | (S)-1-bromo-2-methylbutyl (CH₃CH₂CH(CH₃)CH₂Br) | H |
| Me | propyl-aziridine (CH₃CH₂CH₂–N(aziridinyl)) | H |
| Me | –(CH₂)₁₁CH₃ (dodecyl) | H |
| Me | –(CH₂)ₙBr (long-chain bromoalkyl) | H |
| Me | pentafluorophenyl-ethyl (–CH₂CH₂–C₆F₅) | H |
| Me | 2-(2-thienyl)propyl | H |
| Me | 3-(3-thienyl)propyl | H |
| Me | 2-(2-fluorophenyl)propyl | H |
| Me | 2-(2-pyridyl)butyl | H |
| Me | 2-(2-thienyl)ethyl | H |

-continued
| R4 | R5 | R6 |
|---|---|---|
| Me | 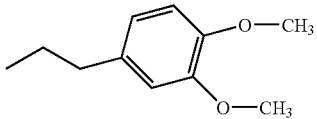 | H |
| Me | 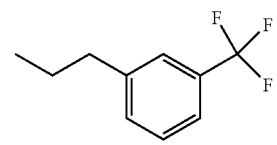 | H |
| Me |  | H |
| Me | 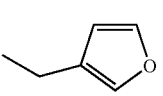 | H |
| Me | 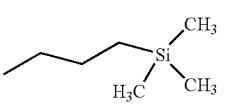 | H |
| Me | 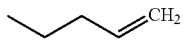 | H |
| Me | 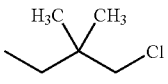 | H |
| Me | 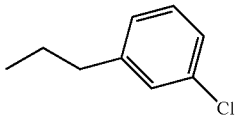 | H |
| Me | 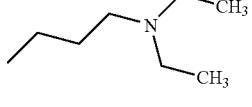 | H |
| Me | 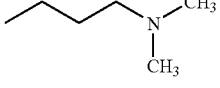 | H |
| Me | 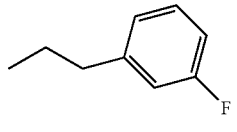 | H |
| Me | 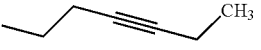 | H |
| Me | 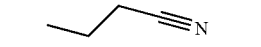 | H |
| Me | 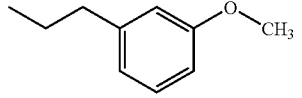 | H |
| Me | 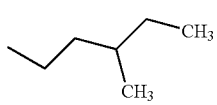 | H |

-continued
| R$_4$ | R$_5$ | R$_6$ |
|---|---|---|
| Me | 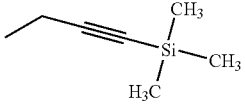 | H |
| Me | 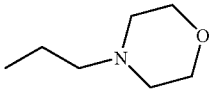 | H |
| Me | 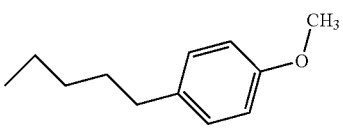 | H |
| Me | 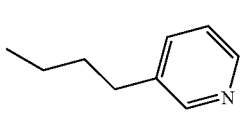 | H |
| Me | 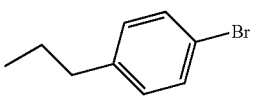 | H |
| Me | 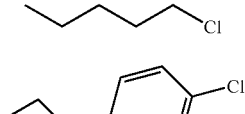 | H |
| Me | 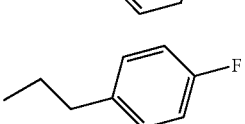 | H |
| Me | 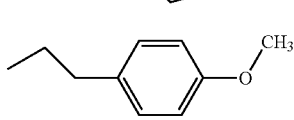 | H |
| Me | 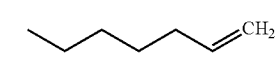 | H |
| Me | 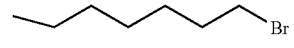 | H |
| Me | 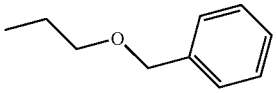 | H |
| Me | 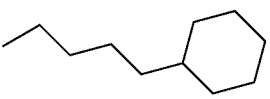 | H |
| Me | 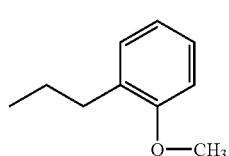 | H |
| Me | 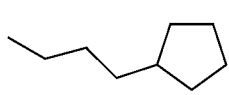 | H |
| Me |  | H |

| R₄ | R₅ | R₆ |
|---|---|---|
| Me | CH₃CH₂-C≡C-CH₃ | H |
| Me | -CH₂CH₂-(2-naphthyl) | H |
| Me | -CH₂CH₂CH₂CH₂-C≡C-CH₂CH₂CH₂CH₃ | H |
| Me | -(CH₂)₅-(4-nitrophenyl) | H |
| Me | -CH₂CH₂CH₂-(4-methyl-5-thiazolyl) | H |
| Me | -CH₂CH₂CH₂-(4-methylphenyl) | H |
| Me | -CH₂CH₂CH₂-(4-nitrophenyl) | H |
| Me | -CH₂CH₂CH₂CH₂CH=CH₂ | H |
| Me | -(CH₂)₅-phenyl | H |
| Me | -(CH₂)₄-(4-pyridyl) | H |
| Me | -(CH₂)₆-phenyl | H |
| Me | -(CH₂)₄-(6-methyl-2-pyridyl) | H |
| Me | -CH₂CH₂-C(=O)-CH₃ | H |
| Me | -CH₂CH₂-CH=CH-phenyl | H |

-continued
| R$_4$ | R$_5$ | R$_6$ |
|---|---|---|
| Me | 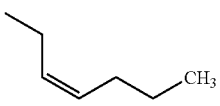 | H |
| Me | 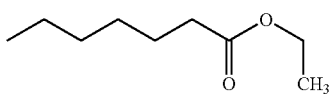 | H |
| Me | 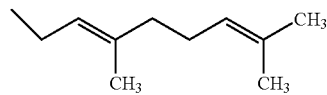 | H |
| Me | 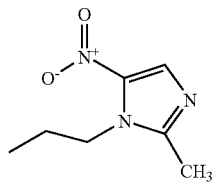 | H |
| Me | 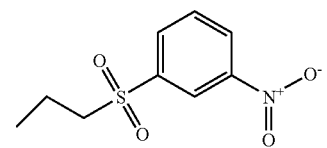 | H |
| Me | 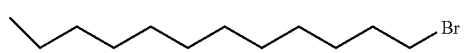 | H |
| Me | 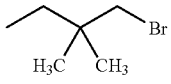 | H |
| Me | 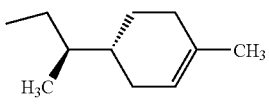 | H |
| Me | 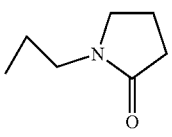 | H |
| Me | 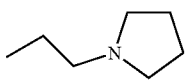 | H |
| Me | 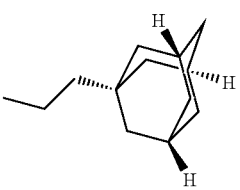 | H |
| Me | 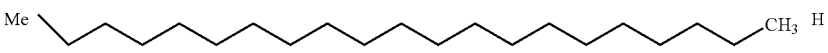 | H |

-continued
| R₄ | R₅ | R₆ |
|---|---|---|
| Me | 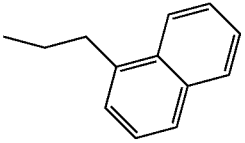 | H |
| Me | 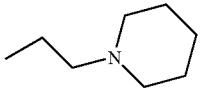 | H |
| Me | 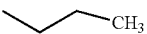 | H |
| Me | 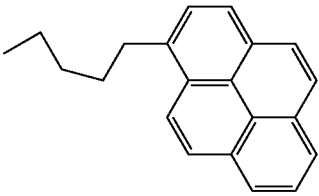 | H |
| Me | 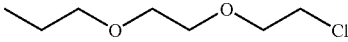 | H |
| Me | 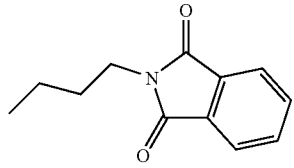 | H |
| Me | 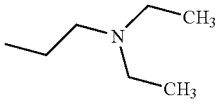 | H |
| Me | 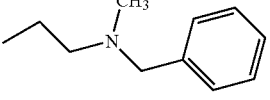 | H |
| Me |  | H |
| Me | 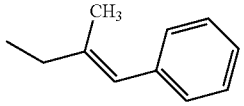 | H |
| Me | 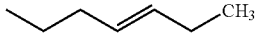 | H |
| Me | 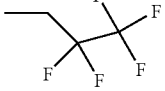 | H |
| Me |  | H |

-continued

| R$_4$ | R$_5$ | R$_6$ |
|---|---|---|
| Me | 3,7-dimethylocta-2,6-dienyl (geranyl-like) | H |
| Me | 2,2-dimethylbutanal | H |
| Me | pentyl acrylate | H |
| Me | 3-ethylhexyl | H |
| Me | 3-methylpentyl | H |
| Me | (2,3,6-trifluorophenoxy)propyl | H |
| Me | 2-(2-chloroethoxy)ethyl | H |
| Me | 2-propylpyridine | H |
| Me | 2-(3-propoxypropyl)-6-methylpyridine | H |
| Me | 4-bromophenoxypropyl | H |
| Me | N-butyl-N-pentylpropylamine | H |
| Me | propyl methyl sulfone | H |
| Me | propyl methyl sulfide | H |

-continued

| R₄ | R₅ | R₆ |
|---|---|---|
| Me | 3-(N-ethyl-N-propylamino)toluene group | H |
| Me | propylsulfonylbenzene group | H |
| Me | propylthiobenzene group | H |
| Me | propyltrimethylsilyl group | H |
| Me | 3,3,3-trifluoropropyl group | H |
| Me | 3-methyl-2-pentanone group | H |
| Me | 3-propyl-nitrobenzene group | H |
| Me | butyl-O-CH₂CH₂-O-CH₃ group | H |
| Me | nonenyl group | H |
| Me | 3-methyl-5,5-dimethylhexyl (branched) group | H |
| Me | 4-phenylbutyl group | H |
| Me | phytyl-like polyisoprenoid group | H |
| Me | 3,7-dimethyl-oct-6-enyl group | H |

-continued

| R₄ | R₅ | R₆ |
|---|---|---|
| Me | methyl 2,2-dimethylbutanoate group | H |
| Me | 2-methyl-2-pentenyl group | H |
| Me | 2-methylenepentyl group | H |
| Me | 3-methylphenylpropyl group | H |
| Me | 2-pentynyl group | H |
| Me | perfluoropentyl-ethyl group | H |
| Me | 6H-perfluorohexyl-ethyl group | H |
| Me | 3,3,4,4-tetrafluorobutyl group | H |
| Me | 1,1-diphenylpropyl group | H |
| Me | 3,5,5-trimethyl-4-methylheptyl group | H |
| Me | 3,5-dimethyl-2,7-octadienyl group | H |
| Me | 3-chloropropyl group | H |

-continued
| R₄ | R₅ | R₆ |
|---|---|---|
| Me | 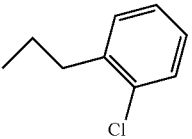 | H |
| Me | 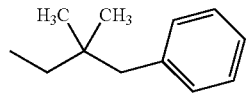 | H |
| Me | 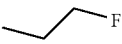 | H |
| Me | 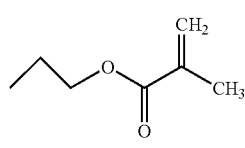 | H |
| Me | 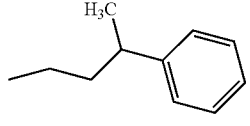 | H |
| Me | 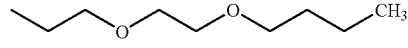 | H |
| Me | 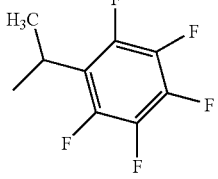 | H |
| Me | 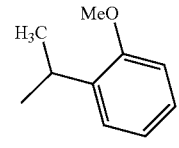 | H |
| Me | 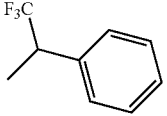 | H |
| Me | 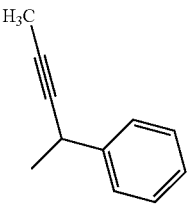 | H |
| Me | 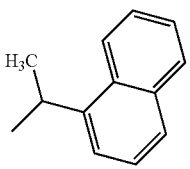 | H |

-continued

| R₄ | R₅ | R₆ |
|---|---|---|
| Me | 1-(1,3-dichloro-substituted)... 2-chloro-1-methylethyl group on 2,4-dichlorophenyl | H |
| Me | 1-methylethyl on 4-fluorophenyl | H |
| Me | 1-methylethyl on 4-methoxyphenyl | H |
| Me | 2-methyl-3-phenylpropyl | H |
| Me | isopropoxypropyl | H |
| Me | 2,3-dimethylbutyl | H |
| Me | 3-methylhexyl | H |
| Me | 2-methylbut-1-en-yl | H |
| Me | 3-(2-methylphenyl)propyl | H |
| Me | 2-nitrobutan-2-yl | H |
| Me | 1-nitropropyl | H |
| Me | 3-(2-nitrophenyl)propyl | H |

-continued
| R₄ | R₅ | R₆ |
|---|---|---|
| Me | 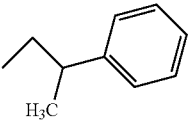 | H |
| Me | 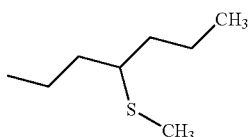 | H |
| Me | 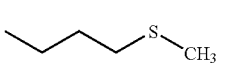 | H |
| Me | 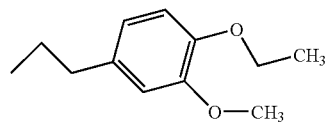 | H |
| Me | 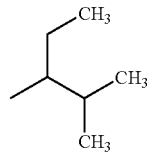 | H |
| Me | 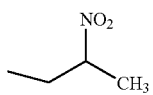 | H |
| Me | 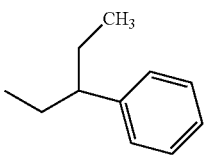 | H |
| Me |  | H |
| Me | 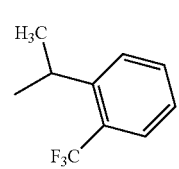 | H |
| Me | 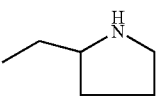 | H |
| Me | 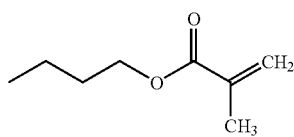 | H |

-continued

| R$_4$ | R$_5$ | R$_6$ |
|---|---|---|
| Me | 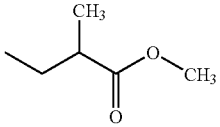 | H |
| Me | 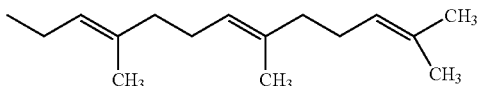 | H |
| Me | 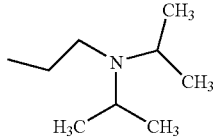 | H |
| Me | 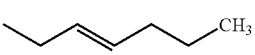 | H |

Accordingly, the present invention includes within its scope pharmaceutical compositions comprising, a pharmaceutically acceptable carrier and an active ingredient comprising: (1) a biological/immune response modifier or anti-inflammatory agent (e.g., small molecule, antibody, peptide or gene therapy reagent) that effectively blocks autoimmune response in a mammal by inhibiting the activity or expression of inflammatory cytokines such as, for example, IL-12, IL-23 or IL-27, or members of the Signal Transducers and Activators of Transcription (STAT) family, preferably STAT-4, which are believed to be regulators of T cell differentiation involved in immune responses, alone or in combination with (2) a compound or agent (small molecule or peptide) that facilitates growth and/or differentiation of pancreatic β-cells or any insulin producing cell, either alone or in admixture with a diluent or in the form of a medicament.

In addition to LSF, and the above-described LSF analogs, additional biological/immune response modifying or anti-inflammatory compounds or agents preferred for use in accordance with the principles of the present invention include, without limitation, members of the group consisting of the compounds (LSF analogs) described in the following U.S. patents, the entire disclosures or which are incorporated herein by reference:

| U.S. Pat No. | Title |
|---|---|
| 5,585,380 | Modulation of Cellular Response to External Stimuli |
| 5,648,357 | Enantiomerically Pure Hydroxylated Xanthine Compounds |
| 5,652,243 | Methods of Using Enantiomericallly Pure Hydroxylated Xanthine Compounds |
| 5,612,349 | Enantiomerically Pure Hydroxylated Xanthine Compounds |
| 5,567,704 | R-Enantiomerically Pure Hydroxylated Xanthine Compounds To Treat Baldness |
| 5,580,874 | Enantiomerically Pure Hydroxylated Xanthine Compounds |
| 5,739,138 | Enantiomerically Pure Hydroxylated Xanthine Compounds To Treat Autoimmune Diabetes |
| 5,792,772 | Enantiomerically Pure Hydroxylated Xanthine Compounds |
| 5,620,984 | Enantiomerically Pure Hydroxylated Xanthine Compounds |
| 5,580,873 | Enantiomerically Pure Hydroxylated Xanthine Compounds To Treat Proliferative Vascular Diseases |
| 5,629,315 | Treatment of Diseases Using Enantiomerically Pure Hydroxylated Xanthine Compounds |
| 5,621,102 | Process for Preparing Enantiomerically Pure Xanthine Derivatives |
| 5,965,564 | Enantiomerically Pure Hydroxylated Xanthine Compounds |
| 5,629,423 | Asymmetric Synthesis of Chiral Secondary Alcohols |
| 6,780,865 | Compounds Having Selective Hydrolytic Potentials |
| 6,057,328 | Method for Treating Hyperoxia |
| 6,469,017 | Method of Inhibiting Interleukin-12 Signaling |
| 5,288,721 | Substituted Epoxyalkyl Xanthines for Modulation of Cellular Response |
| 5,866,576 | Expoxide-Containing Compounds |
| 6,121,270 | Epoxide-Containing Compounds |
| 5,340,813 | Substituted Aminoalkyl Xanthines Compounds |
| 5,817,662 | Substituted Amino Alkyl Compounds |
| 5,889,011 | Substituted Amino Alkyl Compounds |
| 6,103,730 | Amine Substituted Compounds |
| 5,801,182 | Amine Substituted Compounds |
| 5,807,861 | Amine Substituted Compounds |
| 5,473,070 | Substituted Long Chain Alcohol Xanthine Compounds |
| 5,804,584 | Hydroxyl-Containing Compounds |
| 5,780,476 | Hydroxyl-Containing Compounds |
| 6,133,274 | Hydroxyl-Containing Bicyclic Compounds |
| 6,693,105 | Hydroxyl-Containing Compounds |
| 6,075,029 | Modulators of Metabolism |
| 5,670,506 | Halogen, Isothiocyanate or Azide Substituted Compounds |
| 6,020,337 | Electronegative-Substituted Long Chain Xanthine Compounds |
| 5,795,897 | Oxohexyl Methylxanthine Compounds |
| 5,770,595 | Oxime Substituted Therapeutic Compounds |
| 5,929,081 | Method for Treating Diseases Mediated by Cellular Proliferation in Response to PDGF, EGF, FGF and VEGF |
| 5,859,018 | Method for Treating Diseases Mediated by Cellular Proliferation in Response to PDGF, EGF, FGF and VEGF |
| 5,795,898 | Method for Treating Diseases Mediated by Cellular Proliferation in Response to PDGF, EGF, FGF and VEGF |
| 6,100,271 | Therapeutic Compounds Containing Xanthinyl |
| 5,807,862 | Therapeutic Compounds |
| 6,043,250 | Methods for Using Therapeutic Compounds Containing Xanthinyl |
| 6,774,130 | Therapeutic Compounds for Inhibiting Interleukin-12 Signaling and Methods for Using Same |
| 6,878,715 | Therapeutic Compounds for Inhibiting Interleukin-12 Signaling and Methods for Using Same |

-continued

| U.S. Pat No. | Title |
|---|---|
| 6,586,429 | Tricyclic Fused Xanthine Compounds and Their Uses (As Amended) |

Still further, additional biological/immune response modifying (immunomodulating) or anti-inflammatory compounds or agents that may be for used in accordance with the principles of the present invention include, without limitation, members of the group consisting of the following cytokine formation blocking agents or methods: SiRNA (small interfering RNA); mTOR (mammalian target of Rapamycin); Leflunomide and active metabolites (e.g., A77 1726, LEF M); blockers of formation of advance glycation end products or small molecule or antibodies that inhibit the receptor for advance glycation end products (RAGE); Lipoxins or analogs thereof (e.g., LXA4); small molecule inhibitors of IL-12 (e.g., STA-S326, Synta Pharmaceuticals); monoclonal antibodies (e.g., anti-interleukin-12 monoclonal antibody (ABT-874, Abbott Laboratories); various methods for inhibiting cytokines described in Vanderbroeck, K., et al., "Inhibiting Cytokines of the Interleukin-12 Family: Recent Advances and Novel Challenges," *Journal of Pharmacy and Pharmacology*, 56:145-160 (2004), and the like.

The dosage of active ingredient in the pharmaceutical compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses. Preferably the therapeutic amount is between about 0.5 mg to about 12 mg, and more preferably between about 2 mg to about 8 mg, with the most preferred dosage being between about 2 mg and about 6 mg. Unit dosage forms are preferred.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern. Suitable dosages are well known or readily determinable by the skilled artisan. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

To practice the method of the present invention, the pharmaceutical compositions of the present invention can be administered by oral, parenteral (e.g., intramuscular, intraperitoneal, intravenous or subcutaneous injection, or implant), by inhalation spray, nasal, buccal, vaginal, rectal, implanted reservoir, sublingual or topical routes of administration and can be formulated with pharmaceutically acceptable carriers to provide dosage forms appropriate for each route of administration. The term "parenteral" as used herein includes subcutaneous, intracutaneous, intravenous, intramuscular, intraarticular, intraarterial, intrasynovial, intrastemal, intrathecal, intralesional and intracranial injection or infusion techniques. Any method of the present invention can comprise administering an effective amount of a composition or pharmaceutical composition comprising (1) a biological/immune response modifier or anti-inflammatory agent (e.g., small molecule, antibody, peptide or gene therapy reagent) that effectively blocks autoimmune response or cytokine formation in a mammal (e.g., Lisofylline (LSF) and structurally related LSF analogs, as further described below), alone or in combination with (2) any compound or agent (e.g., small molecule or peptide) (e.g., Ex-4) that facilitates growth and/or differentiation of pancreatic β-cells or any insulin producing cell.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The composition of the present invention may include also conventional excipients of the type used in pharmaceutical compositions. For example, the composition may include pharmaceutically acceptable organic or inorganic carriers suitable for oral administration. Examples of such carriers include: sugar spheres, diluents, hydrophilic polymers, lubricants, glidants (or anti-adherents), plasticizers, binders, disintegrants, surfactants and pH modifiers.

Suitable diluents include microcrystalline cellulose, lactose, sucrose, fructose, glucose dextrose, or other sugars, dibasic calcium phosphate, calcium sulphate, cellulose, ethylcellulose, cellulose derivatives, kaolin, mannitol, lactitol, maltitol, xylitol, sorbitol, or other sugar alcohols, dry starch, dextrin, maltodextrin or other polysaccharides, inositol or mixtures thereof.

Suitable hydrophilic polymers include hydroxypropylmethyl cellulose, carbomers, polyethylene oxides, hydroxypropyl cellulose, hydroxyethyl cellulose, carboxymethylcellulose, sodium carboxymethylcellulose, carboxyvinylpolymers, polyvinyl alcohols, glucans, scleroglucans, mannans, xanthans, carboxymethylcellulose and its derivatives, methylcellulose and, in general, cellulose, crosslinked polyvinylpyrrolidone, carboxymethyl starch, potassium methacrylate-divinylbenzene copolymer, hydroxypropylcyclodextrin, alpha, beta, gamma cyclodextrin or derivatives and other dextran derivatives, natural gums, seaweed extract, plant exudate, agar, agarose, algin, sodium alginate, potassium alginate, carrageenan, kappa-carrageenan, lambda-carrageenan, fucoidan, furcellaran, laminarin, hypnea, eucheuma, gum arabic, gum ghatti, gum karaya, gum tragacanth, guar gum, locust bean gum, quince psyllium, flax seed, okra gum, arabinogalactin, pectin, scleroglucan, dextran, amylose, amylopectin, dextrin, acacia, karaya, guar, a swellable mixture of agar and carboxymethyl cellulose; a swellable composition comprising methyl cellulose mixed with a sparingly cross-linked agar; a blend of sodium alginate and locust bean gum; and the like.

Suitable glidants (or anti-adherents) include colloidal silica, fumed silicon dioxide, silica hydrogel, talc, fumed silica, gypsum, kaolin and glyceryl monostearate.

Suitable plasticizers include acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, glyceryl monocaprate.

Suitable binders include starches, hydroxypropylmethyl cellulose, hydroxypropyl cellulose, ethyl cellulose, polyvinyl pyrrolidone, acacia, guar gum, hydroxyethylcellulose, agar, calcium carrageenan, sodium alginate, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arbolactan, polyethylene glycols, waxes and mixtures thereof.

Suitable disintegrants include starches, sodium starch glycollate, crospovidone, croscarmellose, microcrystalline cellulose, low substituted hydroxypropyl cellulose, pectins, potassium methacrylate—divinylbenzene copolymer, polyvinylalcohol, thylamide, sodium bicarbonate, sodium carbonate, starch derivatives, dextrin, beta cyclodextrin, dextrin derivatives, magnesium oxide, clays, bentonite and mixtures thereof.

Suitable surfactants include nonionic surfactants such as sorbitan sesquioleate, polyoxyethylene sorbitan monooleate, polyoxyethylene monostearate, glycerol monostearate, propylene glycol monolaurate, polyoxyethylene lauryl ether, polyoxyethylene cetyl ether or polyoxyethylene hydrogenated castor oil; and ionic surfactants such as sodium dodecyl sulfate or benzalkonium chloride; and the like.

Suitable pH modifiers include organic acids such as citric acid, fumaric acid, tartaric acid, succinic acid, ascorbic acid, acetic acid, malic acid, glutaric acid and adipic acid; salts of these acids; salts of inorganic acids and magnesium hydroxide.

In general, it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg of body weight per day, to achieve effective results. Nevertheless, it can at times be necessary to deviate from those dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

Article of Manufacture

In another aspect, the present invention provides an article of manufacture in accordance with the present invention comprises a means for holding an pharmaceutical composition, as previously described, suitable for administration to a patient in combination with printed labeling instructions providing a discussion of when or how a particular dosage form should be administered to the patient. The pharmaceutical composition will be contained in any suitable means or container capable of holding and dispensing the dosage form and which will not significantly interact with the composition and will further be in physical relation with the appropriate labeling advising that the dosage form exhibits an ability, or may be used, to restore β-cell mass and function in a mammal in need thereof. The labeling instructions will be consistent with the methods of treatment as described hereinbefore. For example, the labeling may be associated with a container by any means that maintain a physical proximity of the two. Further, by way of non-limiting example, they may both be contained in a packaging means such as a box or plastic shrink wrap or may be associated with the instructions being bonded to container such as with glue or adhesive that does not obscure the labeling instructions or other bonding or holding means.

The present invention will be further illustrated in the following, non limiting Examples. The Examples are illustrative only and do not limit the claimed invention regarding the materials, conditions, process parameters and the like recited herein.

EXPERIMENTAL DESCRIPTION FOR EXAMPLES

For in vitro studies (Examples 1-3), freshly isolated BALB/c pancreatic islets were incubated at 37° C. with either LSF (50 μM) alone, Ex-4 (20 nM) alone, or with LSF/Ex-4 combined. After 3 days of culture, islets were treated with or without pro-inflammatory cytokines (10 ng/mL IL-1β, 20 ng/mL TNF-α, and 100 ng/mL IFN-γ) overnight. Insulin secretion was measured in low and high glucose using a standard elisa method for mouse insulin. Apoptotic islets were quantitatively assessed. MTT assay was used to evaluate cell metabolism and mitochondrial function.

Example 1

This Example demonstrates that both Ex-4 and LSF have an ability to increase insulin release upon glucose stimulation in vitro. The addition of Ex-4 and LSF together did not further stimulate insulin secretion suggesting tht these two agents could be safely used together and would not produce hypoglycemia. (See FIG. 1 in which "*" and "^" indicate P<0.005 compared to "none" treatment group).

Example 2

LSF and Ex-4 Combined Leads to Enhanced Protection of Islets from Pro-Inflammatory Cytokine Cell Death Cellular death (apoptosis) was quantified using an established method in mouse islets exposed to pro-inflammatory cytokines.

Figure 2:
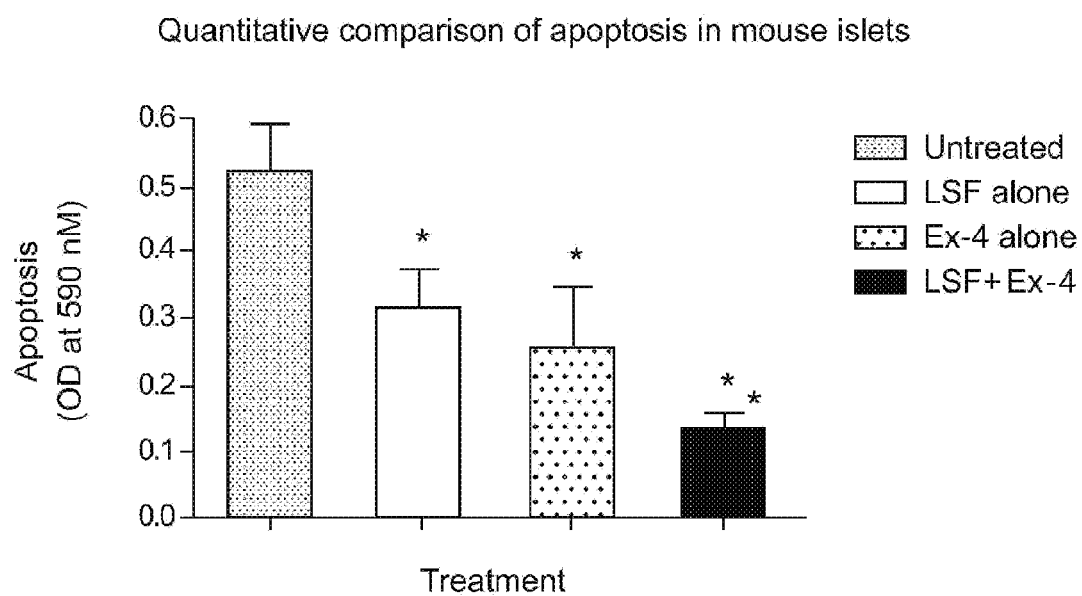
FIG. 2 depicts the effect in apoptosis reduction in isolated mouse islets after individual and combined treatment of LSF and Ex-4 in vitro.
Figure 3:
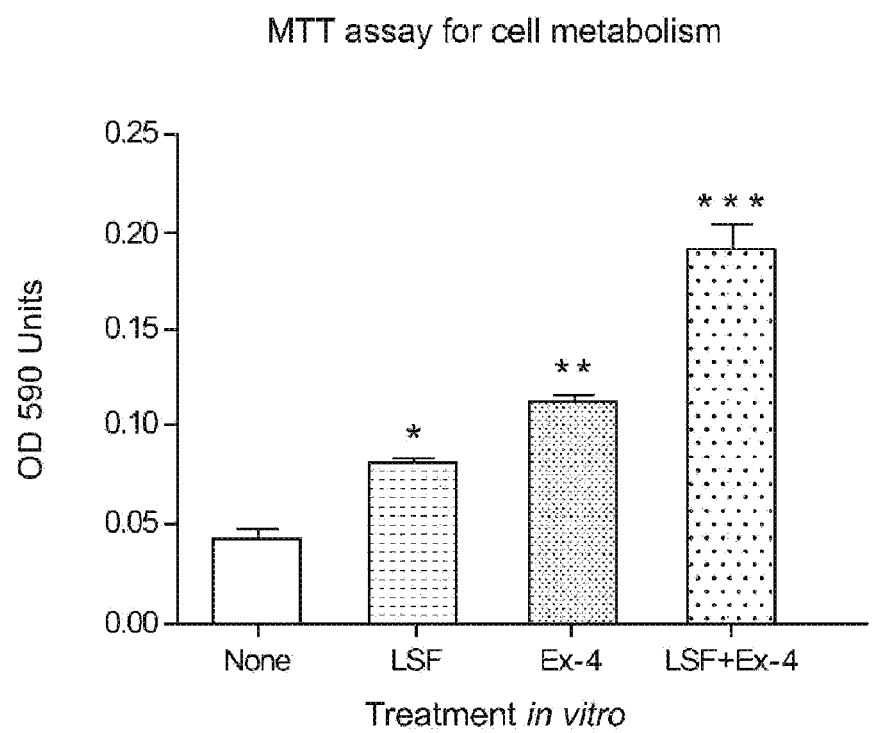
FIG. 3 depicts the effect of mitochondrial metabolism (as reflected by level of MTT metabolite) observed in isolated mouse islets after individual and combined treatment with LSF and Ex-4.

FIG. 2 shows that both LSF and Ex-4 alone could protect isolated islet cells from pro-inflammatory cytokines (e.g. IL-1β, TNF-α and IFN-γ). A synergism in apoptosis reduction in β-cells was observed after combined treatment with Ex-4 and LSF in vitro (P<0.005) (40 percent reduction)

Example 3

LSF and Ex-4 Increases β-cell Metabolism

LSF showed an ability to enhance the metabolism in β-cells. We previously published, in murine β-cell lines and human islets that both ATP production and mitochondrial metabolism (MTT metabolite levels) were increased by LSF treatment. In this Example, Ex-4 and LSF alone exhibited an ability to increase mitochondrial metabolism in mouse islets, but the combination of LSF and Ex-4 produced a significant increase in mitochondrial metabolism compared to either drug alone. Ex-4/LSF treatment enhanced β-cell metabolism (2.2-2.5 fold).

In sum, both LSF and Ex-4 displayed the ability to increase insulin release upon glucose stimulation. LSF or Ex-4 alone protected islets and β-cells from pro-inflammatory cytokine damage, however the combined treatment of LSF/Ex-4 was significantly more effective. Ex-4 and LSF alone can increase mitochondrial metabolism in mouse islets, but combined treatment shows a significant increase in mitochondrial metabolism over both the control and treatments individually.

Example 4

LSF And Ex-4 Combined Therapy Reversed Type 1 Diabetes in an Established Mouse Model Pre-diabetic non-obese diabetic (NOD) mice were monitored until two consecutive blood glucose readings within a week were above 250 mg/dL. This indicated the animals had already become diabetic. At this point a mini-osmotic pump was filled with one of the following and implanted subcutaneously:

Normal saline (control)
Ex-4
LSF
Ex-4 and LSF

Blood glucose levels in these mice were monitored, and a small dose of insulin was administered to the hyperglycemic mice to maintain euglycemia for the first few days. The pump was removed after 28 days, discontinuing treatment with the drug; however, the blood glucose levels were continually monitored for several more weeks. These mice were then sacrificed, and slide sections were prepared from their pancreases to evaluated histology and insulin staining (Example 5) and evidence for growth the new beta cells (Example 6).

Figure 4:
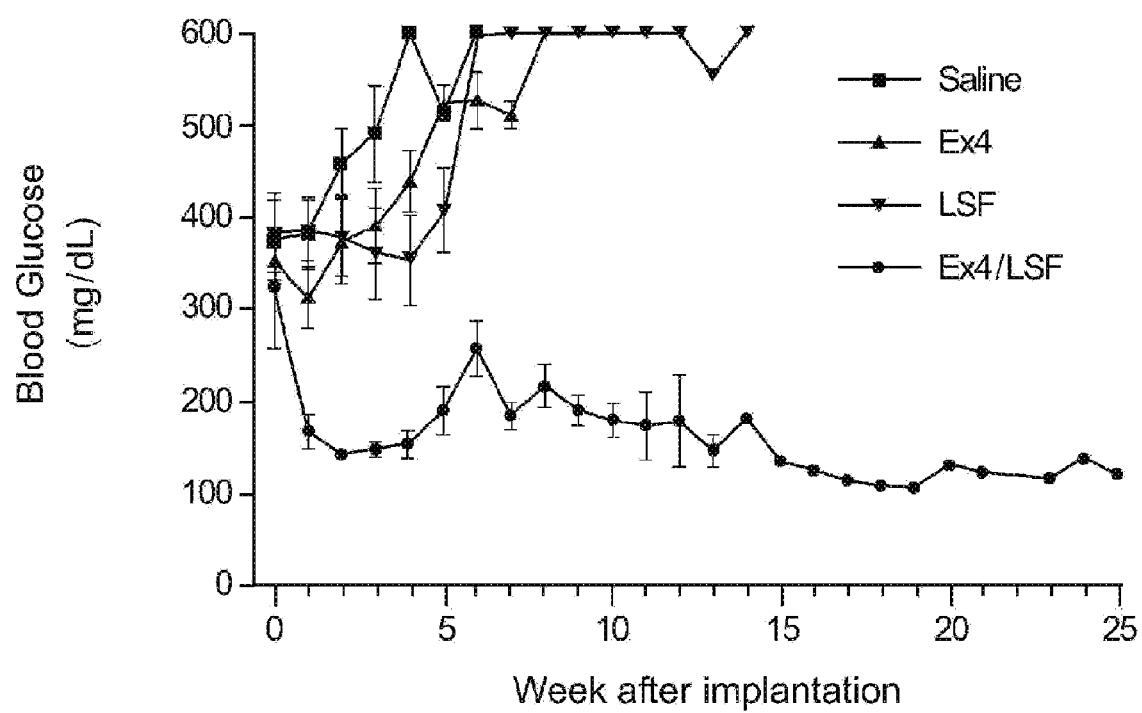
FIG. 4 depicts average levels of blood glucose in 4 NOD mice groups treated with saline (control), Ex-4 alone, LSF alone and LSF and Ex-4 combined, respectively.

The combined therapy with LSF (27 mg/kg/day) and Ex-4 (18 nM/day) by constantly subcutaneous (S.C.) administration using osmotic mini-pumps (Alzet Model 2002, DURECT Cor. Cupertino, Calif.) reversed diabetes in newly diagnosed NOD mice. These NOD were spontaneously diabetic between 20-25 weeks of age. The control groups include normal saline, LSF alone (27 mg/kg/day) and Ex-4 alone (18 nM/day). The blood glucose levels in mice were monitored daily, and the levels of average reading in each group are shown in FIG. 4, which shows average levels of blood glucose in each mouse group. Four mice were in each group. Diabetes reversal was seen within 2-3 days after implantation of LSF/Ex-4 pumps, while hyperglycemia was controlled 10-12 days after LSF alone pump therapy. Ex-4 alone showed no effective diabetes control in NOD mice. After termination of the 28-day pump therapy, euglycemia remained in NOD mice that had been treated with LSF plus Ex-4, and LSF alone. These results provide evidence that combined LSF and Ex-4 treatment can reverse established diabetes in the NOD mouse, an accepted rodent model of Type 1 diabetes.

Example 5

Figure 5:
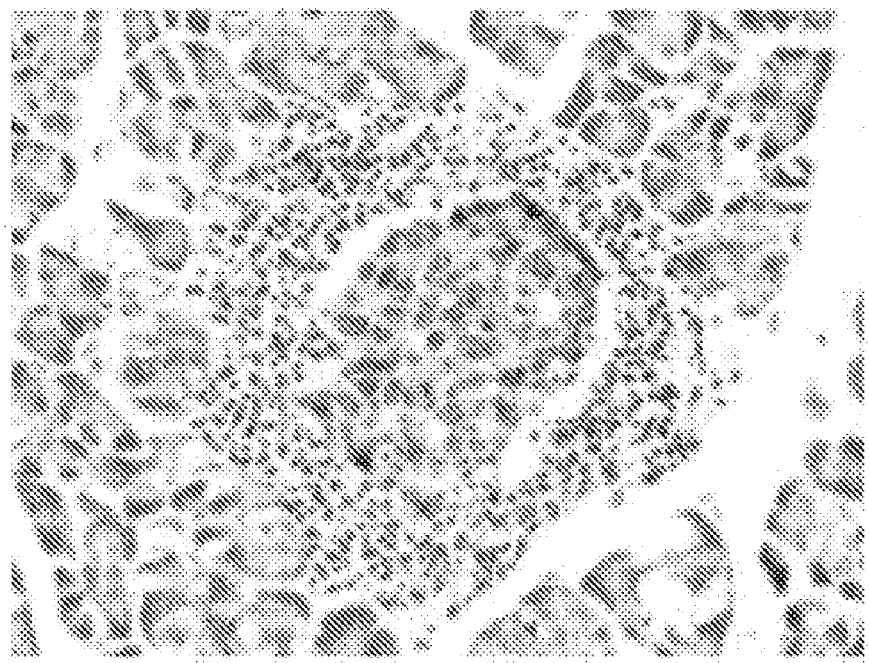
FIG. 5 depicts immunochemistry of insulin in NOD mouse pancreatic sections untreated and treated with LSF and Ex-4.
Figure 5:
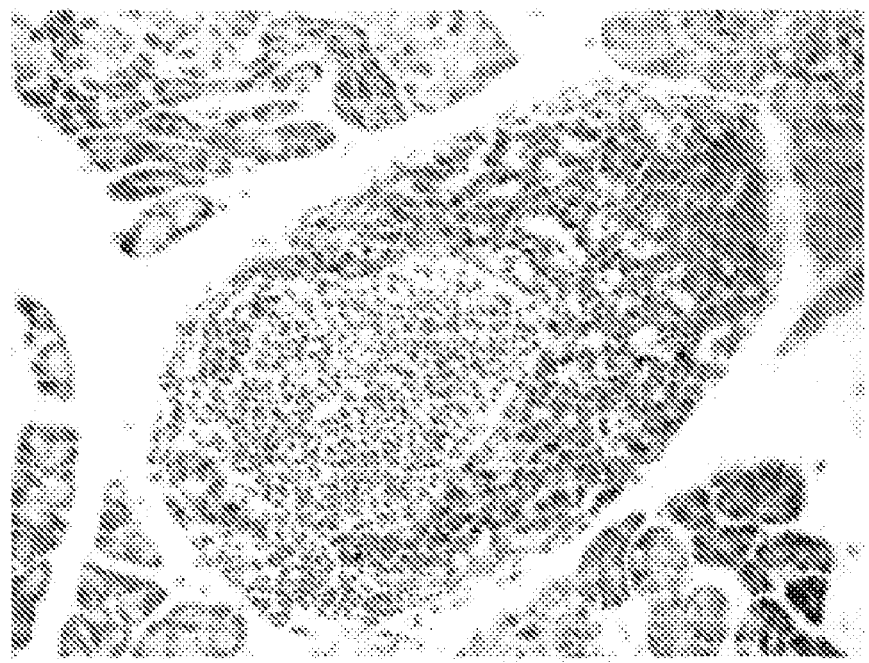

LSF Plus Ex-4 Led to New Positive Insulin Staining in Pancreatic Sections of Previously Diabetic NOD Mice Pancreata were fixed and stained with an anti-insulin antibody. Once can see in FIG. 5 very little insulin remaining in the control diabetic pancreas and many inflammatory cells destroying the islets. However, the Ex-4/LSF animal with diabetes reversed showed many insulin positive cells and those insulin-positive cell clusters seem ductal in origin.

Example 6

Evidence of New Beta Cell Growth in Ex4/LSF Treated NOD Mice

Figure 6:
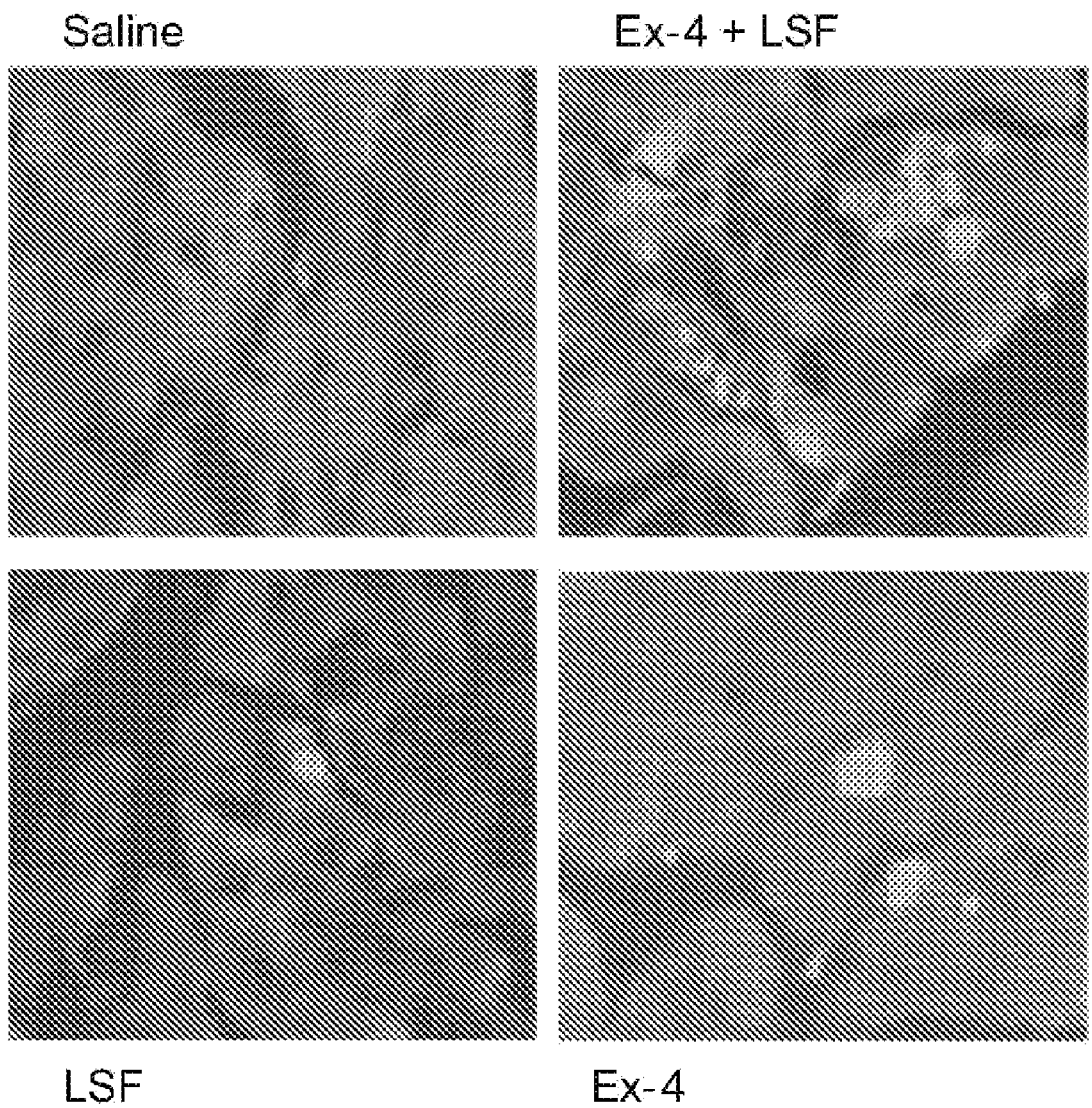
FIG. 6 depicts results of Brdu staining of NOD mouse pancreatic sections treated with saline (control), Ex-4 alone, LSF alone and LSF and Ex-4 combined, respectively.

Ex-4/LSF-associated cell proliferation in vivo was evaluated. Diabetic NOD mice that were treated with Ex-4 alone, Ex-4 plus LSF, LSF alone and normal saline for 28 days via mini-pumps were injected with Brdu (50 mg/kg) I.P. 24 hours later, pancreatic tissues were collected and stained with an anti-Brdu antibody. FIG. 6 shows Brdu-positive cells were detected in those mice that had LSF alone, Ex-4 alone and Ex-4 plus LSF therapies, but not seen in mice treated with saline. Significantly, most Brdu-positive cells were found in islet-like clusters in the Ex-4/LSF combined animals that also were positive for insulin.

In mammals, the pancreas begins as a dorsal and a ventral bud, both of which form from the embryonic endodermal layer through the regulation of activin and fibroblast growth factor (FGF) from the notochord. Eventually, the two buds fuse into the single organ that is present in adult mammals, and the endocrine portion of the pancreas is clearly differentiated into α, β, δ, and PP cells that secrete glucagon, insulin, somatostatin, and pancreatic polypeptide, respectively. This process of differentiation requires many transcriptional signals from the mesenchyme, the tissue surrounding the notochord and pancreas. Before differentiation can occur, the endoderm needs to be patterned properly. The forkhead box factors Foxa1 and Foxa2 are found in the early endodermal tissue, and are believed to be involved in this patterning. Foxa2, specifically, is believed to be essential to this process, as its deletion in mice results in sever disruption of the endodermal formation.

After the endodermal patterning, morphogenesis begins and the two pancreatic buds are formed. The two transcriptions factors that seem to regulate this process are both in the homeobox class—they share a highly conserved 60-amino acid sequence called the homeobox or homeodomain that acts as the DNA-binding domain (DBD). The first, pancreatic and duodenal homeobox factor 1 (Pdx1), is synthesized in the entire mass that later develops into the two pancreatic buds. Pdx1 plays a key role in the very early development of the pancreatic tissue: its deletion in mice causes the complete lack of a pancreas in the adult. Pre-B-cell leukemia transcription factor 1 (Pbx1) interacts with a specific amino acid sequence in the middle of Pdx1, and this interaction is believed to be important in triggering Pdx1's morphogenetic effect. Once the pancreatic tissue has been formed, the differentiation between endocrine and nonendocrine (ductal or exocrine) cells occurs. Cells that express neurogenin 3 (Ngn3) differentiate into endocrine cells; those that express hairy and enhancer of split 1 (Hes1), a repressor of Ngn3 expression, become exocrine or duct cells. The transcription factor neurogenic differentiation 1 (NeuroD1) is also believed to play a role in this process. Its deletion in mice does not prevent exocrine differentiation altogether, but it causes islet growth to be arrested very early in development; therefore, NeuroD1 is believed to lie immediately downstream of Ngn3 in the differentiation program for endocrine cells.

The differentiation between α- and β-cells is directed by a pair of homeobox transcription factors called Pax4 and Pax6. Pax4 expression is believed to commit cells towards the δ- and β-cell paths, as the deficiency of Pax4 in mice results in the failure of development of those two cell types; Pax6 deficiency causes the absence of α-cells, leading researchers to believe that Pax6-expressing cells develop into α-cells. The final differentiation of the β-cells is directed by the NK homeobox factors Nkx2.2 and Nkx6.1. Disruption of Nkx6.1 in mice results in a scarcity of β-cells while other cell types are present in usual numbers; the deficiency of Nkx2.2 in mice leads to a complete lack of insulin-producing β-cells.

In view of the above, mice treated with the combination of Ex4 and LSF should feature higher levels of expression of the transcription factors involved in the differentiation of pancreatic β-cells than control mice and mice treated with Ex4 or LSF individually.

Immunohistochemical Staining

Immunohistochemical staining was performed on the previously obtained sections of pancreas using antibodies for the following hormones and transcription factors at the concentrations noted below:

Insulin (1:50)
Glucagon (1:50)
Pdx1 (1:2000)
Ngn3 (1:250 and 1:500)
Nkx6.1 (1:600 and 1:6000)

The exciting data results show that the Brdu-positive cells in the combined Ex-4/LSF treated NOD mice are also positive for Ngn3 and Pdx1, strongly suggesting that the combined treatment has reversed diabetes in the NOD mice by allowing regeneration of insulin producing beta cells that are not being destroyed by autoimmunity.

This in vivo study demonstrated the effectiveness of the Ex-4 and LSF combination. Both the control and Ex-4 treatments were unable to control hyperglycemia: the mice displayed an increase in blood glucose levels before the pump was removed. Despite LSF's moderate ability to control blood glucose levels when used alone, hyperglycemia returned immediately following the removal of the pump. The mice treated with a combination of Ex-4 and LSF, however, maintained a euglycemic state, and they remained non-diabetic for as long as 20 weeks after the removal of the pump.

The above data shows that the combination of Ex-4 and LSF enhances beta-cell function, reduces apoptosis, and successfully reverses autoimmune diabetes. However, a comparison between tissue of mice treated with both Ex-4 and LSF and tissue of mice in any other treatment group yields significantly more positive staining in the Ex-4 and LSF tissue, which confirms that this combination treatment halts autoimmune destruction and fostering the regeneration of β-cell tissue, further demonstrating its effectiveness as a therapeutic method.

In sum, LSF alone prevented worsening of hyperglycemia during in vivo drug treatment, but blood glucose levels rose after removal of pump. Ex-4 alone caused transient drop in BG, however the group returned to worsening hyperglycemic state before treatment was withdrawn. The combination of LSF and Ex-4 increased mitochondrial metabolism and protected islets and β-cells from pro-inflammatory cytokine damage more effectively than either treatment LSF alone or Ex-4 alone. Further, the combination of LSF and Ex-4 reversed diabetes within first week of implantation of pump, over long-term, mice maintained euglycemia after withdrawing treatment. A near-normal glucose stimulation response was observed along with an increase in cell proliferation in pancreata and evidence of new beta cell formation.

Although illustrative embodiments of the present invention have been described in detail, it is to be understood that the present invention is not limited to those precise embodiments, and that various changes and modifications can be effected therein by one skilled in the art without departing from the scope and spirit of the invention.

What is claimed is:

1. A method for treating Type 1 diabetes, autoimmune diabetes, or insulin dependent diabetes mellitus (IDDM) comprising administering to a mammal in need thereof a therapeutically effective amount of a pharmaceutical composition comprising a biological response modifier and a β-cell growth or differentiating factor in admixture with a pharmaceutically acceptable carrier, adjuvant or vehicle; wherein the biological response modifier is lisofylline and the β-cell growth or differentiating factor is exendin-4 or exenatide.

* * * * *